United States Patent
Voros et al.

(10) Patent No.: US 10,254,272 B2
(45) Date of Patent: Apr. 9, 2019

(54) BLOOD BASED BIOMARKERS FOR DIAGNOSING ATHEROSCLEROTIC CORONARY ARTERY DISEASE

(71) Applicant: Global Genomics Group, LLC, Richmond, VA (US)

(72) Inventors: Szilard Voros, Richmond, VA (US); Bradley O. Brown, Richmond, VA (US); Idean B. Marvasty, Richmond, VA (US)

(73) Assignee: Global Genomics Group, LLC, Midlothian, VA (US)

( * ) Notice: Subject to any disclaimer, the term of this patent is extended or adjusted under 35 U.S.C. 154(b) by 102 days.

(21) Appl. No.: 14/991,644

(22) Filed: Jan. 8, 2016

(65) Prior Publication Data

US 2016/0202239 A1 Jul. 14, 2016

Related U.S. Application Data

(60) Provisional application No. 62/101,445, filed on Jan. 9, 2015.

(51) Int. Cl.
| | |
|---|---|
| *G01N 33/49* | (2006.01) |
| *A61K 31/616* | (2006.01) |
| *A61K 31/37* | (2006.01) |
| *A61K 31/00* | (2006.01) |
| *G01N 33/68* | (2006.01) |

(52) U.S. Cl.
CPC ........... *G01N 33/492* (2013.01); *A61K 31/00* (2013.01); *A61K 31/37* (2013.01); *A61K 31/616* (2013.01); *G01N 33/6812* (2013.01); *G01N 33/6893* (2013.01); *G01N 2570/00* (2013.01); *G01N 2800/324* (2013.01)

(58) Field of Classification Search
None
See application file for complete search history.

(56) References Cited

U.S. PATENT DOCUMENTS

| | | | |
|---|---|---|---|
| 9,103,840 B2* | 8/2015 | Pemberton | G01N 33/74 |
| 2010/0173346 A1 | 7/2010 | Adourian | |
| 2011/0021468 A1* | 1/2011 | Shoelson | A61K 31/185 514/163 |
| 2013/0338031 A1 | 12/2013 | Hu et al. | |
| 2014/0303236 A1 | 10/2014 | Rooij et al. | |

FOREIGN PATENT DOCUMENTS

| | | |
|---|---|---|
| CN | 102971633 A1 | 3/2013 |
| WO | 2002/089657 | 11/2002 |
| WO | WO 2011/063470 | 6/2011 |
| WO | WO 2014/135696 | 9/2014 |

OTHER PUBLICATIONS

Djekic et al., "Metabolomics in atheroschlerosis", IJC Metabolic & Endocrine 8 (2015) 26-30.
ROC Taiwan Patent Application No. 105103174, Office Action dated Dec. 23, 2016, 13 pages.
Albrecht et al., "Metabolite profiling reveals new insights into the regulation of serum urate in humans," Metabolomics. Feb. 2014, vol. 10, No. 1, pp. 141-151.
Bodi et al., "Metabolomic Profile of Human Myocardial Ischemia by Nuclear Magnetic Resonance Spectroscopy of Peripheral Blood Serum: A Translational Study Based on Transient Coronary Occlusion Models," J Am Coll Cardiol, May 2012;59(18):1629-1641.
Cheng et al., "Metabolite Profiling Identifies Pathways Associated With Metabolic Risk in Humans / Clinical Perspective," Circulation, Apr. 2012; 125(18):2222-2231.
DeHaven et al., "Organization of GC/MS and LC/MS metabolomics data into chemical libraries," J Cheminform, Oct. 2010;2(1):9.
Diamond and Forrester, "Analysis of probability as an aid in the clinical diagnosis of coronary-artery disease," New England J Med., Jun. 14, 1979; 300(24):1350-1358.
Evans et al., "Integrated, nontargeted ultrahigh performance liquid chromatography/electrospray ionization tandem mass spectrometry platform for the identification and relative quantification of the small-molecule complement of biological systems," Anal Chem, Aug. 2009;81(16):6656-6667.
Folch et al., "A simple method for the isolation and purification of total lipides from animal tissues," J Biol Chem, May 1957;226(1):497-509.
Friedman, "Greedy function approximation: a gradient boosting machine," Ann Statist, Apr. 2001, 29(5):1189-1232.
Friedman, "Stochastic gradient boosting," Computational Statistics & Data Analysis, Feb. 2002, 38(4):367-378.
International Search Report and Written Opinion in International Application No. PCT/US16/12725, dated Jun. 3, 2016, 12 pages.
Meikle et al. "Plasma Lipidomic Analysis of Stable and Unstable Coronary Artery Disease," Arteriosclerosis, Thrombosis, and Vascular Biology, Nov. 2011; 31(11):2723-2732.
Morise and Jalisis, "Evaluation of pretest and exercise test scores to assess all-cause mortality in unselected patients presenting for exercise testing with symptoms of suspected coronary artery disease," J Am College of Cardiology, Sep. 3, 2003;42(5):842-850.
Patel et al., "Low Diagnostic Yield of Elective Coronary Angiography," New England J Med., Mar. 11, 2010; 362(10):886-895.
Tarasov et al. "Molecular Lipids Identify Cardiovascular Risk and Are Efficiently Lowered by Simvastatin and PCSK9 Deficiency," J Clin Endocrinol Metab, Jan. 2014;99(1):E45-E52.
Thomas et al. "A Blood-Based Gene Expression Test for Obstructive Coronary Artery Disease Tested in Symptomatic Nondiabetic Patients Referred for Myocardial Perfusion Imaging The Compass Study," Circulation: Cardiovascular Genetics, Feb. 2013;6(2):154-162.
American Heart Association Statistical Update, "Heart Disease and Stroke Statistics-2018 Update", Mar. 6, 2018, 442 pages.
Bentzon et al., "Mechanisms of Plaque Formation and Rupture", American Heart Association Circulation Research, 2014; 114:1852-1866.

(Continued)

*Primary Examiner* — Bong-Sook Baek
(74) *Attorney, Agent, or Firm* — Fish & Richardson P.C.

(57) ABSTRACT

The invention, in some aspects, relates to methods for evaluating a human subject for having atherosclerotic coronary artery disease (ASCAD) or as having a coronary atherosclerotic plaque. In some aspects, the invention relates to methods and kits useful for diagnosing, classifying, profiling and treating atherosclerotic CAD and or a coronary atherosclerotic plaque.

23 Claims, 38 Drawing Sheets

Specification includes a Sequence Listing.

(56) References Cited

OTHER PUBLICATIONS

Williams et al., "The Response-to-Retention Hypothesis of Early Atherogenesis", *Arterioscler Thromb Vasc Biol.* May 1995; 15(5):551-561.
Partial European Supplementary Search Report, dated Jul. 6, 2018, 15 pages.
Bozkurt et al., "Current Diagnostic and Treatment Strategies for Specific Dilated Cardiomyopathies," Circulation, 2016, 134:e579-e646.
Laborde et al., "Plasmametabolomics reveals a potential panel of biomarkers for early diagnosis in acute coronary syndrome," Metabolomics, 2014, 10(3):414-424.

* cited by examiner

BLOOD BASED BIOMARKERS FOR DIAGNOSING ATHEROSCLEROTIC CORONARY ARTERY DISEASE

CROSS-REFERENCE TO RELATED APPLICATIONS

This application claims the benefit of U.S. Provisional Patent Application No. 62/101,445, filed Jan. 9, 2015, the entire contents of which are hereby incorporated by reference.

TECHNICAL FIELD

This invention relates to non-invasive methods for diagnosing atherosclerotic coronary artery disease ("ASCAD") and/or detecting a coronary atherosclerotic plaque in a patient, and more particularly to methods of using metabolomic blood-based biomarkers and their combinations to identify patients having atherosclerotic CAD and/or as having a coronary atherosclerotic plaque.

BACKGROUND

Cardiovascular disease (CVD) remains the leading cause of morbidity and mortality both in the United States and worldwide. Based on the 2014 Heart Disease and Stroke Update by the American Heart Association (AHA), 83.6 million American adults have at least one type of CVD (>1 in 3 prevalence). Of these adults, 15.4 million suffer from coronary heart disease (CHD), with the following breakdown: myocardial infarction (MI): 7.6 million and angina pectoris (AP): 7.8 million. It is estimated that by 2030, 43.9% of the US population will have some form of CVD.

The underlying cause of CVD is atherosclerotic coronary artery disease (ASCAD), which begins with the development of an atherosclerotic plaque in the coronary arterial vasculature. Atherosclerosis is of unquestionable importance, in terms of human health and societal cost. It is responsible for coronary artery disease (CAD) and cerebrovascular disease, both of which are leading causes of morbidity and mortality worldwide. Atherosclerosis is also responsible for peripheral arterial disease, a leading medical cause of limb-loss.

The development and progression of atherosclerotic CAD follows two distinct paths that may lead from one to another, and lead to two distinct clinical syndromes. One of the two broad clinical syndromes is "exertional angina", also called "stable angina" or "stable CAD." In this context, progressively growing atherosclerotic plaque leads to progressively worsening coronary arterial luminal stenosis, or narrowing, that starts to impede blood flow to the myocardium (heart muscle). When luminal stenosis, or narrowing, reaches a critical limit, approximately 70% diameter stenosis, there is significant pressure drop over the stenosis, and myocardial perfusion (blood flow to the heart muscle) is compromised, especially during periods of increased myocardial oxygen demand, such as during exertion or emotional states. This myocardial oxygen "supply-demand mismatch" leads to myocardial ischemia, when blood flow to the heart muscle can no longer keep up with demand. It is myocardial ischemia itself that triggers pain receptors in the heart, leading to the clinical symptoms of "angina pectoris", or chest pain. While this process typically causes chest pain during exertion or emotional states, this typically does not lead to acute coronary syndromes, such as sudden cardiac death (SCD), myocardial infarction (MI; heart attack) or unstable angina (UA). Typical treatment options include medical interventions to slow the heart rate with beta blockers or calcium channel blockers, and to improve blood flow with drugs like nitrates. Typical interventional approaches are aimed at relieving the stenosis, by either percutaneously placing a stent inside the stenosis (percutaneous coronary intervention; PCI) to open the narrowing, or to bypass the stenotic (narrowed) segment using arterial or venous grafts during coronary artery bypass grafting (CABG) surgery. As pointed out above, the root cause of this pathophysiology and clinical course of "exertional angina" is coronary arterial atherosclerosis, or atherosclerotic CAD.

The second broad path in pathophysiology with a corresponding clinical picture is referred to as "acute coronary syndromes" (ACS), which encompasses sudden cardiac death (SCD), myocardial infarction (MI) and unstable angina (UA). In this context, the atherosclerotic plaque (the root cause) in the coronary artery can get disrupted either through rupture, or erosion. When a coronary atherosclerotic plaque gets disrupted, this triggers the formation of a thrombus (clot) over the disrupted region, which may partially or completely occlude the entire coronary artery, leading to abrupt cutoff of blood supply to the myocardium (acute myocardial ischemia). This pathophysiology may manifest in sudden cardiac death (SCD), myocardial infarction (MI), or resting angina. Typical treatment options are commonly interventional options, where the acutely disrupted plaque is covered up with a stent during an invasive procedure. Just as in the case of "exertional angina", the root cause of acute coronary syndromes is atherosclerotic plaque in the coronary arterial vasculature.

Accordingly, the initiation and progression of atherosclerotic plaques are the root cause of the clinical manifestations of atherosclerotic CAD and CHD. Thus, there remains a need for improved diagnostic methods for detecting an atherosclerotic plaque and for diagnosing atherosclerotic CAD.

SUMMARY

In one aspect, the disclosure provides non-invasive methods for evaluating a human subject for having atherosclerotic coronary artery disease (ASCAD) or as having a coronary atherosclerotic plaque. ASCAD includes, for example, atherosclerosis. The methods include measuring the levels of each analyte within a panel of analyte biomarkers in a biological sample obtained from a subject, wherein the panel of analyte biomarkers is selected from the group consisting of:

(i) a panel of biomarkers comprising valylleucine, glutamate, acisoga, urate, glucuronate, fucose, butyrylcarnitine (C4) and mannose;

(ii) a panel of biomarkers comprising acisoga, o-cresol-.sulfate, threonate and cysteine-glutathione disulfide;

(iii) a panel of biomarkers comprising N-acetylphenylalanine, N-acetylleucine, valylleucine, xylitol, 2-hydroxyhippurate (salicylurate), glycylphenylalanine, serylleucine and fucose;

(iv) a panel of biomarkers comprising glutamate, acisoga, valylleucine, mannose, glucuronate, urate, valerylcarnitine (C5) and 12-HETE;

(v) a panel of biomarkers comprising o-cresol sulfate, acisoga, cysteine-glutathione disulfide, glucose, 1-nonadecanoylglycerophosphocholine (19:0) and threonate;

(vi) a panel of biomarkers comprising N-acetylphenylalanine, N-acetylleucine, glycylphenylalanine, valylleucine, xylitol, 12-HETE and 2-hydroxyhippurate (salicylurate);

(vii) a panel of biomarkers comprising N-acetylthreonine, tigloylglycine, glycerate, valerylcarnitine (C5), threonate, 2-hydroxyhippurate (salicylurate), salicylate and tartronate (hydroxymalonated);

(viii) a panel of biomarkers comprising N-acetylglycine and 3-ethylphenyl sulfate;

(viv) a panel of biomarkers comprising serotonin (5HT), N-acetylputrescine, leucylleucine, propionylglycine (C3), cholate, glycocholenate sulfate, asparagine and 3-ethylphenyl sulfate;

(x) a panel of biomarkers comprising acisoga, mannose, valerylcarnitine (C5), 1-linoleoyl-GPE (18.2), glycoursodeoxycholate, threonate, 2-hydroxyhippurate (salicylurate) and salicylate;

(xi) a panel of biomarkers comprising N-acetylglycine, threonate, 2-hydroxyhippurate (salicylurate), 3-ethylphenylsulfate and salicylate;

(xii) a panel of biomarkers comprising asparagine, taurine, acisoga, 1-oleoylglycerol (18:1), cholesterol, 2-hydroxyhippurate (salicylurate), 6-oxopiperidine-2-carboxylic acid and propionylglycine (C3), wherein the levels, including relative levels, or the occurrences of the plurality of analyte biomarkers are indicative of having ASCAD and/or for the presence of a coronary atherosclerotic plaque. Any of the panels above may further include the analysis of age and gender.

In another aspect, the disclosure provides a method comprising measuring by mass spectrometry the levels of each of a plurality of metabolites in a blood sample obtained from a human subject, wherein the plurality of metabolites is selected from the group consisting of (i) valylleucine, glutamate, acisoga, urate, glucuronate, fucose, butyrylcarnitine (C4) and mannose; (ii) cisoga, o-cresol sulfate, threonate and cysteine-glutathione disulfide; (iii) N-acetylphenylalanine, N-acetylleucine, valylleucine, xylitol, 2-hydroxyhippurate (salicylurate), glycylphenylalanine, serylleucine and fucose; (iv) glutamate, acisoga, valylleucine, mannose, glucuronate, urate, valerylcarnitine (C5) and 12-HETE; m(v) o-cresol sulfate, acisoga, cysteine-glutathione disulfide, glucose, 1-nonadecanoylglycerophosphocholine (19:0) and threonate; (vi) N-acetylphenylalanine, N-acetylleucine, glycylphenylalanine, valylleucine, xylitol, 12-HETE and 2-hydroxyhippurate (salicylurate); (vii) N-acetylthreonine, tigloylglycine, glycerate, valerylcarnitine (C5), threonate, 2-hydroxyhippurate (salicylurate), salicylate and tartronate (hydroxymalonated); (viii) N-acetylglycineN-acetylglycine and 3-ethylphenyl sulfate; (viv) serotonin (5HT), N-acetylputrescine, leucylleucine, propionylglycine (C3), cholate, glycocholenate sulfate, asparagine and 3-ethylphenyl sulfate; (x) acisoga, mannose, valerylcarnitine (C5), 1-linoleoyl-GPE (18.2), glycoursodeoxycholate, threonate, 2-hydroxyhippurate (salicylurate) and salicylate; (xi) N-acetylglycine, threonate, 2-hydroxyhippurate (salicylurate), 3-ethylphenylsulfate, salicylate; and (xii) asparagine, taurine, acisoga, 1-oleoylglycerol (18:1), cholesterol, 2-hydroxyhippurate (salicylurate), 6-oxopiperidine-2-carboxylic acid, and propionylglycine (C3).

In one aspect, the disclosure provides methods for evaluating a human subject for having ASCAD or as having a coronary atherosclerotic plaque which comprises measuring the levels of each analyte within a panel of analyte biomarkers in a biological sample obtained from a subject, wherein the panel of analyte biomarkers is selected from the group consisting of:

(xiii) a panel of biomarkers comprising valylleucine, isoleucylvaline, glutamine-leucine, X-12212, glucuronate, and glutamate;

(xiv) a panel of biomarkers comprising glucose, gamma-glutamyl transferase, uric acid, low density lipoprotein cholesterol, triglycerides, lipoprotein (a) mass, alkaline phosphatase, and apolipoprotein B;

(xv) a panel of biomarkers comprising glutamate, X-16132, isoleucylalanine, isoleucylphenylalanine, lipoprotein (a) mass, small dense low density lipoprotein cholesterol, X-12212. ADSGEGDFXAEGGGVR (SEQ ID NO: 1), glutamine, leucine, and threonylleucine;

(xvl) a panel of biomarkers comprising CER22.1, Hex-CER18:1, TG15:0, SM16:0, CER20:0, DHC20:1, and CER18:0;

(xvii) a panel of biomarkers comprising CER20:0, apolipoprotein B, SM16:0, lipoprotein (a) mass, DHC20L1, alkaline phosphatase, and CER18:0;

(xviii) a panel of biomarkers comprising glutamate, X-16132, isoleucylalanine, Lipoprotein (a) mass, X-12212, and glutamine-leucine;

(xix) a panel of biomarkers comprising oleic2, N-terminal pro-brain natriuretic peptide, lipoprotein (a) mass, insulin, glycated hemoglobin A1C, cismontaotl, small dense low density lipoprotein cholesterol, behenic2, adiponectin, and gamma-glutamyl transferase;

(xx) a panel of biomarkers comprising isoleucylalanine, glucuronate, glycine, isoleucylphenylalanine, mannose, X-21452, 1-oleoylglycerophosphoglycerol, X-21335, 7-methylxanthine, X-12729, acisoga, alpha-hydroxyisovaleroyl carnitine, 2-aminoadipate, X-18914, tigloylglycine, and pyridoxal;

(xxi) a panel of biomarkers comprising isoleucylalanine, glycine, isoleucylphenylalanine, oleic2, X-21335, methylxanthine, aminoadipate, mannose, acisoga, arachidonoyl-.GPE.20.4, and triglycerides;

(xxii) a panel of biomarkers comprising DHC18:0, DG18:1n9, total diacylglycerol, TG20:3n9, CE20:4n6, CER18:1, DHC20:1, CE18:2n6, PL18:2n6, SM18:0, FA14:1n5, PL15:0, and CE16:0;

(xxiii) a panel of biomarkers comprising glycated hemoglobin A1C, total diacylglycerol, cismontotl, lipoprotein (a) mass, TG20.3n9, oleic2, DHC18.1, N-terminal pro-brain natriuretic peptide, gamma-glutamyl transferase, and CER18;

(xxiv) a panel of biomarkers comprising isoleucylalanine, glycine, cismontotl, lipoprotein (a) mass, X-21452, isoleucylphenylalanine, glycated hemoglobin A1C, X-21335, X7.methylxanthine, acisoga and X-12729; wherein the levels, including relative levels, or the occurrences of the plurality of analyte biomarkers are indicative of having atherosclerotic coronary artery disease (ASCAD) or the presence of a coronary atherosclerotic plaque.

Also provided in aspects of the invention are panels of biomarkers useful for evaluating a human subject for having ASCAD or as having a coronary atherosclerotic plaque. By a "panel of biomarkers" it is meant a collection, or combination, of two or more molecular entities, e.g. two, three, four, five, or more than five entities, whose representation in a sample is associated with ASCAD or a coronary atherosclerotic plaque. The panel of biomarkers described herein may be used to diagnose ASCAD or identify the presences of a coronary atherosclerotic plaque, to provide a prognosis to a patient having ASCAD or a coronary atherosclerotic plaque, to provide a prediction of the responsiveness of a patient with ASCAD or a coronary atherosclerotic plaque to a medical therapy, to monitor a patient having ASCAD or a coronary atherosclerotic plaque, to treat a patient having ASCAD or a coronary atherosclerotic plaque, etc.

In some embodiments, the methods further comprise of performing a comparison between the measured levels of the analytes in the biological sample with one or more reference samples, said references being representative of matched (e.g., age, gender, etc.) human subjects.

In some embodiments, the methods further include identifying a subject as having ASCAD or as having a coronary atherosclerotic plaque if the measured levels of the analytes in the biological sample are increased or decreased relative to the amounts of the analytes in the reference samples.

In some embodiments, the methods include instructing a healthcare professional (e.g., a physician, physician assistant, nurse practitioner, nurse and case manager) to complete a non-invasive cardiovascular evaluation on a subject identified as having atherosclerotic coronary artery disease or as having a coronary atherosclerotic plaque. The further non-invasive cardiovascular evaluation can confirm whether the subject has or does not have atherosclerotic coronary artery disease or a coronary atherosclerotic plaque.

In some embodiments, the methods further comprise of performing a non-invasive cardiovascular evaluation on a subject identified as having ASCAD or as having a coronary atherosclerotic plaque to confirm the subject does or does not have atherosclerotic coronary artery disease or a coronary atherosclerotic plaque. The non-invasive cardiovascular evaluation can be a procedure selected from the group consisting of cardiovascular computed tomography (CT) imaging, an exercise stress test, a pharmacologic stress test, myocardial perfusion imaging, stress echocardiography, and cardiovascular magnetic resonance imaging.

In yet another embodiment, the methods further comprise selectively administering a composition comprising an effective amount of a therapeutic agent to a subject identified as having atherosclerotic coronary artery disease or as having a coronary atherosclerotic plaque to treat the subject, wherein the therapeutic agent is selected from the group consisting of a statin, cholesterol absorption inhibitors, niacin-derivatives, omega-3-fatty acid compounds, bile acid sequestrants, PCSK9 inhibitor, anti-platelet agents, aldosterone blockers, angiotensin-converting enzyme (ACE) inhibitors, angiotensin-receptor blockers (ARBs), beta blockers, diuretics, digitalis, hydralazine and nitrates, warfarin and aspirin.

For subjects identified as having ASCAD or as having a coronary atherosclerotic plaque, the methods may further comprise selecting a treatment plan for a subject. For example, the methods may further comprise selecting a treatment plan for a subject, which comprises selectively administering a composition comprising an effective amount of a therapeutic agent, and/or performing a non-invasive cardiovascular evaluation, which comprises, for example, performing a procedure selected from the group consisting of cardiovascular computed tomography (CT) imaging, an exercise stress test, a pharmacologic stress test, myocardial perfusion imaging, stress echocardiography, and cardiovascular magnetic resonance imaging. The treatment plan can comprise prescribing to the subject therapeutic lifestyle changes to improve cardiovascular health.

In some embodiments, the level of each analyte is measured using mass spectrometry (MS) analysis. The MS analysis method can be liquid chromatography-tandem mass spectrometry (UPLC-MS/MS), chromatography-mass spectrometry (GC-MS), or nuclear magnetic resonance (NMR).

In some aspects, the methods disclosed herein further comprise selecting a subject identified as having ASCAD or as having a coronary atherosclerotic plaque for treatment. In some embodiments, the treatment comprises selectively administering a composition comprising an effective amount of a therapeutic agent selected from the group consisting of a statin, cholesterol absorption inhibitors, niacin-derivatives, omega-3-fatty acid compounds, bile acid sequestrants, PCSK9 inhibitors, anti-platelet agents, aldosterone blockers, angiotensin-converting enzyme (ACE) inhibitors, angiotensin-receptor blockers (ARBs), beta blockers, diuretics, digitalis, hydralazine and nitrates, warfarin and aspirin to a subject identified as having atherosclerotic coronary artery disease or as having a coronary atherosclerotic plaque to treat the subject. In some embodiments, the treatment comprises performing a non-invasive cardiovascular evaluation on a subject identified as having atherosclerotic coronary artery disease or as having a coronary atherosclerotic plaque to confirm whether the subject does or does not have atherosclerotic coronary artery disease or a coronary atherosclerotic plaque. In some embodiments, the treatment plan comprises prescribing therapeutic lifestyle changes to improve cardiovascular health.

In another aspect, the invention provides a kit for evaluating a human subject for having ASCAD or as having a coronary atherosclerotic plaque. The kits include reagents suitable for determining levels of a plurality of analytes in a test sample (e.g., reagents suitable for determining levels of the metabolomic biomarkers disclosed herein); optionally one or more control samples comprising predetermined levels of the same analytes, wherein comparison of the levels of the analytes in a test sample with levels in the control samples identifies a subject as having atherosclerotic coronary artery disease or as having a coronary atherosclerotic plaque; and instructions for use of the kit in the method described herein.

As used herein, the term "biological sample" or "sample" refers to a sample obtained or derived from a subject. By way of example, the sample may be selected from the group consisting of body fluids, blood, whole blood, plasma, serum, mucus secretions, urine or saliva. In some embodiments the sample is, or comprises a blood sample. The preferred biological source for detection of the biomarkers is a blood sample, a serum sample or a plasma sample.

The term "subject" as used herein refers to a mammal. A subject therefore refers to, for example, dogs, cats, horses, cows, pigs, guinea pigs, humans and the like. When the subject is a human, the subject may be referred to herein as a patient. The subject can be symptomatic (e.g., the subject presents symptoms associated with atherosclerotic CAD, such as, for example, chest pain, angina, angina equivalent, dyspnea, or dyspnea on exertion; and/or presents risk factors associated with coronary artery disease, such as, for example, male gender, hypertension, dyslipidemia, diabetes, post-menopausal state in females, smoking, or a family history of coronary artery disease), or the subject can be asymptomatic (e.g., the subject does not present symptoms associated with atherosclerotic CAD).

As used herein, "obtain" or "obtaining" can be any means whereby one comes into possession of the sample by "direct" or "indirect" means. Directly obtaining a sample means performing a process (e.g., performing a physical method such as extraction) to obtain the sample. Indirectly obtaining a sample refers to receiving the sample from another party or source (e.g., a third party laboratory that directly acquired the sample). Directly obtaining a sample includes performing a process that includes a physical change in a physical substance, e.g., a starting material, such as a blood, e.g., blood that was previously isolated from a patient. Thus, obtain is used to mean collection and/or removal of the sample from the subject. Furthermore, "obtain" is also used to mean where one receives the sample from another who was in possession of the sample previously.

In some embodiments, the reference sample is obtained from at least one individual not suffering from a cardiovascular disease. In some other embodiments, the reference sample is obtained from at least one individual previously diagnosed as having a cardiovascular disease (e.g., atherosclerotic coronary artery disease (ASCAD) or a coronary atherosclerotic plaque). In some embodiments, the reference sample comprises a predetermined, statistically significant reference analyte levels.

In some embodiments, the determining step is performed using a gradient boosting algorithm. In some embodiments, the determining step is performed using generalized linear modeling.

In yet another embodiment, the methods further comprise modifying the subject's clinical record to identify the subject as having atherosclerotic coronary artery disease or as having a coronary atherosclerotic plaque. Preferably, the clinical record is stored in a computer readable medium.

A summary of the relevant analysis models described herein are provided below:
a. Atherosclerosis in Native CAD—$A^{nCAD}$
  i. Significant in Fasting & Non-Fasting Combined—$A_{FNF}^{nCAD}$
  ii. Independently Significant in Fasting and Non-Fasting—$A_{IFNF}^{nCAD}$
  iii. Significant in Fasting—$A_{F}^{nCAD}$
b. Atherosclerosis in All CAD (including revascularization)—$A^{aCAD}$
  i. Significant in Fasting & Non-Fasting Combined—$A_{FNF}^{aCAD}$
  ii. Independently Significant in Fasting and Non-Fasting—$A_{IFNF}^{aCAD}$
  iii. Significant in Fasting—$A_{F}^{aCAD}$
c. 50% stenosis in Native CAD
  i. Significant in Fasting & Non-Fasting Combined—$S_{FNF}^{nCAD}$
  ii. Independently Significant in Fasting and Non-Fasting—$S_{IFNF}^{nCAD}$
  iii. Significant in Fasting—$S_{F}^{nCAD}$
d. 50% stenosis in ALL CAD (including revascularization)
  i. Significant in Fasting & Non-Fasting Combined—$S_{FNF}^{aCAD}$
  ii. Independently Significant in Fasting and Non-Fasting—$S_{IFNF}^{aCAD}$
  iii. Analytes Significant in Fasting—$S_{F}^{aCAD}$.

The section headings used herein are for organizational purposes only and are not to be construed as limiting the described subject matter in any way. When definitions of terms in incorporated references appear to differ from the definitions provided in the present teachings, the definition provided in the present teachings shall control. It will be appreciated that there is an implied "about" prior to metrics such as temperatures, concentrations, and times discussed in the present teachings, such that slight and insubstantial deviations are within the scope of the present teachings herein. In this application, the use of the singular includes the plural unless specifically stated otherwise. Also, the use of "comprise," "comprises," "comprising," "contain," "contains," "containing," "include," "includes," and "including" are not intended to be limiting. It is to be understood that both the foregoing general description and the following detailed description are exemplary and explanatory only and are not restrictive of the invention. The articles "a" and "an" are used herein to refer to one or to more than one (i.e., to at least one) of the grammatical object of the article. By way of example, "an element" means one element or more than one element.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DETAILED DESCRIPTION

The initiation and progression of atherosclerotic plaques is the root cause of the clinical manifestations of atherosclerotic CAD and CHD. The first step and the "sine qua non" of atherosclerosis, is the retention of atherogenic lipoprotein particles, which is followed by a compensatory, secondary inflammatory response. The infiltration of the coronary arterial wall by monocytes and macrophages creates a feedback loop that further triggers the progression of atherosclerosis. The macrophages in the coronary arterial wall start the phagocytosis of atherogenic lipoprotein particles and the uncontrolled uptake of atherogenic lipids and lipoproteins leads to apoptosis and necrosis of the macrophages, creating a lipid-rich necrotic core (LRNC). It is this state of the LRNC that is most susceptible to rupture and erosions. Later stages of the atherosclerotic process involve healing through calcification and fibrosis.

It follows that blood-based biomarkers provide insight into the atherosclerotic process at two levels. First, blood-based biomarkers can assess causal factors that lead to the development of atherosclerosis; and second, blood-based biomarkers can assess the consequences and responses to the initial steps in the atherosclerotic process.

Figure 31:
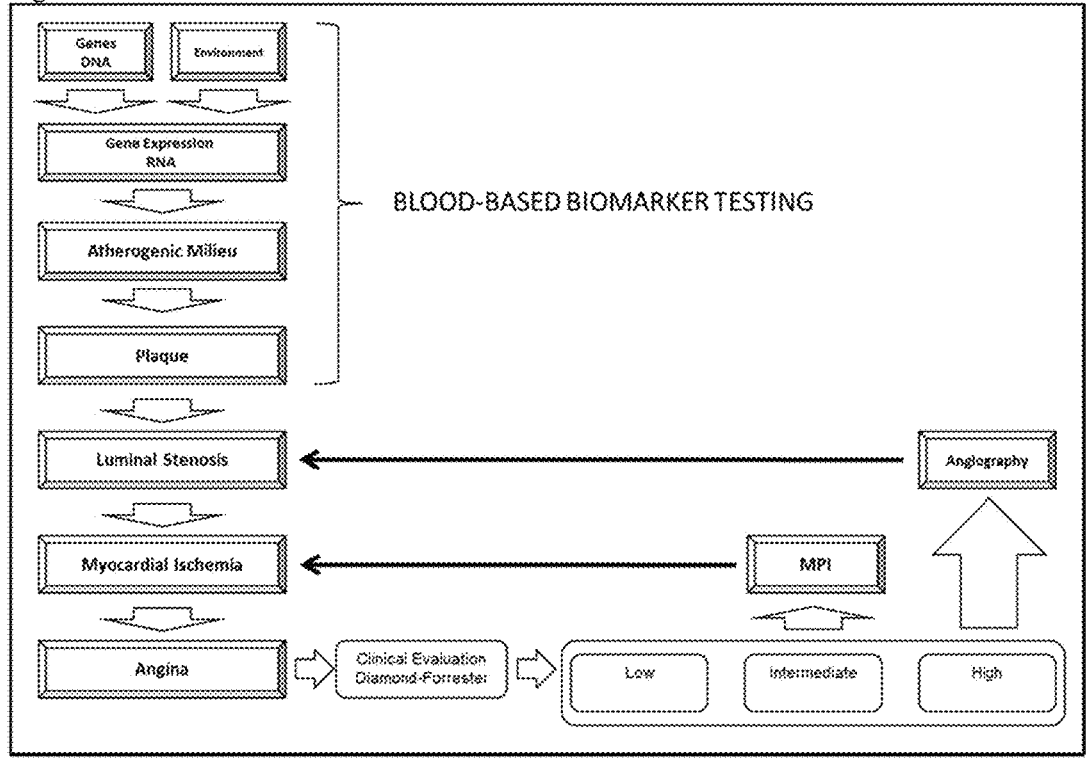
FIG. 31 is a schematic diagram describing a diagnostic algorithm in patient suspected of having atherosclerotic CAD.
Figure 32:
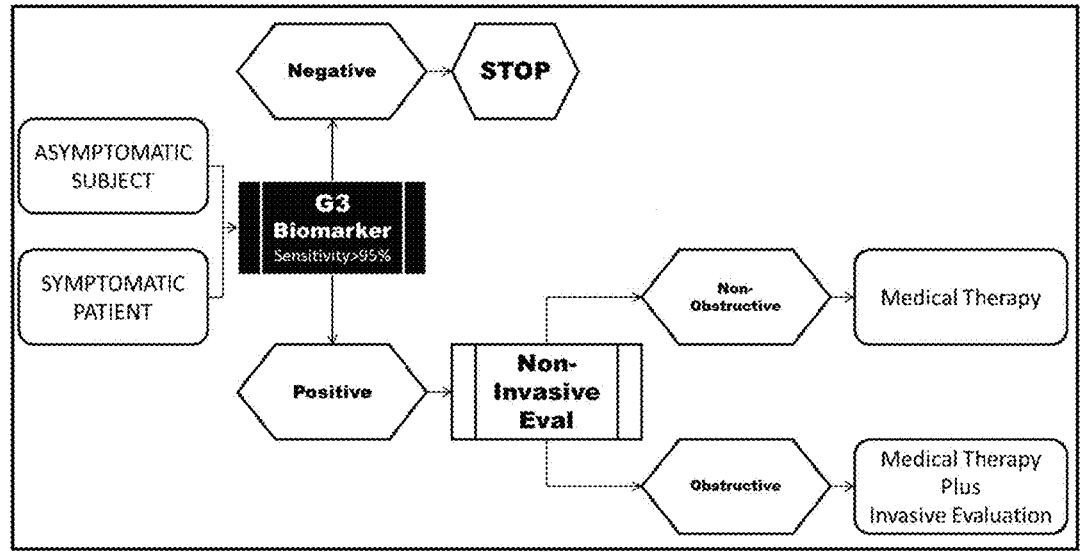
FIG. 32 is a schematic diagram describing a diagnostic algorithm evaluating a subject for having atherosclerotic coronary artery disease or as having a coronary atherosclerotic plaque.
Figure 33:
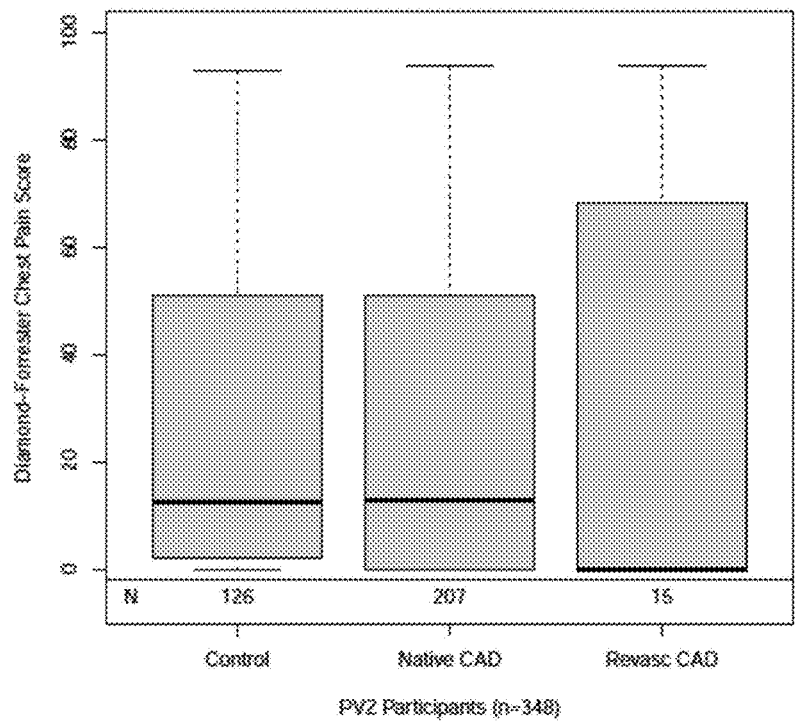
FIG. 33 is a graph demonstrating a box plot of Diamond Forrester Score by clinical group.
Figure 34:
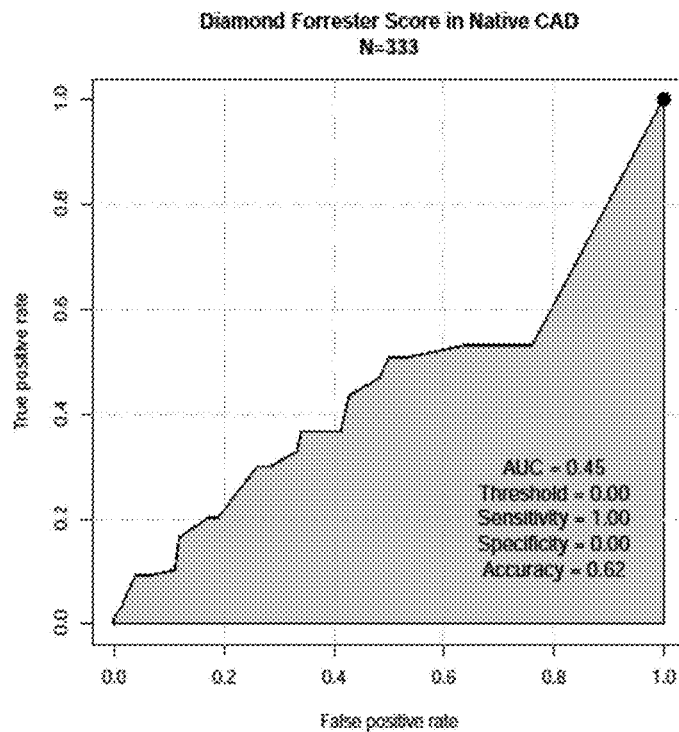
FIG. 34 is a graph demonstrating a ROC curve for Diamond Forrester Score and $A^{nCAD}$ (AUC=0.45; Threshold=0.00; Sensitivity=1.00; Specificity=0.00; Accuracy=0.62).

In contrast to the biological paradigm outlined above, the clinical diagnosis of atherosclerotic CAD is predicated on population-based probability-driven clinical risk stratification (FIG. 31).

The clinical diagnostic algorithm depends on clinical risk- and symptom-based risk stratification. Asymptomatic patients are evaluated through global risk scores, such as the Framingham Risk Score, or the more recently developed and introduced Pooled Risk Estimator. These global risk scores attempt to estimate the probability of a cardiovascular event occurring over a period of time, but are not designed to make the diagnosis of atherosclerotic CAD.

The clinical evaluation of symptomatic patients, those who are suspected of having atherosclerotic CAD based on their symptoms, is driven by risk scores such as the Diamond-Forrester algorithm. The Diamond-Forrester system classifies patients into one of three categories to provide a pre-test likelihood of obstructive CAD (low [<15%], intermediate [15-85%] or high [>85%]), based on age, gender and clinical attributes of chest pain. In patients with low pre-test likelihood of CAD, no further evaluation is recommended. The largest group of patients is those with intermediate pre-test likelihood of CAD. In this group, the recommendation is to perform a myocardial perfusion imaging (MPI) study to assess the hemodynamic consequence of any potential luminal stenosis. While the published sensitivity and specificity of is approximately 80% and 80% in the research studies, real-life accuracy of MPI is vastly lower than this, with specificity often under 30% (Thomas G S, et al. *A Blood-Based Gene Expression Test for Obstructive Coronary Artery Disease Tested in Symptomatic Nondiabetic Patients Referred for Myocardial Perfusion Imaging The COMPASS Study*. Circulation: Cardiovascular Genetics 2013; 6(2):154-162.). Patients with high pre-test likelihood of CAD are referred for invasive coronary angiography to define the degree and extent of luminal stenosis, and to further refer for percutaneous or surgical revascularization, as appropriate.

Importantly, in this paradigm, none of the diagnostic approaches have been designed to diagnose the root cause of atherosclerotic CAD, the atherosclerotic plaque itself. However, in the context of unbiased, hypothesis-free discovery studies using specific phenotyping tools for the detection of atherosclerotic plaque itself, it is now possible to discover blood-based biomarker signatures of atherosclerotic coronary artery disease and atherosclerotic plaque per se.

The blood-based biomarkers disclosed herein allow for detection of an atherosclerotic plaque per se and allow for early diagnosis of disease and provide an opportunity to significantly change the downstream diagnostic evaluation and treatment process.

The blood-based biomarkers identified herein are designed to detect atherosclerotic CAD by directly detecting atherosclerotic plaque and are calibrated to have a high negative predictive value. Asymptomatic subjects at risk for atherosclerotic CAD, or symptomatic patients suspected of having atherosclerotic CAD are candidates for the biomarker testing. If the test is negative, this excludes the presence of atherosclerotic CAD, and no further testing is warranted. If the test is positive, this indicates the presence of an atherosclerotic plaque and the presence of atherosclerotic CAD, and the patient can be referred for cardiovascular CT, or other non-invasive cardiovascular diagnostic testing to confirm the results. If the cardiovascular CT or other non-invasive cardiovascular diagnostic testing detects non-obstructive plaque and non-obstructive CAD, the patient is prescribed medical therapy to treat the factors that lead to the development of the plaque, in order to halt or reverse the further progression of atherosclerotic CAD. If, on the other hand, the cardiovascular CT examination or other non-invasive cardiovascular diagnostic testing shows the presence of obstructive atherosclerotic plaque and obstructive CAD, the patient is referred for invasive coronary angiography, with or without functional testing, to determine if the plaque causes hemodynamically significant stenosis, and coronary revascularization may be performed, as appropriate. Therefore, in this paradigm, the blood-based biomarker plays a central role in determining patient management. Of note, it is well-known that approximately 39% of all invasive coronary angiograms in the United States show no significant coronary artery disease, and another ~20% have non-obstructive CAD (Patel M, et al., *Low Diagnostic Yield of Elective Coronary Angiography*. N Engl J Med. 2010 Mar. 11; 362(10): 886-95). The proportion of negative or non-obstructive CT angiograms are even higher; therefore, the blood-based biomarker that can exclude the presence of atherosclerotic CAD will avoid a very large number of unnecessary invasive and CT coronary angiograms, and other non-invasive cardiovascular diagnostic tests.

Previously, metabolomics approaches have been attempted in the context of CVD, but not in the context of atherosclerotic CAD. Cheng et al. have identified branched-chain amino acids, other hydrophobic amino acids, tryptophan breakdown products, and nucleotide metabolites associated with cardiovascular disease. (Cheng S, et al., *Metabolite Profiling Identifies Pathways Associated With*

*Metabolic Risk in Humans/Clinical Perspective*. Circulation 2012; 125(18):2222-2231). Rather than evaluating atherosclerosis, Bodi et al. have used myocardial ischemia as an outcomes variable to identify metabolic signatures. (Bodi V, Sanchis J, Morales J M, Marrachelli V G, Nunez J, Forteza M J et al. Metabolomic Profile of Human Myocardial Ischemia by Nuclear Magnetic Resonance Spectroscopy of Peripheral Blood Serum: A Translational Study Based on Transient Coronary Occlusion Models. J Am Coll Cardiol 2012; 59(18):1629-1641)

The terms "decrease", "decreased", "reduced", "reduction" or 'down-regulated" are all used herein generally to mean a decrease by a statistically significant amount. However, for avoidance of doubt, "reduced", "reduction", "decreased" or "decrease" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (i.e. absent level as compared to a reference sample), or any decrease between 10-100% as compared to a reference level, or at least about a 0.5-fold, or at least about a 1.0-fold, or at least about a 1.2-fold, or at least about a 1.5-fold, or at least about a 2-fold, or at least about a 3-fold, or at least about a 4-fold, or at least about a 5-fold or at least about a 10-fold decrease, or any decrease between 1.0-fold and 10-fold or greater as compared to a reference level.

The terms "increased", "increase" or "up-regulated" are all used herein to generally mean an increase by a statistically significant amount; for the avoidance of any doubt, the terms "increased" or "increase" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 0.5-fold, or at least about a 1.0-fold, or at least about a 1.2-fold, or at least about a 1.5-fold, or at least about a 2-fold, or at least about a 3-fold, or at least about a 4-fold, or at least about a 5-fold or at least about a 10-fold increase, or any increase between 1.0-fold and 10-fold or greater as compared to a reference level.

The present invention relates to methods useful for the characterization of (e.g., clinical evaluation, diagnosis, classification, prediction, profiling) of atherosclerotic CAD and or coronary atherosclerotic plaque based on the levels or occurrence of certain analytes referred to herein as biomarkers, or analyte biomarkers. As used herein, levels refer to the amount or concentration of an analyte in a sample (e.g., a plasma or serum sample) or subject. Whereas, occurrence refers to the presence or absence of a detectable analyte in a sample. Thus, level is a continuous indicator of amount, whereas occurrence is a binary indicator of an analyte. In some cases, an occurrence may be determined using a threshold level above which a biomarker is present and below which a biomarker is absent.

The analyte biomarkers described herein are particularly useful for characterizing (e.g., assessing or evaluating) a subject for having atherosclerotic CAD or as having a coronary atherosclerotic plaque in a non-invasive manner.

The invention relates to the discovery of a plurality of biomarkers that are useful for characterizing an atherosclerosis-related metabolic disorder. Thus, in some aspects, the invention provides method comprising measuring the level of each analyte within a selected panel of analyte biomarkers, wherein a panel comprises a plurality of analyte biomarkers, in a biological sample obtained from a subject. The number of biomarkers, or metabolites, in the plurality (at least two) may be 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, or 20 or more, e.g., 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or more.

The methods described herein are useful for identifying whether a subject has ASCAD or has a coronary atherosclerotic plaque. Stated another way, the methods described herein are useful for determining the probability a subject has atherosclerotic CAD or has a coronary atherosclerotic plaque, the methods relying on differences in the relative amounts of the analyte biomarker panels obtained from the subject, wherein the probability is determined using a gradient boosting algorithm or generalized linear model, as described herein.

Moreover, the methods described herein are useful for diagnosing whether a subject has atherosclerotic CAD or has a coronary atherosclerotic plaque. As used herein, diagnosing includes both diagnosing and aiding in diagnosing. Thus, other diagnostic criteria may be evaluated in conjunction with the results of the methods in order to make a diagnosis.

According to some embodiments, the method comprises determining the amount (i.e., determining the level, measuring the amount, or measuring the level) of each (i.e., all) analyte within a panel of analyte biomarkers. In some embodiments, any of the panels below may further include the analysis of the age and/or gender of the subject.

In some embodiments, the analytes are selected from the group consisting of valylleucine, glutamate, acisoga, urate, glucuronate, fucose, butyrylcarnitine (C4), mannose. Thus, in some embodiments, the methods disclosed herein comprise measuring the levels of the following analytes in the sample: valylleucine, glutamate, acisoga, urate, glucuronate, fucose, butyrylcarnitine (C4), mannose.

In some embodiments, the analytes are selected from the group consisting of acisoga, o-cresol sulfate, threonate, cysteine-glutathione disulfide. Thus, in some embodiments, the methods disclosed herein comprise measuring the levels of the following analytes in the sample: acisoga, o-cresol sulfate, threonate, cysteine-glutathione disulfide.

In some embodiments, the analytes are selected from the group consisting of N-acetylphenylalanine, N-acetylleucine, valylleucine, xylitol, 2-hydroxyhippurate (salicylurate), glycylphenylalanine, serylleucine, fucose. Thus, in some embodiments, the methods disclosed herein comprise measuring the levels of the following analytes in the sample: N-acetylphenylalanine, N-acetylleucine, valylleucine, xylitol, 2-hydroxyhippurate (salicylurate), glycylphenylalanine, serylleucine, fucose.

In some embodiments, the analytes are selected from the group consisting of glutamate, acisoga, valylleucine, mannose, glucuronate, urate, valerylcarnitine (C5), 12-HETE. Thus, in some embodiments, the methods disclosed herein comprise measuring the levels of the following analytes in the sample: glutamate, acisoga, valylleucine, mannose, glucuronate, urate, valerylcarnitine (C5), 12-HETE.

In some embodiments, the analytes are selected from the group consisting of o-cresol sulfate, acisoga, cysteine-glutathione disulfide, glucose, 1-nonadecanoylglycerophosphocholine (19:0), threonate. Thus, in some embodiments, the methods disclosed herein comprise measuring the levels of the following analytes in the sample: o-cresol sulfate, acisoga, cysteine-glutathione disulfide, glucose, 1-nonadecanoylglycerophosphocholine (19:0), threonate.

In some embodiments, the analytes are selected from the group consisting of N-acetylphenylalanine, N-acetylleucine, glycylphenylalanine, valylleucine, xylitol, 12-HETE, 2-hydroxyhippurate (salicylurate). Thus, in some embodiments, the methods disclosed herein comprise measuring the levels of the following analytes in the sample: N-acetylphenylalanine, N-acetylleucine, glycylphenylalanine, valylleucine, xylitol, 12-HETE, 2-hydroxyhippurate (salicylurate).

In some embodiments, the analytes are selected from the group consisting of N-acetylthreonine, tigloylglycine, glycerate, valerylcarnitine (C5), threonate, 2-hydroxyhippurate (salicylurate), salicylate, tartronate (hydroxymalonated). Thus, in some embodiments, the methods disclosed herein comprise measuring the levels of the following analytes in the sample: N-acetylthreonine, tigloylglycine, glycerate, valerylcarnitine (C5), threonate, 2-hydroxyhippurate (salicylurate), salicylate, tartronate (hydroxymalonated).

In some embodiments, the analytes are selected from the group consisting of N-acetylglycine, 3-ethylphenylsulfate. Accordingly, in some embodiments, the methods disclosed herein comprise measuring the levels of the following analytes in the sample: N-acetylglycine, 3-ethylphenylsulfate.

In some embodiments, the analytes are selected from the group consisting of serotonin (5HT), N-acetylputrescine, leucylleucine, propionylglycine (C3), cholate, glycocholenate sulfate, asparagine, 3-ethylphenylsulfate. Accordingly, in some embodiments, the methods disclosed herein comprise measuring the levels of the following analytes in the sample: serotonin (5HT), N-acetylputrescine, leucylleucine, propionylglycine (C3), cholate, glycocholenate sulfate, asparagine, 3-ethylphenylsulfate.

In some embodiments, the analytes are selected from the group consisting of acisoga, mannose, valerylcarnitine (C5), 1-linoleoyl-GPE (18.2), glycoursodeoxycholate, threonate, 2-hydroxyhippurate (salicylurate), salicylate. Accordingly, in some embodiments, the methods disclosed herein comprise measuring the levels of the following analytes in the sample: acisoga, mannose, valerylcarnitine (C5), 1-linoleoyl-GPE (18.2), glycoursodeoxycholate, threonate, 2-hydroxyhippurate (salicylurate), salicylate.

In some embodiments, the analytes are selected from the group consisting of N-acetylglycine, threonate, 2-hydroxyhippurate (salicylurate), 3-ethylphenylsulfate, salicylate. Accordingly, in some embodiments, the methods disclosed herein comprise measuring the levels of the following analytes in the sample: N-acetylglycine, threonate, 2-hydroxyhippurate (salicylurate), 3-ethylphenylsulfate, salicylate.

In some embodiments, the analytes are selected from the group consisting of asparagine, taurine, acisoga, 1-oleoylglycerol (18:1), cholesterol, 2-hydroxyhippurate (salicylurate), 6-oxopiperidine-2-carboxylic acid, propionylglycine (C3). Accordingly, in some embodiments, the methods disclosed herein comprise measuring the levels of the following analytes in the sample: asparagine, taurine, acisoga, 1-oleoylglycerol (18:1), cholesterol, 2-hydroxyhippurate (salicylurate), 6-oxopiperidine-2-carboxylic acid, propionylglycine (C3).

In some embodiments, the analytes are selected from the group consisting of valylleucine, isoleucylvaline, glutamine-leucine, X-12212, glucuronate, and glutamate. Thus, in some embodiments, the methods disclosed herein comprise measuring the levels of the following analytes in the sample: valylleucine, isoleucylvaline, glutamine-leucine, X-12212, glucuronate, and glutamate.

In some embodiments, the analytes are selected from the group consisting of glucose, gamma-glutamyl transferase, uric acid, low density lipoprotein cholesterol, triglycerides, lipoprotein (a) mass, alkaline phosphatase and apolipoprotein B. Thus, in some embodiments, the methods disclosed herein comprise measuring the levels of the following analytes in the sample: glucose, gamma-glutamyl transferase, uric acid, low density lipoprotein cholesterol, triglycerides, lipoprotein (a) mass, alkaline phosphatase and apolipoprotein B.

In some embodiments, the analytes are selected from the group consisting of glutamate, X-16132, isoleucylalanine, isoleucylphenylalanine, lipoprotein (a) mass, small dense low density lipoprotein cholesterol, X-12212. ADSGEGDFXAEGGGVR (SEQ ID NO: 1), glutamine. leucine, and threonylleucine. Thus, in some embodiments, the methods disclosed herein comprise measuring the levels of the following analytes in the sample: glutamate, X-16132, isoleucylalanine, isoleucylphenylalanine, lipoprotein (a) mass, small dense low density lipoprotein cholesterol, X-12212, ADSGEGDFXAEGGGVR (SEQ ID NO: 1), glutamine-leucine, and threonylleucine.

In some embodiments, the analytes are selected from the group consisting of CER22.1, HexCER18:1, TG15:0, SM16:0, CER20:0, DHC20:1, and CER18:0. Thus, in some embodiments, the methods disclosed herein comprise measuring the levels of the following analytes in the sample: CER22.1, HexCER18:1, TG15:0, SM16:0, CER20:0, DHC20:1, and CER18:0.

In some embodiments, the analytes are selected from the group consisting of CER20:0, apolipoprotein B, SM16:0, lipoprotein (a) mass, DHC20L1, alkaline phosphatase, and CER18:0. Thus, in some embodiments, the methods disclosed herein comprise measuring the levels of the following analytes in the sample: CER20:0, apolipoprotein B, SM16:0, lipoprotein (a) mass, DHC20L1, alkaline phosphatase, and CER18:0

In some embodiments, the analytes are selected from the group consisting of glutamate, X-16132, isoleucylalanine, Lipoprotein (a) mass, X-12212, and glutamine-leucine. Thus, in some embodiments, the methods disclosed herein comprise measuring the levels of the following analytes in the sample: glutamate, X-16132, isoleucylalanine, Lipoprotein (a) mass, X-12212, and glutamine-leucine.

In some embodiments, the analytes are selected from the group consisting of oleic2, N-terminal pro-brain natriuretic peptide, lipoprotein (a) mass, insulin, glycated hemoglobin A1C, cismontaotl, small dense low density lipoprotein cholesterol, behenic2, adiponectin, and gamma-glutamyl transferase. Thus, in some embodiments, the methods disclosed herein comprise measuring the levels of the following analytes in the sample: oleic2, N-terminal pro-brain natriuretic peptide, lipoprotein (a) mass, insulin, glycated hemoglobin A1C, cismontaotl, small dense low density lipoprotein cholesterol, behenic2, adiponectin, and gamma-glutamyl transferase.

In some embodiments, the analytes are selected from the group consisting of isoleucylalanine, glucuronate, glycine, isoleucylphenylalanine, mannose, X-21452, 1-oleoylglycerophosphoglycerol, X-21335, 7-methylxanthine, X-12729, acisoga, alpha-hydroxyisovaleroyl carnitine, 2-aminoadipate, X-18914, tigloylglycine, and pyridoxal. Accordingly, in some embodiments, the methods disclosed herein comprise measuring the levels of the following analytes in the sample: isoleucylalanine, glucuronate, glycine, isoleucylphenylalanine, mannose, X-21452, 1-oleoylglycerophosphoglycerol, X-21335, 7-methylxanthine, X-12729, acisoga, alpha-hydroxyisovaleroyl carnitine, 2-aminoadipate, X-18914, tigloylglycine, and pyridoxal.

In some embodiments, the analytes are selected from the group consisting of isoleucylalanine, glycine, isoleucylphenylalanine, oleic2, X-21335, methylxanthine, aminoadipate, mannose, acisoga, arachidonoyl.GPE.20.4, and triglycerides. Accordingly, in some embodiments, the methods disclosed herein comprise measuring the levels of the following analytes in the sample: isoleucylalanine, glycine, isoleucylphenylalanine, oleic2, X-21335, methylxanthine, aminoadipate, mannose, acisoga, arachidonoyl.GPE.20.4, and triglycerides In some embodiments, the analytes are selected from the group consisting of DHC18:0, DG18:1n9, total diacylglycerol, TG20:3n9, CE20:4n6, CER18:1, DHC20:1, CE18:2n6, PL18:2n6, SM18:0, FA14:1n5, PL15:0, and CE16:0. Accordingly, in some embodiments, the methods disclosed herein comprise measuring the levels of the following analytes in the sample: DHC18:0, DG18:1n9, total diacylglycerol, TG20:3n9, CE20:4n6, CER18:1, DHC20:1, CE18:2n6, PL18:2n6, SM18:0, FA14:1n5, PL15:0, and CE16:0.

In some embodiments, the analytes are selected from the group consisting of glycated hemoglobin A1C, total diacylglycerol, cismontotl, lipoprotein (a) mass, TG20.3n9, oleic2, DHC18.1, N-terminal pro-brain natriuretic peptide, gamma-glutamyl transferase, and CER18. Accordingly, in some embodiments, the methods disclosed herein comprise measuring the levels of the following analytes in the sample: glycated hemoglobin A1C, total diacylglycerol, cismontotl, lipoprotein (a) mass, TG20.3n9, oleic2, DHC18.1, N-terminal pro-brain natriuretic peptide, gamma-glutamyl transferase, and CER18.

In some embodiments, the analytes are selected from the group consisting of isoleucylalanine, glycine, cismontotl, lipoprotein (a) mass, X-21452, isoleucylphenylalanine, glycated hemoglobin A1C, X-21335, X7.methylxanthine, acisoga and X-12729. Accordingly, in some embodiments, the methods disclosed herein comprise measuring the levels of the following analytes in the sample: isoleucylalanine, glycine, cismontotl, lipoprotein (a) mass, X-21452, isoleucylphenylalanine, glycated hemoglobin A1C, X-21335, X7.methylxanthine, acisoga and X-12729.

Thus, in a representative embodiment, the disclosure provides a method for evaluating a subject for having ASCAD or as having a coronary atherosclerotic plaque in a subject, the method comprising (a) obtaining a plasma or serum sample from a human subject; (b) determining the amount of each analyte from a panel of analyte biomarkers; (c) comparing the relative amount of the analytes in the biological sample with the relative amount of the analytes in a control sample; and (d) determining the probability the subject has atherosclerotic coronary artery disease or a coronary atherosclerotic plaque if the relative amount of the analytes in the biological sample are increased or decreased relative to the amount of the analytes in a control sample.

In one aspect, the disclosure provides a method for evaluating a subject for having atherosclerotic coronary artery disease (ASCAD) or as having a coronary atherosclerotic plaque in a subject, the method comprising measuring the level of each analyte within a selected panel of analyte biomarkers in a biological sample obtained from a subject. In some embodiments, the method measuring the level of one or more analytes from a panel of analyte biomarkers, wherein the panel of analyte biomarkers is selected from the group consisting of:
(i) valylleucine, glutamate, acisoga, urate, glucuronate, fucose, butyrylcarnitine (C4), mannose;
(ii) acisoga, o-cresol sulfate, threonate, cysteine-glutathione disulfide;
(iii) N-acetylphenylalanine, N-acetylleucine, valylleucine, xylitol, 2-hydroxyhippurate (salicylurate), glycylphenylalanine, serylleucine, fucose;
(iv) glutamate, acisoga, valylleucine, mannose, glucuronate, urate, valerylcarnitine (C5), 12-HETE;
(v) o-cresol sulfate, acisoga, cysteine-glutathione disulfide, glucose, 1-nonadecanoylglycerophosphocholine (19:0), threonate;
(vi) N-acetylphenylalanine, N-acetylleucine, glycylphenylalanine, valylleucine, xylitol, 12-HETE, 2-hydroxyhippurate (salicylurate);
(vii) N-acetylthreonine, tigloylglycine, glycerate, valerylcarnitine (C5), threonate, 2-hydroxyhippurate (salicylurate), salicylate, tartronate (hydroxymalonated);
(viii) N-acetylglycine, 3-ethylphenylsulfate;
(viv) serotonin (5HT), N-acetylputrescine, leucylleucine, propionylglycine (C3), cholate, glycocholenate sulfate, asparagine, 3-ethylphenylsulfate;
(x) acisoga, mannose, valerylcarnitine (C5), 1-linoleoyl-GPE (18.2), glycoursodeoxycholate, threonate, 2-hydroxyhippurate (salicylurate), salicylate;
(xi) N-acetylglycine, threonate, 2-hydroxyhippurate (salicylurate), 3-ethylphenylsulfate, salicylate;
(xii) asparagine, taurine, acisoga, 1-oleoylglycerol (18:1), cholesterol, 2-hydroxyhippurate (salicylurate), 6-oxopiperidine-2-carboxylic acid, propionylglycine (C3)

In some embodiments, analysis of any of the panels take into account the age and/or gender of the subject.

In one aspect, the disclosure provides a method for evaluating a subject for having atherosclerotic coronary artery disease (ASCAD) or as having a coronary atherosclerotic plaque in a subject, the method comprising measuring the level of each analyte within a selected panel of analyte biomarkers in a biological sample obtained from a subject. In some embodiments, the method measuring the level of one or more analytes from a panel of analyte biomarkers, wherein the panel of analyte biomarkers is selected from the group consisting of
(xiii) linoleic2, Lipoprotein (a) cholesterol, Apolipoprotein B, Alkaline phosphatase, Lipoprotein (a) mass, MHDM2, B-Sitosterol, Campesterol, Lipoprotein (a) mass, Gamma-glutamyl transferasepalmleic2, Glucose, ProInsulin, cholesterol, Fish Oil, High Sensitive C Reactive Protein, Small dense Low Density Lipoprotein Cholesterol, Uric acid, Low Density Lipoprotein Cholesterol, Insulin, Triglycerides, and Vitamin D;
(xiv) 1-myristoylglycerol (14:0), glycerol 3-phosphate (G3P), serylleucine, 1-nonadecanoylglycerophosphocholine (19:0), glycine, theobromine, 1-oleoylglycerol (18:1), glycyltryptophan, threonate, 1-oleoylglycerophosphoglycerol, guanidinosuccinate, threonylleucine, 1-oleoyl-GPC (18:1), histidylphenylalanine, tigloylglycine, 1-stearoylglycerophosphoglycerol, hydroxybutyrylcarnitine, tryptophylphenylalanine, 2-aminooctanoate, imidazole lactate, urate, 2-arachidonoyl-GPE (20:4), imidazole propionate, valylglycine, 2-docosahexaenoylglycerophoethanolamine, indolepropionate, valylisoleucine, 2-hydroxybutyrate (AHB), isobutyrylglycine (C4), valylleucine, 2prime-deoxyuridine, isoleucylalanine, X-12212, 3 7-dimethylurate, isoleucylglycine, X-12472, 3-ethylphenylsulfate, isoleucylisoleucine, X-12524, 3-hydroxy-2-ethylpropionate, isoleucylleucine, X-12544, 3-methyl-2-oxobutyrate, isoleucylphenylalanine, X-12824, 3-methylglutarylcarnitine-1, isoleucylvaline, X-14056, 3-methylxanthine, leucylglycine, X-14291, 4-hydroxyphenylacetate, leucylserine, X-15245, 7-methylurate, mannose, X-16129, 7-methylxanthine, methyl glucopyranoside (alpha+beta), X-16132, acisoga, methyl indole-3-acetate, X-17178, ADSGEGDFXAEGGGVR (SEQ ID NO: 1), N2 N2-dimethylguanosine, X-21289, alpha-glutamyltyrosine, N4-acetylcytidine, X-21335, alpha-hydroxyisovaleroyl carnitine, N-acetylalanine, X-21365, alpha-ketobutyrate, N-acetyl-beta-alanine, X-21452, alpha-ketoglutarate, N-acetylputrescine, X-21626, asparagine, N-acetylthreonine, X-21662, carnitine, N-acetylvaline, xanthine, 1-myristoylglycerol (14:0), glycerol 3-phosphate (G3P), serylleucine, 1-nonadecanoylglycerophosphocholine (19:0), glycine, theobromine, 1-oleoylglycerol (18:1), glycyltryptophan, threonate, 1-oleoylglycerophosphoglycerol, guanidinosuccinate, threonylleucine, 1-oleoyl-GPC (18:1), hi stidylphenylalanine, tigloylglycine, 1-stearoylglycerophosphoglycerol, hydroxybutyrylcarnitine, tryptophylphenylalanine, 2-aminooctanoate, imidazole, lactate, and urate;

(xv) CE16:1n7, DG16:0, DHC20:1, HexCER16:0, SM16:0, CE18:2n6, DG18:0, DHC24:0, HexCER18:1, SM20:1, CE20:4n6, DG18:1n9, DHC24:1, LacCER16:0, TG15:0, CER18:0, DG20:3n9, FA18:3n6, PL15:0, TG16:0, CER20:0, DHC18:0, FA20:3n6, PLdm16:0, total Triacylglycerol. CER22:1, DHC18:1, HexCER14:0, and PLdm18:1n9;

(xvi) Glycated hemoglobin A1C, Lipoprotein (a) mass, nervonic2, B-Sitosterol, Adiponectin, Triglycerides, Omega 6 total, behenic2, Campesterol, N-terminal probrain natriuretic peptide, oleic2, Desmosterol, palmleic2, cismontotl, Gamma-glutamyl transferase, ProInsulin, Glucose, Small dense Low Density Lipoprotein Cholesterol, transpalm2, High Density Lipoprotein Cholesterol, Uric acid, High Density Lipoprotein Fraction 3, Insulin, Vitamin D, linoleic2, Lipoprotein (a) cholesterol, and MHDM2;

(xvii) 1-3-dimethylurate, glycerol 3-phosphate (G3P), pyroglutamylglutamine, 1 7-dimethylurate, glycine, pyroglutamylglycine, 12-HETE, glycylphenylalanine, pyruvate, 1-linoleoyl-GPE (18:2), glycyltryptophan, S-adenosylhomocysteine (SAH), 1-methylurate, guanidinosuccinate, salicylate, 1-nonadecanoylglycerophosphocholine (19:0), hexanoylcarnitine (C6), serylleucine, 1-oleoylglycerol (18:1), hi stidylphenylalanine, succinylcarnitine (C4), 1-oleoylglycerophosphoglycerol, homostachydrine, threonate, 2-aminoadipate, hydroxybutyrylcarnitine, threonylleucine, 2-aminobutyrate, imidazole propionate, thymol sulfate, 2-aminooctanoate, indolepropionate, tigloylglycine, 2-arachidonoyl-GPE (20:4), isobutyrylglycine (C4), tryptophylglycine, 2-docosahexaenoylglycerophosphoethanolamine, isoleucylalanine, tryptophylphenylalanine, 2-hydroxybutyrate (AHB), isoleucylglycine, tyrosylglutamine, 2-hydroxyhippurate (salicylurate), isoleucylisoleucine, urate, 2-linoleoyl-GPE (18:2), isoleucylleucine, valerylcarnitine (C5), 2prime-deoxyuridine, isoleucylphenylalanine, valylglycine, 3-ethylphenylsulfate, isovalerylglycine, valylisoleucine, 3-hydroxyisobutyrate, kynurenine, valylleucine, 3-methyl-2-oxobutyrate, leucylaspartate, valylvaline, 3-methylglutarylcarnitine-1, leucylglycine, X-11429, 3-methylglutarylcarnitine-2, leucylserine, X-11444, 3-methylxanthine, lysylleucine, X-11787, 4-hydroxyphenylacetate, mannose, X-11945, 5alpha-androstan-3beta 17beta-diol monosulfate 2, methyl glucopyranoside (alpha+beta), X-12212, 7-methylurate, methyl indole-3-acetate, X-12472, 7-methylxanthine, N2 N2-dimethylguanosine, X-12729, acetylcarnitine (C2), N4-acetylcytidine, X-12824, acisoga, N6-carbamoylthreonyladenosine, X-14056, AD SGEGDFXAE-GGGVR, N-acetylalanine, X-15245, alpha-glutamyltyrosine, N-acetylglycine, X-15492, alpha-hydroxyisovaleroyl carnitine, N-acetylisoleucine, X-16129, alpha-ketobutyrate, N-acetylneuraminate, X-16132, alpha-ketoglutarate, N-acetylthreonine, X-17178, beta-tocopherol, N-acetylvaline, X-17690, butyrylcarnitine (C4), N-methyl proline, X-18914, carnitine, octanoylcarnitine (C8), X-18922, cysteine-glutathione disulfide, oleic ethanolamide, X-19438, cytidine, O-sulfo-L-tyrosine, X-21289, fucose, phenylalanylaspartate, X-21335, gamma-glutamylisoleucine, prolylphenylalanine, X-21365, gamma-glutamylvaline, propionylcarnitine (C3), X-21367, glucose, propionylglycine (C3), X-21452, glucuronate, pseudouridine, X-21471, glutamate, pyridoxal, X-21626, glutamine-leucine, pyridoxate, and xanthine; and (xvii) CE16:0, DG18:0, DHC18:1, DHC26:1, PL24:0, CE16:1n7, DG18:1n9, DHC20:0, FA14:1n5, SM18:0, CE18:1n9, DG20:0, DHC20:1, PL15:0, TG15:0, CE18:2n6, DG20:2n6, DHC22:1, PL18:2n6, TG20:3n9, CE20:4n6, DG20:3n9, DHC24:1, PL20:3n9, Total Diacylglycerol, CER18:0, DHC18:0, DHC26:0, PL20:4n6, Total Triacylglycerol, and CER18:1.

The term "determining the amount of each analyte" as used herein refers to determining at least one characteristic feature of at least one metabolite comprised by the sample referred to herein. Characteristic features in accordance with the present invention are features which characterize the physical and/or chemical properties including biochemical properties of a metabolite. Such properties include, e.g., molecular weight, viscosity, density, electrical charge, spin, optical activity, elementary composition, chemical structure, capability to react with other compounds, capability to elicit a response in a biological read out system (e.g., induction of a reporter gene) and the like. Values for said properties may serve as characteristic features and can be determined by techniques well known in the art. Moreover, the characteristic feature may be any feature which is derived from the values of the physical and/or chemical properties of a metabolite by standard operations, e.g., mathematical calculations such as multiplication, division, gradient boosting, generalized linear modeling, or logarithmic calculus. Most preferably, the at least one characteristic feature allows the determination and/or chemical identification of the said at least one metabolite.

The analytes comprised by a biological sample may be determined in accordance with the present invention quantitatively or qualitatively. For qualitative determination, the presence or absence of the metabolite will be determined by a suitable technique. Moreover, qualitative determination may, preferably, include determination of the chemical structure or composition of the metabolite. For quantitative determination, either the precise amount of the analyte(s) present in the biological sample will be determined or the relative amount of the analyte(s) will be determined, preferably, based on the value determined for the characteristic feature(s) referred to herein above. The relative amount may be determined in a case were the precise amount of a metabolite can or shall not be determined. In said case, it can be determined whether the amount in which the analyte(s) is present is increased or decreased with respect to a second sample comprising said analyte(s) in a second amount. Quantitatively analyzing an analyte(s), thus, also includes what is sometimes referred to as semi-quantitative analysis of a metabolite.

Typically, the analyte level is determined by measuring the level of the metabolite in a body fluid (clinical sample), e.g., blood, serum, plasma, or urine. The level can be determined by, for example, mass spectrometry (MS), ELISA, immunoassays, enzymatic assays, spectrophotometry, colorimetry, fluorometry, bacterial assays, compound separation techniques, or other known techniques for determining the presence and/or quantity of an analyte.

Compound separation techniques yield a time resolved separation of the analytes comprised by the sample. Suitable techniques for separation to be used include, for example, all chromatographic separation techniques such as liquid chromatography (LC), high performance liquid chromatography (HPLC), gas chromatography (GC), thin layer chromatography, size exclusion or affinity chromatography. These techniques are well known in the art and can be applied by the person skilled in the art. In some embodiments, the methods utilize LC and/or GC chromatographic techniques including, for example, gas chromatography mass spectrometry (GC-MS), liquid chromatography mass spectrometry (LC-MS), liquid chromatography-tandem mass spectrometry (UPLC-MS/MS), direct infusion mass spectrometry or Fourier transform ion-cyclotrone-resonance mass spectrometry (FT-ICR-MS), capillary electrophoresis mass spectrometry (CE-MS), high-performance liquid chromatography coupled mass spectrometry (HPLC-MS), quadrupole mass spectrometry, any sequentially coupled mass spectrometry, such as MS-MS or MS-MS-MS, inductively coupled plasma mass spectrometry (ICP-MS), pyrolysis mass spectrometry (Py-MS), ion mobility mass spectrometry or time of flight mass spectrometry (TOF). In some embodiments, LC-MS and/or GC-MS. As an alternative or in addition to mass spectrometry techniques, the following techniques may be used for compound determination: nuclear magnetic resonance (NMR), magnetic resonance imaging (MM), Fourier transform infrared analysis (FT-IR), ultra violet (UV) spectroscopy, refraction index (RI), fluorescent detection, radiochemical detection, electrochemical detection, light scattering (LS), dispersive Raman spectroscopy or flame ionization detection (FID). These techniques are well known to the person skilled in the art and can be applied without further ado. In some embodiments, the methods disclosed herein shall be, optionally, assisted by automation. For example sample processing or pre-treatment can be automated by robotics. Data processing and comparison can be assisted by suitable computer programs and databases. Automation as described herein allows using the method of the present invention in high-throughput approaches.

"Determining" methods include, for example, sending a clinical sample(s) to a commercial laboratory for measurement or the use of commercially available assay kits. Commercially available assay kits are known in the art. For example, Quest Diagnostics, Sigma Aldrich, CATACHEM Inc., Eton Bioscience Inc., and Bio Vision Research Products are exemplary suppliers of such assays. Exemplary kits and suppliers will be apparent to the skilled artisan.

In some cases, the methods disclosed herein involve comparing levels or occurrences to a reference. The reference can take on a variety of forms. In some cases, the reference comprises predetermined values for the plurality of analytes (e.g., each of the plurality of analytes). The predetermined value can take a variety of forms. It can be a level or occurrence of an analyte obtained from a subject known to have atherosclerotic CAD or to have a coronary atherosclerotic plaque (e.g., a symptomatic subject), or obtained from a subject known not to suffer from atherosclerotic CAD or known to not have a coronary atherosclerotic plaque (e.g., an asymptomatic subject). It can be a level or occurrence of an analyte obtained from a subject having no previous history of coronary artery disease. It can be a level or occurrence in the same subject, e.g., at a different time point. A predetermined value that represents a level(s) of an analyte is referred to herein as a predetermined level. A predetermined level can be single cut-off value, such as a median or mean. It can be a range of cut-off (or threshold) values, such as a confidence interval. It can be established based upon comparative groups, such as where the risk in one defined group is a fold higher, or lower, (e.g., approximately 2-fold, 4-fold, 8-fold, 16-fold or more) than the risk in another defined group. It can be a range, for example, where a population of subjects (e.g., control subjects) is divided equally (or unequally) into groups, such as a low-risk group, a medium-risk group and a high-risk group, or into quartiles, the lowest quartile being subjects with the lowest risk and the highest quartile being subjects with the highest risk, or into n-quantiles (i.e., n regularly spaced intervals) the lowest of the n-quantiles being subjects with the lowest risk and the highest of the n-quantiles being subjects with the highest risk. Moreover, the reference could be a calculated reference, most preferably the average or median, for the relative or absolute amount of an analyte of a population of individuals comprising the subject to be investigated. The absolute or relative amounts of the analytes of said individuals of the population can be determined as specified elsewhere herein. How to calculate a suitable reference value, preferably, the average or median, is well known in the art. The population of subjects referred to before shall comprise a plurality of subjects, preferably, at least 5, 10, 50, 100, 1,000 subjects. It is to be understood that the subject to be diagnosed by the method of the present invention and the subjects of the said plurality of subjects are of the same species.

Subjects associated with predetermined values are typically referred to as control subjects (or controls). A control subject does not have atherosclerosis or atherosclerotic CAD. In some cases it may be desirable that control subject is a symptomatic subject, and in other cases it may be desirable that a control subject is an asymptomatic subject. Thus, in some cases the level of an analyte in a subject being greater than or equal to the level of the analyte in a control subject is indicative of a clinical status (e.g., indicative of CAD diagnosis). In other cases the level of an analyte in a subject being less than or equal to the level of the analyte in a control subject is indicative of a clinical status. More generally, the combination of raised and lowered levels of a predefined group of analytes is indicative of clinical status. The amount of the greater than and the amount of the less than is usually of a sufficient magnitude to, for example, facilitate distinguishing a subject from a control subject using the disclosed methods. Typically, the greater than, or the less than, that is sufficient to distinguish a subject from a control subject is a statistically significant greater than, or a statistically significant less than. In cases where the level of an analyte in a subject being equal to the level of the metabolite in a control subject is indicative of a clinical status, the "being equal" refers to being approximately equal (e.g., not statistically different).

The predetermined value can depend upon a particular population of subjects (e.g., human subjects) selected. For example, an apparently healthy population will have a different 'normal' range of metabolites than will a population of subjects which have, or are likely to have, atherosclerotic CAD or a coronary atherosclerotic plaque. Accordingly, the predetermined values selected may take into account the category (e.g., healthy, at risk, diseased, age, gender, etc.) in which a subject (e.g., human subject) falls. Appropriate ranges and categories can be selected with no more than routine experimentation by those of ordinary skill in the art. In some cases a predetermined value of a biomarker is a value that is the average for a population of healthy subjects (human subjects) (e.g., human subjects who have no apparent signs and symptoms of CAD). The predetermined value will depend, of course, on the particular analyte (biomarker) selected and even upon the characteristics of the population in which the subject lies. In characterizing likelihood, or risk, numerous predetermined values can be established.

A level, in some embodiments, may itself be a relative level that reflects a comparison of levels between two states. Relative levels that reflect a comparison (e.g., ratio, difference, logarithmic difference, percentage change, etc.) between two states (e.g., healthy and diseased) may be referred to as delta values. The use of relative levels is beneficial in some cases because, to an extent, they exclude measurement related variations (e.g., laboratory personnel, laboratories, measurements devices, reagent lots/preparations, assay kits, etc.). However, the invention is not so limited.

Analyte levels and/or reference levels may be stored in a suitable data storage medium (e.g., a database) and are, thus, also available for future diagnoses. This also allows efficiently diagnosing prevalence for a disease because suitable reference results can be identified in the database once it has been confirmed (in the future) that the subject from which the corresponding reference sample was obtained did have CAD or a coronary atherosclerotic plaque. As used herein a "database" comprises data collected (e.g., analyte and/or reference level information and/or patient information) on a suitable storage medium. Moreover, the database, may further comprise a database management system. The database management system is, preferably, a network-based, hierarchical or object-oriented database management system. More preferably, the database will be implemented as a distributed (federal) system, e.g. as a Client-Server-System. More preferably, the database is structured as to allow a search algorithm to compare a test data set with the data sets comprised by the data collection. Specifically, by using such an algorithm, the database can be searched for similar or identical data sets being indicative of atherosclerotic CAD or a coronary atherosclerotic plaque (e.g. a query search). Thus, if an identical or similar data set can be identified in the data collection, the test data set will be associated with atherosclerotic CAD or coronary atherosclerotic plaques. Consequently, the information obtained from the data collection can be used to diagnose CAD or based on a test data set obtained from a subject. More preferably, the data collection comprises characteristic values of all analytes comprised by any one of the groups recited above.

In some embodiments, the methods disclosed herein further comprise modifying the subject's clinical record to identify the subject as having or as not having atherosclerotic coronary artery disease, or as having or as not having a coronary atherosclerotic plaque. The clinical record may be stored in any suitable data storage medium (e.g., a computer readable medium).

The invention also may provide kits for evaluating analyte biomarkers in a subject. The kits of the invention can take on a variety of forms. Typically, the kits will include reagents suitable for determining levels of a plurality of analytes biomarkers (e.g., those disclosed herein) in a sample. Optionally, the kits may contain one or more control samples. Typically, a comparison between the levels of the biomarkers in the subject and levels of the biomarkers in the control samples is indicative of a clinical status (e.g., diagnosis or likelihood of having atherosclerotic CAD or as having a coronary atherosclerotic plaque). Also, the kits, in some cases, will include written information (indicia) providing a reference (e.g., predetermined values), wherein a comparison between the levels of the biomarkers in the subject and the reference (predetermined values) is indicative of a clinical status. In some cases, the kits comprise software useful for comparing biomarker levels or occurrences with a reference (e.g., a prediction model). Usually the software will be provided in a computer readable format such as a compact disc, but it also may be available for downloading via the internet. However, the kits are not so limited and other variations with will be apparent to one of ordinary skill in the art.

The present methods can also be used for selecting a treatment and/or determining a treatment plan for a subject, based on the occurrence or levels of certain analytes relevant to CAD. In some embodiments, using the method disclosed herein, a health care provider (e.g., a physician) identifies a subject as having or at risk of having for having atherosclerotic CAD or as having a coronary atherosclerotic plaque and, based on this identification the health care provider determines an adequate management plan for the subject. In some embodiments, using the method disclosed herein, a health care provider (e.g., a physician) diagnoses a subject as having a atherosclerotic CAD or as having a coronary atherosclerotic plaque based on the occurrence or levels of certain analytes in a clinical sample obtained from the subject, and/or based on a classification of a clinical sample obtained from the subject. By way of this diagnosis the health care provider determines an adequate treatment or treatment plan for the subject. In some embodiments, the methods further include administering the treatment to the subject.

In some embodiments, the invention relates to identifying subjects who are likely to have successful treatment with a particular drug dose, formulation and/or administration modality. Other embodiments include evaluating the efficacy of a drug using the metabolomic profiling methods of the present invention. In some embodiments, the metabolomic profiling methods are useful for identifying subjects who are likely to have successful treatment with a particular drug or therapeutic regiment. For example, during a study (e.g., a clinical study) of a drug or treatment, subjects who have a CAD or coronary atherosclerotic plaque may respond well to the drug or treatment, and others may not. Disparity in treatment efficacy is associated with numerous variables, for example genetic variations among the subjects. In some embodiments, subjects in a population are stratified based on the metabolomic profiling methods disclosed herein. In some embodiments, resulting strata are further evaluated based on various epidemiological, and or clinical factors (e.g., response to a specific treatment). In some embodiments, stratum, identified based on a metabolic profile, reflect a subpopulation of subjects that response predictably (e.g., have a predetermined response) to certain treatments. In further embodiments, samples are obtained from subjects who have been subjected to the drug being tested and who have a predetermined response to the treatment. In some cases, a reference can be established from all or a portion of the analytes from these samples, for example, to provide a reference metabolic profile. A sample to be tested can then be evaluated (e.g., using a prediction model) against the reference and classified on the basis of whether treatment would be successful or unsuccessful. A company and/or person testing a treatment (e.g., compound, drug, and lifestyle change) could discern more accurate information regarding the types or subtypes of CAD for which a treatment is most useful. This information also aids a healthcare provider in determining the best treatment plan for a subject.

In some embodiments, treatment for the atherosclerotic CAD or coronary atherosclerotic plaques is to administer to the subject a composition comprising an effective amount of at therapeutic agent and/or to instruct the subject to adopt at least one therapeutic lifestyle change (e.g., change in diet or exercise). Therapeutic compounds suitable for treating CAD or coronary atherosclerotic plaques are well known in the art and some are disclosed herein. Non-limiting examples include statins, cholesterol absorption inhibitors, niacin-derivatives, omega-3-fatty acid compounds, bile acid sequestrants, PCSK9 antagonists, anti-platelet agents and aspirin. Appropriate lifestyle changes to improve cardiovascular health are also well known in the art. Non-limiting examples include increased physical activity, caloric intake restriction, nutritional meal planning, and weight reduction. However, the invention is not so limited and other appropriate treatments will be apparent to one of ordinary skill in the art.

When a therapeutic agent or other treatment is administered, it is administered in an amount effective to treat CAD or reduce the likelihood (or risk) of future CAD or CAD events. An effective amount is a dosage of the therapeutic agent sufficient to provide a medically desirable result. The effective amount will vary with the particular condition being treated, the age and physical condition of the subject being treated, the severity of the condition, the duration of the treatment, the nature of the concurrent therapy (if any), the specific route of administration and the like factors within the knowledge and expertise of the health care practitioner. For example, an effective amount can depend upon the degree to which a subject has abnormal levels of certain analytes (e.g., analytes as described herein) that are indicative of atherosclerotic CAD or a coronary atherosclerotic plaque. It should be understood that the therapeutic agents of the invention are used to treat and/or prevent atherosclerotic CAD or a coronary atherosclerotic plaque. Thus, in some cases, they may be used prophylactically in human subjects at risk of developing an atherosclerotic CAD or a coronary atherosclerotic plaque. Thus, in some cases, an effective amount is that amount which can lower the risk of, slow or perhaps prevent altogether the development of atherosclerotic CAD or a coronary atherosclerotic plaque. It will be recognized when the therapeutic agent is used in acute circumstances, it is used to prevent one or more medically undesirable results that typically flow from such adverse events. Methods for selecting a suitable treatment and an appropriate dose thereof will be apparent to one of ordinary skill in the art.

The invention further provides for the communication of assay results or diagnoses or both to technicians, physicians or patients, for example. In certain embodiments, computers will be used to communicate assay results or diagnoses or both to interested parties, e.g., physicians and their patients. In some instances, the methods further comprise providing communicating the patient status (i.e. as having or not having ASCAD or the presence or absence of a coronary atherosclerotic plaque) as a report. Thus, in some instances, the subject methods may further include a step of generating or outputting a report providing the results of the subject methods, which report can be provided in the form of an electronic medium (e.g., an electronic display on a computer monitor), or in the form of a tangible medium (e.g., a report printed on paper or other tangible medium). Any form of report may be provided, e.g. as known in the art. In some embodiments of the invention, a diagnosis based on the presence or absence in a test subject of any the biomarkers of Tables 30, 32, 34, 36, 38, 40, 42, 44, 46, 48 or 50 is communicated to the subject as soon as possible after the diagnosis is obtained. The diagnosis may be communicated to the subject by the subject's treating physician. Alternatively, the diagnosis may be sent to a test subject by email or communicated to the subject by phone. The diagnosis may be sent to a test subject by in the form of a report. A computer may be used to communicate the diagnosis by email or phone. In certain embodiments, the message containing results of a diagnostic test may be generated and delivered automatically to the subject using a combination of computer hardware and software which will be familiar to artisans skilled in telecommunications.

A "report," as described herein, is an electronic or tangible document which includes report elements that provide information of interest relating to a diagnosis assessment, a prognosis assessment, a treatment assessment, a monitoring assessment, etc. and its results. A subject report can be completely or partially electronically generated. A subject report includes at least a subject assessment, e.g., a diagnosis as to whether a subject has a high likelihood of having ASCAD or as having a coronary atherosclerotic plaque; or a prognosis assessment, e.g. a prediction of the responsiveness of a patient to therapy; and/or a suggested course of treatment to be followed. A subject report can further include one or more of: 1) information regarding the testing facility; 2) service provider information; 3) subject data; 4) sample data; 5) an assessment report, which can include various information including: a) test data, where test data can include i) the biomarker levels of one or more biomarkers; and/or ii) the biomarker signatures for one or more panel of biomarkers described herein.

The report may include information about the testing facility, which information is relevant to the hospital, clinic, or laboratory in which sample gathering and/or data generation was conducted. This information can include one or more details relating to, for example, the name and location of the testing facility, the identity of the lab technician who conducted the assay and/or who entered the input data, the date and time the assay was conducted and/or analyzed, the location where the sample and/or result data is stored, the lot number of the reagents (e.g., kit, etc.) used in the assay, and the like. Report fields with this information can generally be populated using information provided by the user.

The report may include information about the service provider, which may be located outside the healthcare facility at which the user is located, or within the healthcare facility. Examples of such information can include the name and location of the service provider, the name of the reviewer, and where necessary or desired the name of the individual who conducted sample gathering and/or data generation. Report fields with this information can generally be populated using data entered by the user, which can be selected from among pre-scripted selections (e.g., using a drop-down menu). Other service provider information in the report can include contact information for technical information about the result and/or about the interpretive report.

The report may include a subject data section, including subject medical history as well as administrative subject data (that is, data that are not essential to the diagnosis, prognosis, or treatment assessment) such as information to identify the subject (e.g., name, subject date of birth (DOB), gender, mailing and/or residence address, medical record number (MRN), room and/or bed number in a healthcare facility), insurance information, and the like), the name of the subject's physician or other health professional who ordered the susceptibility prediction and, if different from the ordering physician, the name of a staff physician who is responsible for the subject's care (e.g., primary care physician).

The report may include a sample data section, which may provide information about the biological sample analyzed, such as the source of biological sample obtained from the subject (e.g. blood, e.g., whole blood, fractionated blood, plasma, serum, etc.), how the sample was handled (e.g. storage temperature, preparatory protocols) and the date and time collected. Report fields with this information can generally be populated using data entered by the user, some of which may be provided as pre-scripted selections (e.g., using a drop-down menu).

It will also be readily appreciated that the reports can include additional elements or modified elements. For example, where electronic, the report can contain hyperlinks which point to internal or external databases which provide more detailed information about selected elements of the report. For example, the patient data element of the report can include a hyperlink to an electronic patient record, or a site for accessing such a patient record, which patient record is maintained in a confidential database. This latter embodiment may be of interest in an in-hospital system or in-clinic setting. When in electronic format, the report is recorded on a suitable physical medium, such as a computer readable medium, e.g., in a computer memory, zip drive, CD, DVD, flash drive, etc.

It will be readily appreciated that the report can include all or some of the elements above, with the proviso that the report generally includes at least the elements sufficient to provide the analysis requested by the user (e.g., a diagnosis, a prognosis, or a prediction of responsiveness to a therapy).

The methods described herein may be used on samples collected from patients in a clinical trial and the results of the test used in conjunction with patient outcomes in order to determine whether subgroups of patients are more or less likely to show a response to a new drug than the whole group or other subgroups. Further, such methods can be used to identify from clinical data the subsets of patients who can benefit from therapy. Additionally, a patient is more likely to be included in a clinical trial if the results of the test indicate a higher likelihood that the patient will be responsive to medical treatment, and a patient is less likely to be included in a clinical trial if the results of the test indicate a lower likelihood that the patient will be responsive to medical treatment.

The methods described herein can be used alone or in combination with other clinical methods for patient stratification known in the art to provide a diagnosis, a prognosis, or a prediction of responsiveness to therapy. For example, clinical parameters that are known in the art for diagnosing ASCAD may be incorporated into the ordinarily skilled artisan's analysis to arrive at an ovarian cancer assessment with the subject methods.

EXAMPLES

The invention is further described in the following examples, which do not limit the scope of the invention described in the claims.

The Genetic Loci and the Burden of Atherosclerotic Lesions study (GLOBAL; NCT01738828) is an international multi-center, prospective study, which enrolled 7526 patients (approximately half of whom are atherosclerotic CAD cases; the other half are without atherosclerotic CAD) who were referred for coronary CT angiography, for assessment of suspected coronary artery disease (CAD) at a total of 48 clinical sites. Previous genetic and genomic studies of CAD have used patient history of CAD or MI (myocardial infarction), or invasive coronary angiography in order to determine case/control status. In the GLOBAL study, cardiovascular CT is utilized, including non-contrast-enhanced coronary computerized tomography (CT), also known as coronary artery calcium (CAC) scoring, and secondly contrast-enhanced CT angiography (CTA). The increased sensitivity of this imaging technique for the detection of coronary plaque has been shown to allow the re-classification of controls as cases (sponsor's own data).

The following Examples describe statistical analyses of the pilot GLOBAL data, consisting of metabolomic data for 1096 patients from a total of 26 clinical sites. A subset of 748 patients made up the Discovery Set; a further 348 participants made up the Validation Set. The aims of the GLOBAL Pilot Discovery cohort were to assess preliminary detection of strong biomarker-associations for atherosclerosis, in patients phenotyped using advanced cardiac CT-based imaging.

Patients presenting for a CTA, for an assessment of possible CAD, were identified as potential study candidates and were screened for eligibility according to the study inclusion and exclusion criteria. Subjects were assessed for cardiovascular disease risk factors including gender, age, hypertension, hyperlipidemia, diabetes, and smoking, as well as a number of other conditions, and signed the appropriate Institutional Review Board-approved informed consent form. The general inclusion criteria were as follows (1) Ages 18-90; (2) White and of Non-Hispanic or Non-Latino origin; and (3) Referred for coronary CT angiography to evaluate presence of CAD. The general exclusion criteria were as follows: (1) Use of immunosuppressive or immunomodulatory therapy including any dose of systemic corticosteroids in the preceding 30 days (except if steroids were administered as pre-medication prior to contrast administration for CT scan within 24 hours); (2) Chemotherapy in the preceding year; (3) Major surgery in the preceding 2 months; (4) Blood or blood product transfusion in the preceding 2 months; (5) Subjects for whom coronary CT angiography is contra-indicated per institutional standard of care; (6) Subjects with previous coronary arterial revascularization (percutaneous coronary intervention (PCI) or coronary artery bypass graft (CABG)); (7) Subjects with atrial fibrillation/ flutter or frequent irregular or rapid heart rhythms, which occurred within the past 3 months; (8) Subjects with a pacemaker or implantable cardioverter-defibrillator implant; (9) Active congestive heart failure or the presence of known non-ischemic cardiomyopathy; and (10) Known genetic disorders of atherosclerosis, lipid or lipoprotein metabolism. The subjects must have met all of the general inclusion criteria to be enrolled in the study. If any of the general exclusion criteria were met, the subject was excluded from the study.

Each patient was characterized in terms of biomarkers by the application of the following methods: whole genome sequencing (WGS), whole genome methylation (WGM), whole blood based transcriptome sequencing (WTS), unbiased proteomics, unbiased metabolomics, unbiased lipidomics and lipoprotein proteomics. In addition, more conventional biomarkers were measured.

Sample Preparation: Metabolomics:

Samples were stored at −70° C. until processed. Sample preparation was carried out as described previously. (Evans A M, et. al., *Integrated, nontargeted ultrahigh performance liquid chromatography/electrospray ionization tandem mass spectrometry platform for the identification and relative quantification of the small-molecule complement of biological systems*. Anal Chem 2009; 81(16):6656-6667) Briefly, recovery standards were added prior to the first step in the extraction process for quality control purposes. To remove protein, dissociate small molecules bound to protein or trapped in the precipitated protein matrix, and to recover chemically diverse metabolites, proteins were precipitated with methanol under vigorous shaking for 2 min (Glen Mills Genogrinder 2000) followed by centrifugation. The resulting extract was divided into four fractions: one for analysis by ultra high performance liquid chromatography-tandem mass spectrometry (UPLC-MS/MS; positive mode), one for analysis by UPLC-MS/MS (negative mode), one for analysis by gas chromatography—mass spectrometry (GC-MS), and one sample is reserved for backup. Three types of controls were analyzed in concert with the experimental samples: samples generated from a pool of human plasma (extensively characterized by Metabolon, Inc.) served as technical replicate throughout the data set; extracted water samples served as process blanks; and a cocktail of standards spiked into every analyzed sample allowed instrument performance monitoring. Instrument variability was determined by calculating the median relative standard deviation (RSD) for the standards that are added to each sample prior to injection into the mass spectrometers (median RSD=5%; n=30 standards). Overall process variability was determined by calculating the median RSD for all endogenous metabolites (i.e., non-instrument standards) present in 100% of the pooled human plasma samples (median RSD=11%; n=610 metabolites). Experimental samples and controls were randomized across the platform run.

Mass Spectrometry Analysis.

Non-targeted MS analysis was performed at Metabolon, Inc. Extracts were subjected to either GC-MS or UPLC-MS/MS[7]. The chromatography was standardized and, once the method was validated no further changes were made. As part of Metabolon's general practice, all columns are purchased from a single manufacturer's lot at the outset of experiments. All solvents were similarly purchased in bulk from a single manufacturer's lot in sufficient quantity to complete all related experiments. For each sample, vacuum-dried samples were dissolved in injection solvent containing eight or more injection standards at fixed concentrations, depending on the platform. The internal standards were used both to assure injection and chromatographic consistency. Instruments were tuned and calibrated for mass resolution and mass accuracy daily. The UPLC-MS/MS platform utilized a Waters Acquity UPLC with Waters UPLC BEH C18-2.1× 100 mm, 1.7 μm columns and a Thermo Scientific Q-Exactive high resolution/accurate mass spectrometer interfaced with a heated electrospray ionization (HESI-II) source and Orbitrap mass analyzer operated at 35,000 mass resolution. The sample extract was dried then reconstituted in acidic or basic LC-compatible solvents, each of which contained eight or more injection standards at fixed concentrations to ensure injection and chromatographic consistency. One aliquot was analyzed using acidic, positive ion-optimized conditions and the other using basic, negative ion-optimized conditions in two independent injections using separate dedicated columns. Extracts reconstituted in acidic conditions were gradient eluted using water and methanol containing 0.1% formic acid, while the basic extracts, which also used water/methanol, contained 6.5 mM ammonium bicarbonate. The MS analysis alternated between MS and data-dependent MS2 scans using dynamic exclusion, and the scan range was from 80-1000 m/z.

The samples destined for analysis by GC-MS were dried under vacuum desiccation for a minimum of 18 hours prior to being derivatized under dried nitrogen using bistrimethyl-silyltrifluoroacetamide. Derivatized samples were separated on a 5% phenyldimethyl silicone column with helium as carrier gas and a temperature ramp from 60° to 340° C. within a 17-min period. All samples were analyzed on a Thermo-Finnigan Trace DSQ MS operated at unit mass resolving power with electron impact ionization and a 50-750 atomic mass unit scan range.

Compound Identification, Quantification, and Data Curation.

Metabolites were identified by automated comparison of the ion features in the experimental samples to a reference library of chemical standard entries that included retention time, molecular weight (m/z), preferred adducts, and in-source fragments as well as associated MS spectra and curated by visual inspection for quality control using software developed at Metabolon. (DeHaven C D, et. al., *Organization of GC/MS and LC/MS metabolomics data into chemical libraries*. J Cheminform 2010; 2(1):9) Identification of known chemical entities was based on comparison to metabolomic library entries of purified standards. Over 2,500 commercially available purified standard compounds have been acquired and registered into LIMS for distribution to both the LC/MS and GC/MS platforms for determination of their detectable characteristics. An additional 250 mass spectral entries have been created for structurally unnamed biochemicals, which have been identified by virtue of their recurrent nature (both chromatographic and mass spectral). These compounds have the potential to be identified by future acquisition of a matching purified standard or by classical structural analysis. Peaks were quantified using area-under-the-curve. Raw area counts for each metabolite in each sample were normalized to correct for variation resulting from instrument inter-day tuning differences by the median value for each run-day, therefore, setting the medians to 1.0 for each run. This preserved variation between samples but allowed metabolites of widely different raw peak areas to be compared on a similar graphical scale. Missing values are imputed with the observed minimum after normalization.

Sample Preparation: Lipidomics

TrueMass® Lipomic Panel.

Lipids were extracted in the presence of authentic internal standards by the method of Folch et al. using chloroform: methanol (2:1 v/v). For the separation of neutral lipid classes [FFA, TAG, DAG, CE], a solvent system consisting of petroleum ether/diethyl ether/acetic acid (80:20:1) was employed. Individual phospholipid classes within each extract [PC, PE] were separated using the Agilent Technologies 1100 Series LC. Each lipid class was transesterified in 1% sulfuric acid in methanol in a sealed vial under a nitrogen atmosphere at 100° C. for 45 minutes. The resulting fatty acid methyl esters were extracted from the mixture with hexane containing 0.05% butylated hydroxytoluene and prepared for GC by sealing the hexane extracts under nitrogen. Fatty acid methyl esters were separated and quantified by capillary GC (Agilent Technologies 6890 Series GC) equipped with a 30 m DB 88 capillary column (Agilent Technologies) and a flame ionization detector.

TrueMass® Ceramides Panel.

Deuterium-labelled internal standards were added to the samples and the mixture was solubilized in methanol followed by a crash extraction. A bilayer was formed with the addition of KCl in water, and the organic layer is removed and concentrated under nitrogen. The extract was spun, filtered, and split into 2 injections—one for ceramides and one for sphingosines. The extract was injected onto an Agilent C8 column connected to an Agilent 1290 Infinity LC and ABI 4000 QTRAP. The analytes were ionized via positive electrospray and the mass spectrometer was operated in the tandem MS mode. The absolute concentration of each sphingolipid was determined by comparing the peak to that of the relevant internal standard.

Mass Spectrometry Analysis.

Non-targeted MS analysis was performed at Metabolon, Inc. Extracts were subjected to either GC-MS or UPLC-MS/MS[7]. The chromatography was standardized and, once the method was validated no further changes were made. As part of Metabolon's general practice, all columns are purchased from a single manufacturer's lot at the outset of experiments. All solvents were similarly purchased in bulk from a single manufacturer's lot in sufficient quantity to complete all related experiments. For each sample, vacuum-dried samples were dissolved in injection solvent containing eight or more injection standards at fixed concentrations, depending on the platform. The internal standards were used both to assure injection and chromatographic consistency. Instruments were tuned and calibrated for mass resolution and mass accuracy daily. The UPLC-MS/MS platform utilized a Waters Acquity UPLC with Waters UPLC BEH C18-2.1× 100 mm, 1.7 µm columns and a Thermo Scientific Q-Exactive high resolution/accurate mass spectrometer interfaced with a heated electrospray ionization (HESI-II) source and Orbitrap mass analyzer operated at 35,000 mass resolution. The sample extract was dried then reconstituted in acidic or basic LC-compatible solvents, each of which contained eight or more injection standards at fixed concentrations to ensure injection and chromatographic consistency. One aliquot was analyzed using acidic, positive ion-optimized conditions and the other using basic, negative ion-optimized conditions in two independent injections using separate dedicated columns. Extracts reconstituted in acidic conditions were gradient eluted using water and methanol containing 0.1% formic acid, while the basic extracts, which also used water/methanol, contained 6.5 mM ammonium bicarbonate. The MS analysis alternated between MS and data-dependent MS2 scans using dynamic exclusion, and the scan range was from 80-1000 m/z.

The samples destined for analysis by GC-MS were dried under vacuum desiccation for a minimum of 18 hours prior to being derivatized under dried nitrogen using bistrimethyl-silyltrifluoroacetamide. Derivatized samples were separated on a 5% phenyldimethyl silicone column with helium as carrier gas and a temperature ramp from 60° to 340° C. within a 17-min period. All samples were analyzed on a Thermo-Finnigan Trace DSQ MS operated at unit mass resolving power with electron impact ionization and a 50-750 atomic mass unit scan range.

Compound Identification, Quantification, and Data Curation.

Metabolites were identified by automated comparison of the ion features in the experimental samples to a reference library of chemical standard entries that included retention time, molecular weight (m/z), preferred adducts, and in-source fragments as well as associated MS spectra and curated by visual inspection for quality control using software developed at Metabolon. (DeHaven et al.) Identification of known chemical entities was based on comparison to metabolomic library entries of purified standards. Over 2,500 commercially available purified standard compounds have been acquired and registered into LIMS for distribution to both the LC/MS and GC/MS platforms for determination of their detectable characteristics. An additional 250 mass spectral entries have been created for structurally unnamed biochemicals, which have been identified by virtue of their recurrent nature (both chromatographic and mass spectral). These compounds have the potential to be identified by future acquisition of a matching purified standard or by classical structural analysis. Peaks were quantified using area-under-the-curve. Raw area counts for each metabolite in each sample were normalized to correct for variation resulting from instrument inter-day tuning differences by the median value for each run-day, therefore, setting the medians to 1.0 for each run. This preserved variation between samples but allowed metabolites of widely different raw peak areas to be compared on a similar graphical scale. Missing values are imputed with the observed minimum after normalization.

Example 1. Discovery

Analysis Populations

The "Full Analysis Set" ("FAS") consisted of pilot study patients with clinical data and a CT-based designation of either Revascularization CAD case, Native CAD case, or Control (N=336 for the FAS group).

The "Native CAD Set" was the subset of the FAS with Native CAD as verified by CT, who had analyte (metabolomic and lipidomic) data (N=120 for the Native CAD Set). These were subjects without previous revascularization procedures, such as percutaneous coronary intervention (PCI) or coronary artery bypass grafting (CABG).

The "Revasc CAD Set" was the subset of the FAS who had undergone previous revascularization, such as percutaneous coronary intervention (PCI) or coronary artery bypass grafting (CABG), and who had analyte data.

The "All CAD Set" was the union of the Native CAD Set and the Revasc CAD Set.

The "Control Set" was the subset of FAS who had a calcium score of zero and were designated a Control after inspection of CT data, and who had analyte data. (N=279 for the Control Set plus Native CAD Set). These subjects had no discernable atherosclerotic CAD based on the combined inspection of the non-contrast CT and the contrast-enhanced CT data.

It is noted that by design, the only racial group represented in the study was White. Therefore, race-based sub-populations were not defined. The data was not split into training and validation sets.

I: GLOBAL Pilot Study

A. Study Endpoints

For the GLOBAL Pilot Discovery Cohort, there were two primary endpoints in the analysis: (1) Native CAD; and (2) All CAD (Native or Revascularization). All analyses were applied to both primary endpoints.

B. Statistical Hypothesis

The null hypothesis of no association, between the metabolite or lipid and the endpoint, was tested against the two-sided alternative that association exists.

C. Multiple Comparisons and Multiplicity

False discovery rate (FDR) q-values were calculated (Benjamini and Hochberg, 1995). Associations with FDR q<0.05 were considered preliminary associations. In some circumstances, test results with raw p<0.05 were reported as well.

D. Missing Data

Endpoint data was not imputed. Potential covariates with more than 5% missing data were excluded. Potential covariates with less than 5% missing data were imputed to the mean.

Metabolites with more than 10% missing data were excluded from the main analyses. Missing values for metabolites and lipids with less than 10% missing were imputed to the observed minimum after normalization.

E. Covariates

Twelve potential covariates were referred to as "clinical variables": Age; Gender; Body Mass Index (BMI); Type II Diabetes; Current smoker; Fasting; Statin use; Niacin use; Fibrate use; Ezetimibe use; Fish oil use; and Bile acid sequestrant use.

A further set of seventy-seven potential covariates, listed in Table 1, were referred to as "conventional blood-based biomarker variables".

TABLE 1

| | Full name |
|---|---|
| Serum Test Name | |
| Adiponectin | Adiponectin |
| ALB | Albumin |
| ALP | Alkalaine phosphatase |
| ALT/GPT | Alanine transaminase |
| APO A1 | Apolipoprotein A-I |
| APO B | Apolipoprotein B |
| AST/GOT | Aspartate transaminase |
| Calcium | Calcium |
| C-PEP | C-Peptide |
| CREAT | Creatinine |
| DBILI | Direct Bilrubin |
| GGT | Gamma-glutamyl transferase |
| Glucose | Glucose |
| HCY | Homocysteine |
| HDL3 | High Density Lipoprotein Fraction 3 |
| HDL-C | High Density Lipoprotein Cholesterol |
| hsCRP | High Sensitive C Reactive Protein |
| Insulin | Insulin |
| LDH | Lactate dehydrogenase |
| LDL-C | Low Density Lipoprotein Cholesterol |
| LP(a) Mass | Lipoprotein (a) mass |
| LP(a)-C | Lipoprotein (a) cholesterol |
| LP(a)-P | Lipoprotein (a) particles number |
| Lp-PLA2 | Lipoprotein-associated phospholipase A2 |
| NEFA | Fatty acids |
| NTPROBNP | N-terminal pro-brain natriuretic peptide |
| OCN | Osteocalcin |
| PHOS | Phosphorous |
| PTH | Parathyroid hormone |
| sdLDL | Small dense Low Density Lipoprotein Cholesterol |
| TBILI | Total Bilirubin |
| Total Cholesterol | Total Cholesterol |
| TP | Total Protein |
| TRIG | Triglycerides |
| Uric Acid | Uric Acid |
| VIT D | Vitamin D |
| Plasma Test name | |
| B-Sitosterol | B-Sitosterol |
| Campesterol | Campesterol |

TABLE 1-continued

| | Full name |
|---|---|
| Cholestanol | Cholestanol |
| Desmosterol | Desmosterol |
| Leptin | Leptin |
| MPO | Myeloperoxidase |
| ProInsulin | ProInsulin |
| Whole Blood Test name | |
| AA2 | arachidonic acid |
| AAEPA | arachidonic divided by EPA |
| alphalin2 | alphalinoleic acid |
| arachidic2 | arachidic acid |
| behenic2 | behenic acid |
| cismontotl | palmitoleic + oleic + eicosenoic + nervonic |
| dcopentn32 | docosapentaenoic-n3 acid |
| dcopentn62 | docosapentaenoic-n6 acid |
| DHA2 | docosahexaenoic acid |
| dihomolin2 | dihomolinoleic acid |
| docosat2 | docosatetraenoic acid |
| eicosad2 | eicosadienoic acid |
| eicosen2 | eicosenoic acid |
| EPA2 | eicosapentaenoic acid |
| gammalin2 | gamma linoleic acid |
| HbA1C | Glycated hemoglobin A1C |
| ligno2 | lignoceric acid |
| linoleic2 | linoleic acid |
| myristic2 | myristic acid |
| nervonic2 | nervonic acid |
| O3Index | Omega 3 index |
| O3total | Omega 3 total |
| O6O3 | O6 total divided by O3 total |
| O6total | Omega 6 total |
| oleic2 | oleic acid |
| palmitic2 | palmitic acid |
| palmleic2 | palmitoleic acid |
| sattotal | myristic + palmitic + behenic + lignoceric + arachadic + stearic |
| stearic2 | stearic acid |
| tomegaprct | Total fatty acids |
| translin2 | translinoleic acid |
| transol2 | transoleic acid |
| transpalm2 | transpalmitoleic acid |
| transtotal | trans palmitoleic + trans oleic + trans linoleic |

As described below, a selected subset of these variables were used as covariates in the covariate-adjusted association analysis and/or as inputs for the prediction modeling analyses.

F. Analysis of Subgroups

The first primary endpoint was addressed using a subset of the FAS. Specifically the Native CAD Set was compared to the Control Set. The majority of the secondary analyses involved the Native CAD Set only. Additional sub-groups were considered during the analysis of secondary endpoints arising from CT.

II. Demographic and Baseline Characteristics

The baseline and demographic characteristics of patients in the pilot study were tabulated. Continuous variables were summarized by the mean and standard error; binary variables were summarized by the count and percentage.

Table 2 shows general patient characteristics by clinical group (Revasc CAD vs. Native CAD vs. Control). A Kruskall-Wallis test was performed to investigate homogeneity of continuous measures; a Pearson's chi-squared test was conducted for binary measures; unadjusted p-values are reported.

Table 3 shows general patient characteristics by primary endpoint specifically, Native CAD vs. Control, and All CAD vs. Control. A Mann-Whitney test was performed to investigate homogeneity of continuous measures; a Pearson's chi-squared test was conducted for binary measures; unadjusted p-values are reported.

TABLE 2

|  | All Controls | Native CAD | Revasc CAD | P-value |
|---|---|---|---|---|
| N | 160 | 120 | 58 |  |
| Age |  |  |  |  |
| mean (SE) | 54.79 (0.79) | 55.12 (0.87) | 58.4 (1.22) | 0.5768 |
| SBP |  |  |  |  |
| mean (SE) | 131.26 (1.36) | 134.86 (1.59) | 137.88 (2.81) | 0.2157 |
| DBP |  |  |  |  |
| mean (SE) | 80.19 (0.77) | 81.92 (1.07) | 80.19 (1.34) | 0.2659 |
| Male |  |  |  |  |
| N (%) | 71 (44.38) | 51 (42.50) | 36 (62.07) | 0.0351 |
| Hypertension |  |  |  |  |
| N (%) | 85 (53.12) | 82 (68.33) | 51 (89.47) | 3.06e−06 |
| Dyslipidemia |  |  |  |  |
| N (%) | 80 (50.63) | 85 (71.43) | 55 (96.49) | 8.7e−10 |
| Diabetes (Any) |  |  |  |  |
| N (%) | 9 (5.62) | 19 (15.83) | 19 (32.76) | 1.55e−06 |
| Type I Diabetes |  |  |  |  |
| N (%) | 0 (0.00) | 1 (0.83) | 0 (0.00) | 0.4021 |
| Type II Diabetes |  |  |  |  |
| N (%) | 9 (5.62) | 18 (15.00) | 19 (32.76) | 1.4e−06 |
| Current Smoker |  |  |  |  |
| N (%) | 17 (10.62) | 25 (20.83) | 8 (13.79) | 0.0571 |
| Former Smoker |  |  |  |  |
| N (%) | 36 (22.50) | 42 (35.00) | 33 (56.90) | 9.04e−06 |
| Chest Pain |  |  |  |  |
| N (%) | 109 (68.12) | 78 (65.00) | 40 (68.97) | 0.8158 |
| Angina Equivalent |  |  |  |  |
| N (%) | 67 (41.88) | 48 (40.00) | 31 (53.45) | 0.2125 |
| Shortness of Breath |  |  |  |  |
| N (%) | 42 (26.25) | 28 (23.33) | 17 (29.31) | 0.6797 |
| Family History of CAD |  |  |  |  |
| N (%) | 80 (50.00) | 72 (60.00) | 37 (63.79) | 0.1031 |
| Fasting |  |  |  |  |
| N (%) | 40 (25.00) | 36 (30.00) | 22 (37.93) | 0.1696 |
| Statin |  |  |  |  |
| N (%) | 49 (30.63) | 59 (49.17) | 51 (87.93) | 5.52e−13 |
| Niacin |  |  |  |  |
| N (%) | 5 (3.12) | 1 (0.83) | 2 (3.45) | 0.3843 |
| Fibrate |  |  |  |  |
| N (%) | 4 (2.50) | 7 (5.83) | 5 (8.62) | 0.1330 |
| Ezetimibe |  |  |  |  |
| N (%) | 4 (2.50) | 3 (2.50) | 5 (8.62) | 0.0722 |
| Fish Oil |  |  |  |  |
| N (%) | 18 (11.25) | 23 (19.17) | 6 (10.34) | 0.1147 |
| Bile Acid Sequestrant |  |  |  |  |
| N (%) | 3 (1.88) | 0 (0.00) | 0 (0.00) | 0.1857 |
| Aspirin |  |  |  |  |
| N (%) | 59 (36.88) | 52 (43.33) | 47 (81.03) | 3.72e−08 |
| Clopidogrel |  |  |  |  |
| N (%) | 3 (1.88) | 4 (3.33) | 28 (48.28) | 2.6e−24 |
| Vitamin K Antagonist |  |  |  |  |
| N (%) | 4 (2.50) | 7 (5.83) | 6 (10.34) | 0.0568 |

TABLE 2-continued

|  | All Controls | Native CAD | Revasc CAD | P-value |
|---|---|---|---|---|
| Nitrate | | | | |
| N (%) | 4 (2.50) | 4 (3.33) | 13 (22.41) | 1.36e−07 |
| Beta Blocker | | | | |
| N (%) | 51 (31.87) | 46 (38.33) | 49 (84.48) | 1.53e−11 |
| ACE Inhibitor | | | | |
| N (%) | 32 (20.00) | 35 (29.17) | 32 (55.17) | 3.01e−06 |

TABLE 3

|  | All CAD | All Controls | P-value | Native CAD | All Controls | P-value |
|---|---|---|---|---|---|---|
| N | 178 | 160 |  | 120 | 160 |  |
| Age | | | | | | |
| mean (SE) | 56.19 (0.72) | 54.79 (0.79) | 0.1968 | 55.12 (0.87) | 54.79 (0.79) | 0.7808 |
| SBP | | | | | | |
| mean (SE) | 135.84 (1.41) | 131.26 (1.36) | 0.0273 | 134.86 (1.59) | 131.26 (1.36) | 0.0707 |
| DBP | | | | | | |
| mean (SE) | 81.36 (0.84) | 80.19 (0.77) | 0.4625 | 81.92 (1.07) | 80.19 (0.77) | 0.2828 |
| Male | | | | | | |
| N (%) | 87 (48.88) | 71 (44.38) | 0.4722 | 51 (42.50) | 71 (44.38) | 0.8482 |
| Hypertension | | | | | | |
| N (%) | 133 (75.14) | 85 (53.12) | 3.98e−05 | 82 (68.33) | 85 (53.12) | 0.0145 |
| Dyslipidemia | | | | | | |
| N (%) | 140 (79.55) | 80 (50.63) | 5.08e−08 | 85 (71.43) | 80 (50.63) | 8.00e−04 |
| Diabetes (Any) | | | | | | |
| N (%) | 38 (21.35) | 9 (5.62) | 5.97e−05 | 19 (15.83) | 9 (5.62) | 0.0089 |
| Type I Diabetes | | | | | | |
| N (%) | 1 (0.56) | 0 (0.00) | 1.0000 | 1 (0.83) | 0 (0.00) | 0.8850 |
| Type II Diabetes | | | | | | |
| N (%) | 37 (20.79) | 9 (5.62) | 9.62e−05 | 18 (15.00) | 9 (5.62) | 0.0153 |
| Current Smoker | | | | | | |
| N (%) | 33 (18.54) | 17 (10.62) | 0.0584 | 25 (20.83) | 17 (10.62) | 0.0279 |
| Former Smoker | | | | | | |
| N (%) | 75 (42.13) | 36 (22.50) | 2.00e−04 | 42 (35.00) | 36 (22.50) | 0.0297 |
| Chest Pain | | | | | | |
| N (%) | 118 (66.29) | 109 (68.12) | 0.8086 | 78 (65.00) | 109 (68.12) | 0.6736 |
| Angina Equivalent | | | | | | |
| N (%) | 79 (44.38) | 67 (41.88) | 0.7229 | 48 (40.00) | 67 (41.88) | 0.8471 |
| Shortness of Breath | | | | | | |
| N (%) | 45 (25.28) | 42 (26.25) | 0.9371 | 28 (23.33) | 42 (26.25) | 0.6757 |
| Family History of CAD | | | | | | |
| N (%) | 109 (61.24) | 80 (50.00) | 0.0491 | 72 (60.00) | 80 (50.00) | 0.1233 |
| Fasting | | | | | | |
| N (%) | 58 (32.58) | 40 (25.00) | 0.1573 | 36 (30.00) | 40 (25.00) | 0.4265 |
| Statin | | | | | | |
| N (%) | 110 (61.80) | 49 (30.63) | 1.87e−08 | 59 (49.17) | 49 (30.63) | 0.0024 |
| Niacin | | | | | | |
| N (%) | 3 (1.69) | 5 (3.12) | 0.6094 | 1 (0.83) | 5 (3.12) | 0.3716 |
| Fibrate | | | | | | |
| N (%) | 12 (6.74) | 4 (2.50) | 0.1148 | 7 (5.83) | 4 (2.50) | 0.2670 |
| Ezetimibe | | | | | | |
| N (%) | 8 (4.49) | 4 (2.50) | 0.4871 | 3 (2.50) | 4 (2.50) | 1.0000 |

TABLE 3-continued

|   | All CAD | All Controls | P-value | Native CAD | All Controls | P-value |
|---|---|---|---|---|---|---|
| | | | Fish Oil | | | |
| N (%) | 29 (16.29) | 18 (11.25) | 0.2379 | 23 (19.17) | 18 (11.25) | 0.0923 |
| | | | Bile Acid Sequestrant | | | |
| N (%) | 0 (0.00) | 3 (1.88) | 0.2097 | 0 (0.00) | 3 (1.88) | 0.3567 |
| | | | Aspirin | | | |
| N (%) | 99 (55.62) | 59 (36.88) | 8.00e−04 | 52 (43.33) | 59 (36.88) | 0.3321 |
| | | | Clopidogrel | | | |
| N (%) | 32 (17.98) | 3 (1.88) | 2.97e−06 | 4 (3.33) | 3 (1.88) | 0.6989 |
| | | | Vitamin K Antagonist | | | |
| N (%) | 13 (7.30) | 4 (2.50) | 0.0770 | 7 (5.83) | 4 (2.50) | 0.2670 |
| | | | Nitrate | | | |
| N (%) | 17 (9.55) | 4 (2.50) | 0.0141 | 4 (3.33) | 4 (2.50) | 0.9587 |
| | | | Beta Blocker | | | |
| N (%) | 95 (53.37) | 51 (31.87) | 1.00e−04 | 46 (38.33) | 51 (31.87) | 0.3187 |
| | | | ACE Inhibitor | | | |
| N (%) | 67 (37.64) | 32 (20.00) | 6.00e−04 | 35 (29.17) | 32 (20.00) | 0.1015 |

III. Exploratory Data Analyses for Metabolites and Complex Lipids

Sample preparation and mass spectrometry analyses were conducted by Metabolon, Inc. The raw data contained a total of 1088 analytes, measured for 336 pilot study participants. Two pilot study participants had no data.

Of the 1088 analytes, 705 metabolites and 183 complex lipids (888 total) had less than 10% missing data. All 336 patients had less than 10% missing data. Statistical analyses were therefore applied to 888 analytes and 336 patients. There were 57 patients in the "Revasc CAD Set", 120 patients in the "Native CAD Set" and 159 patients in the "Control Set".

The data was normalized in advance of receipt. A logarithm (base 2) transformation was applied and histograms were created to show the distribution of expression by analyte (data not shown).

The metabolomics and lipidomics data were generated in a single batch, so no batch-correction was applied, however, a principal components analysis (PCA) was performed, to look for evidence of any site effects. Variables were centered and scaled to unit variance. The inventors evaluated the presence of absence of site effects and concluded that there were no systematic differences in the data obtained from different sites.

IV. Univariate Analysis of Metabolites and Complex Lipids

A. Methods

Univariate association analysis was performed for all primary and secondary endpoints using a Mann-Whitney test, and an FDR correction was applied. Listings were produced showing p-values and q-values for all analytes.

Any analyte with q<0.05 was considered a preliminary association. For each, a box-plot was generated to show the distribution of expression by clinical group. A heat-map was generated to show the preliminary metabolite associations for each endpoint: on the y-axis, patients were grouped by endpoint-value, on the x-axis a dendrogram showed clustering of metabolites with q<0.05. Similarly, a heat-map was generated to show the preliminary complex lipid associations for each endpoint.

B. Results

Table 4 shows details of metabolites with q<0.05 for the primary endpoint of Native CAD versus Controls; Table 5 shows details of complex lipids with q<0.05.

Table 6 shows details of metabolites with q<0.05 for the primary endpoint of All CAD versus Controls; Table 7 shows details of complex lipids with q<0.05.

TABLE 4

| Analyte | Biochemical | Sub-pathway | p-value | q-value |
|---|---|---|---|---|
| 168 | Isoleucylphenylalanine | Dipeptide | 7.87E−05 | 0.0207 |
| 163 | Isoleucylalanine | Dipeptide | 4.48E−05 | 0.0207 |
| 190 | Pyroglutamylglutamine | Dipeptide | 0.0001 | 0.0207 |
| 15 | Glutamate | Glutamate Metabolism | 0.0002 | 0.0219 |
| 1 | Glycine | Glycine Serine and Threonine Metabolism | 0.0004 | 0.0412 |

TABLE 5

| Analyte | Biochemical | Sub-pathway | p-value | q-value |
|---|---|---|---|---|
| 594 | CER18:0 | Sphingolipid Metabolism | 9.57E−05 | 0.0207 |
| 581 | SM16:0 | Sphingomyelin | 0.0004 | 0.0437 |

TABLE 6

| Analyte | Biochemical | Sub-pathway | p-value | q-value |
|---|---|---|---|---|
| 168 | Isoleucylphenylalanine | Dipeptide | 1.94E−06 | 0.0010 |
| 163 | Isoleucylalanine | Dipeptide | 5.10E−06 | 0.0010 |
| 1 | Glycine | Glycine Serine and Threonine Metabolism | 4.36E−06 | 0.0010 |

TABLE 6-continued

| Analyte | Biochemical | Sub-pathway | p-value | q-value |
|---|---|---|---|---|
| 15 | Glutamate | Glutamate Metabolism | 9.42E−06 | 0.0014 |
| 426 | 1-oleoylglycerol (18:1) | Monoacylglycerol | 5.84E−05 | 0.0059 |
| 236 | Mannose | Fructose Mannose and Galactose Metabolism | 9.30E−05 | 0.0080 |
| 238 | Glucuronate | Aminosugar Metabolism | 0.0001 | 0.0093 |
| 151 | Alpha-glutamyltyrosine | Dipeptide | 0.0002 | 0.0124 |
| 176 | Leucylserine | Dipeptide | 0.0003 | 0.0129 |
| 35 | 3-methylglutarylcarnitine-1 | Lysine Metabolism | 0.0004 | 0.0143 |
| 219 | Pyruvate | Glycolysis Gluconeogenesis and Pyruvate Metabolism | 0.0004 | 0.0144 |
| 207 | Valylleucine | Dipeptide | 0.0004 | 0.0152 |
| 315 | Propionylglycine (C3) | Fatty Acid Metabolism (also BCAA Metabolism) | 0.0005 | 0.0153 |
| 147 | Gamma-glutamylvaline | Gamma-glutamyl Amino Acid | 0.0005 | 0.0154 |
| 190 | Pyroglutamylglutamine | Dipeptide | 0.0005 | 0.0155 |
| 134 | Cysteine-glutathione disulfide | Glutathione Metabolism | 0.0006 | 0.0159 |
| 320 | Hydroxybutyrylcarnitine | Fatty Acid Metabolism(Acyl Carnitine) | 0.0006 | 0.0161 |
| 167 | Isoleucylleucine | Dipeptide | 0.0007 | 0.0168 |
| 218 | Glucose | Glycolysis Gluconeogenesis and Pyruvate Metabolism | 0.0008 | 0.0177 |
| 159 | Glycyltryptophan | Dipeptide | 0.0008 | 0.0180 |
| 1068 | X - 21452 | | 0.0009 | 0.0184 |
| 215 | ADSGEGDFXAEGGGVR | Fibrinogen Cleavage Peptide | 0.0009 | 0.0186 |
| 1053 | X - 21365 | | 0.0010 | 0.0188 |
| 206 | Valylisoleucine | Dipeptide | 0.0010 | 0.0189 |
| 242 | Alpha-ketoglutarate | TCA Cycle | 0.0011 | 0.0196 |
| 85 | Alpha-hydroxyisovaleroyl carnitine | Leucine Isoleucine and Valine Metabolism | 0.0013 | 0.0207 |
| 700 | 2prime-deoxyuridine | Pyrimidine Metabolism Uracil containing | 0.0014 | 0.0214 |
| 165 | Isoleucylglycine | Dipeptide | 0.0015 | 0.0217 |
| 128 | Acisoga | Polyamine Metabolism | 0.0015 | 0.0218 |
| 680 | Urate | Purine Metabolism (Hypo)Xanthine/Inosine containing | 0.0015 | 0.0219 |
| 1077 | X - 21626 | | 0.0015 | 0.0220 |
| 793 | Thymol sulfate | Food Component/Plant | 0.0015 | 0.0221 |
| 92 | Tigloylglycine | Leucine Isoleucine and Valine Metabolism | 0.0018 | 0.0243 |
| 354 | 12-HETE | Eicosanoid | 0.0018 | 0.0245 |
| 975 | X - 16129 | | 0.0019 | 0.0256 |
| 97 | 3-methyl-2-oxobutyrate | Leucine Isoleucine and Valine Metabolism | 0.0020 | 0.0265 |
| 205 | Valylglycine | Dipeptide | 0.0023 | 0.0292 |
| 26 | Imidazole propionate | Histidine Metabolism | 0.0026 | 0.0314 |
| 333 | Carnitine | Carnitine Metabolism | 0.0029 | 0.0343 |
| 108 | 2-hydroxybutyrate (AHB) | Methionine Cysteine SAM and Taurine Metabolism | 0.0033 | 0.0370 |
| 322 | Hexanoylcarnitine (C6) | Fatty Acid Metabolism (Acyl Carnitine) | 0.0034 | 0.0381 |
| 945 | X-12824 | | 0.0034 | 0.0383 |
| 1028 | X-21289 | | 0.0035 | 0.0384 |
| 694 | N2 N2-dimethylguanosine | Purine Metabolism Guanine containing | 0.0037 | 0.0402 |
| 166 | Isoleucylisoleucine | Dipeptide | 0.0039 | 0.0412 |
| 32 | 2-aminoadipate | Lysine Metabolism | 0.0039 | 0.0416 |
| 422 | Glycerol 3-phosphate (G3P) | Glycerolipid Metabolism | 0.0040 | 0.0422 |
| 737 | 2-hydroxyhippurate (salicylurate) | Benzoate Metabolism | 0.0045 | 0.0454 |
| 795 | Methyl glucopyranoside (alpha + beta) | Food Component/Plant | 0.0051 | 0.0486 |
| 196 | Threonylleucine | Dipeptide | 0.0052 | 0.0491 |

TABLE 7

| Analyte | Biochemical | Sub-pathway | p-value | q-value |
|---|---|---|---|---|
| 662 | CE18:2n6 | Cholesterol Ester | 3.01E−05 | 0.0037 |
| 561 | PL18:2n6 | Phospholipids | 0.0002 | 0.0110 |
| 666 | CE20:4n6 | Cholesterol Ester | 0.0005 | 0.0154 |
| 485 | Total Diacylglycerol | Diacylglycerol | 0.0005 | 0.0157 |
| 619 | DHC24:1 | Sphingolipid Metabolism | 0.0006 | 0.0160 |
| 517 | TG15:0 | Triacylglycerol | 0.0007 | 0.0171 |
| 496 | DG18:1n9 | Diacylglycerol | 0.0007 | 0.0173 |
| 615 | DHC20:1 | Sphingolipid Metabolism | 0.0008 | 0.0178 |
| 582 | SM18:0 | Sphingomyelin | 0.0010 | 0.0190 |
| 594 | CER18:0 | Sphingolipid Metabolism | 0.0013 | 0.0208 |

TABLE 7-continued

| Analyte | Biochemical | Sub-pathway | p-value | q-value |
|---|---|---|---|---|
| 515 | Total Triacylglycerol | Triacylglycerol | 0.0019 | 0.0250 |
| 547 | PL15:0 | Phospholipids | 0.0049 | 0.0473 |
| 489 | DG18:0 | Diacylglycerol | 0.0050 | 0.0480 |

V. Prediction Modeling for Primary Endpoints

A. Methods

Gradient boosting is an approach to determine a regression function that minimizes the expectation of a loss function. (Friedman J H., *Greedy function approximation: a gradient boosting machine.* Ann Statist 29(5): 1189-1232 (2001); Friedman J H., *Stochastic gradient boosting.* Comput Stat Data Anal 38(4): 367-378(2002)). It is an iterative method, in which the negative gradient of the loss function is calculated, a regression model is fitted, the gradient descent step size is selected, and the regression function is updated. The gradient is approximated by means of a regression tree, which makes use of covariate information, and at each iteration the gradient determines the direction in which the function needs to move, in order to improve the fit to the data.

Two rounds of gradient boosting were applied for discovery purposes, in order to select the most highly predictive metabolites and lipids respectively: (1) Metabolomics Model: Metabolomics data only; and (2) Lipidomics Model: Lipidomics data only.

A further four rounds of gradient boosting were applied in order to quantify the relative benefit of different levels of model complexity: (3) Clinical Model: Clinical variables, plus conventional blood-based biomarker variables; (4) Clinical-Metabolomic Model: Clinical variables, conventional blood-based biomarker variables, plus metabolomics data; (5) Clinical-Lipidomic Model: Clinical variables, conventional blood-based biomarker variables, plus lipidomics data; and (6) Clinical-Metabolomic-Lipidomic Model: Clinical variables, conventional blood-based biomarker variables, plus metabolomics and lipidomics.

To simplify the search space, variables were filtered to include only those exhibiting nominal univariate association (raw p<0.05) for the endpoint of interest. The loss function was assumed Bernoulli, due to the binary nature of the primary endpoints. A learning rate (λ) was introduced to dampen proposed moves and to protect against over-fitting. The optimal number of iterations, given by T, was determined by 5-fold cross-validation. The minimum number of observations in each terminal node was 10. Two-way interactions were allowed. Random sub-sampling, without replacement, of half of the observations was applied to achieve variance reduction in gradient estimation.

The estimated performance of the derived models was summarized by the cross-validated (CV) estimate of loss (error), based upon the optimal number of iterations/trees. The variables selected, and their estimated relative influences were tabulated. Partial dependence plots were generated for variables exhibiting greatest influence.

In this way, six prediction models were derived for each primary endpoint, and preliminary estimates of model-performance were obtained using the same data.

The six models were used to generate probability predictions for each patient. For each model, the sensitivity, specificity, positive predictive value (PPV) and negative predictive value (NPV) were calculated for the range of predicted probability thresholds. A Receiver Operating Characteristic (ROC) curve was generated to plot sensitivity as a function of (1-specificity). The optimal classification threshold was determined on the basis of accuracy, defined as the proportion of correct predictions. In addition, the Area Under the Curve (AUC) was estimated.

Calibration performance was assessed graphically: plots were generated to show rates of CAD versus predicted risk. A Hosmer-Lemeshow C-test was performed.

The performance of model-based predictions were compared to the performance of probability predictions obtained by Diamond-Forrester scoring and Morise scoring. (Diamond G A, Forrester J S. Analysis of probability as an aid in the clinical diagnosis of coronary-artery disease. N Engl J Med. 1979 Jun. 14; 300(24):1350-8; Morise A P, Jalisis F. Evaluation of pretest and exercise test scores to assess all-cause mortality in unselected patients presenting for exercise testing with symptoms of suspected coronary artery disease. J Am Coll Cardiol. 2003 Sep. 3; 42(5):842-50).

Detailed Results for Native CAD

Figure 1:
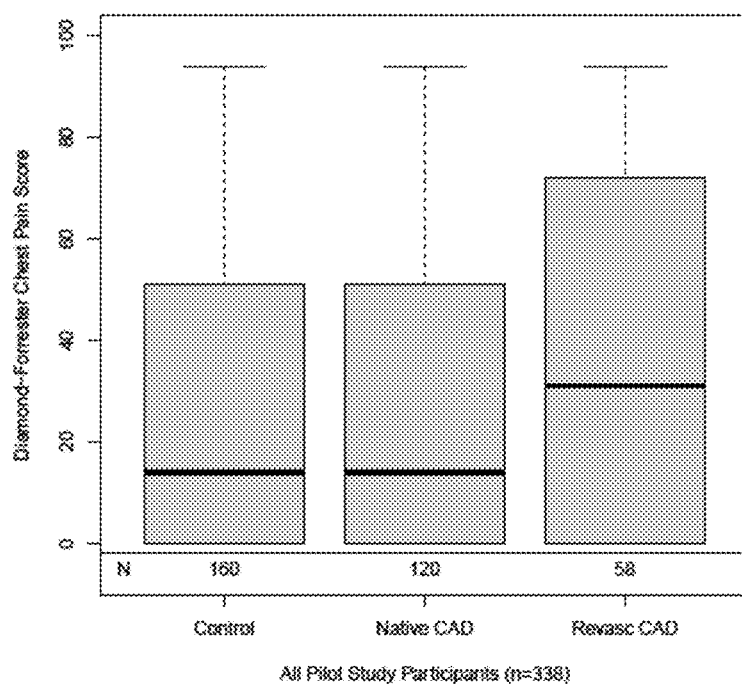
FIG. 1 is a graph demonstrating a box plot of Diamond Forrester Score by clinical group.
Figure 2:
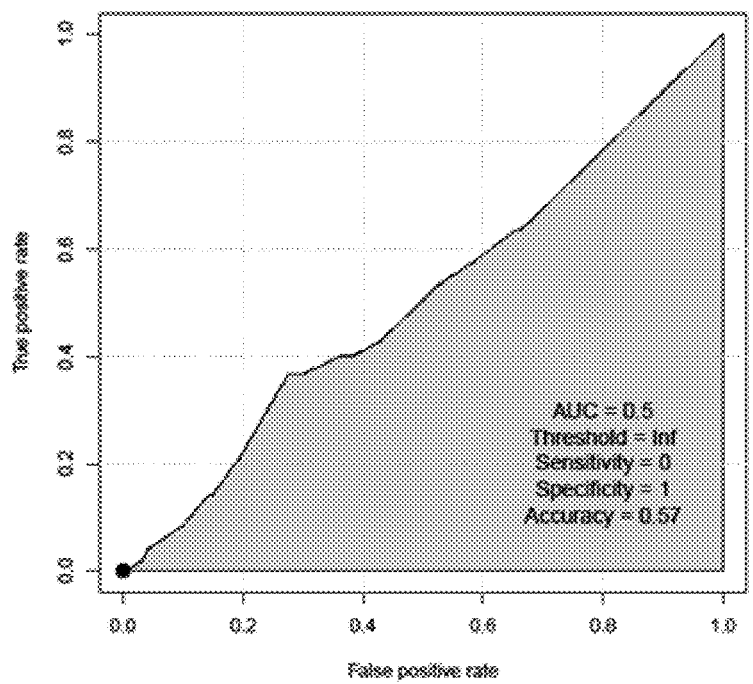
FIG. 2 is a graph demonstrating a ROC curve for Diamond Forrester Score and Native CAD (AUC=0.5; Threshold=inf; Sensitivity=0; Specificity=1; Accuracy=0.57).
Figure 17:
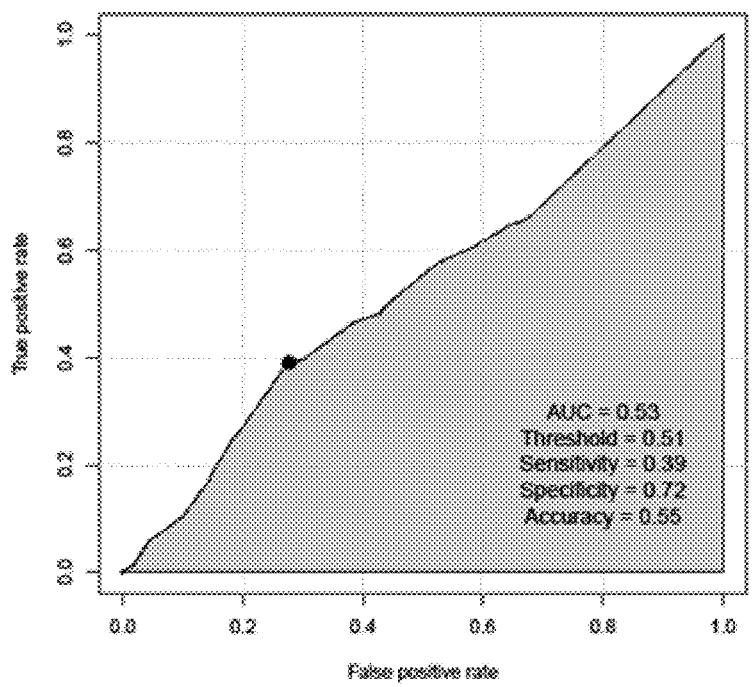
FIG. 17 is a graph demonstrating a ROC curve for Diamond Forrester Score and All CAD (AUC=0.53; Threshold=0.51; Sensitivity=0.39; Specificity=0.72; Accuracy=0.55).

The results show that the Diamond-Forrester score provides poor prediction of the GLOBAL phenotypes (FIG. 1). The estimates of AUC and accuracy for prediction of Native CAD indicate that performance is no better than assigning all patients an equal probability of 0.57 of disease. (FIG. 2) Some modest improvement in performance was obtained for All CAD, but performance remained weak. (FIG. 17)

Figure 3:
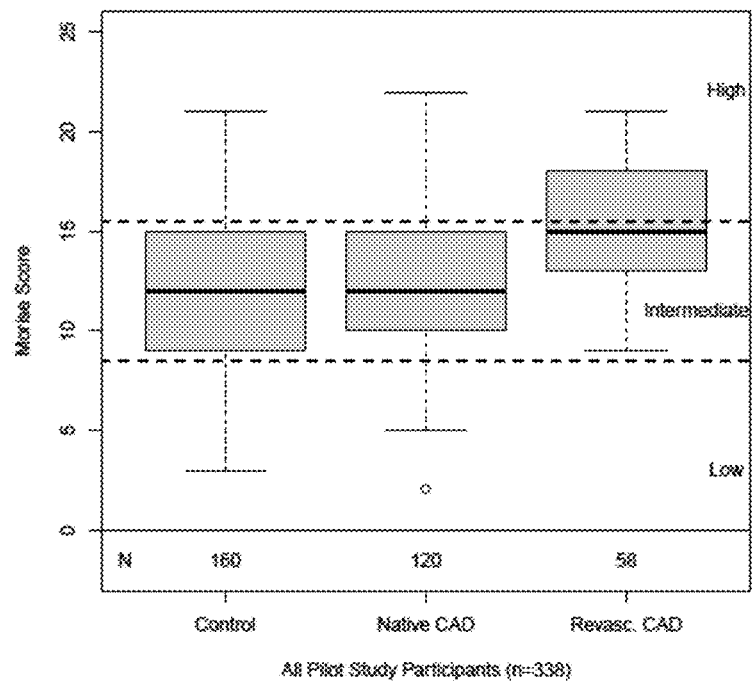
FIG. 3 is a graph demonstrating a box plot of Morise Score by clinical group.
Figure 4:
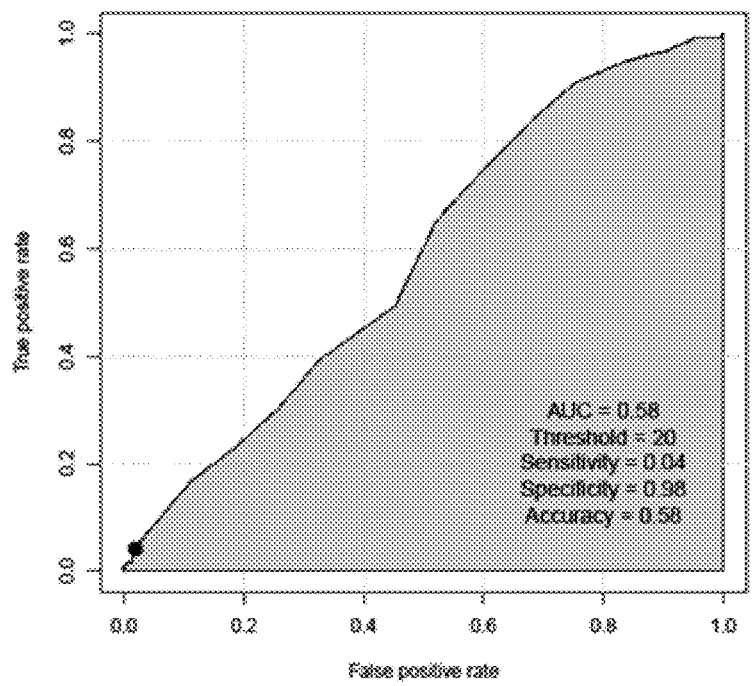
FIG. 4 is a graph demonstrating a ROC curve for Morise Score of Native CAD (AUC=0.58; Threshold=20; Sensitivity=0.04; Specificity=0.98; Accuracy=0.58).
Figure 18:
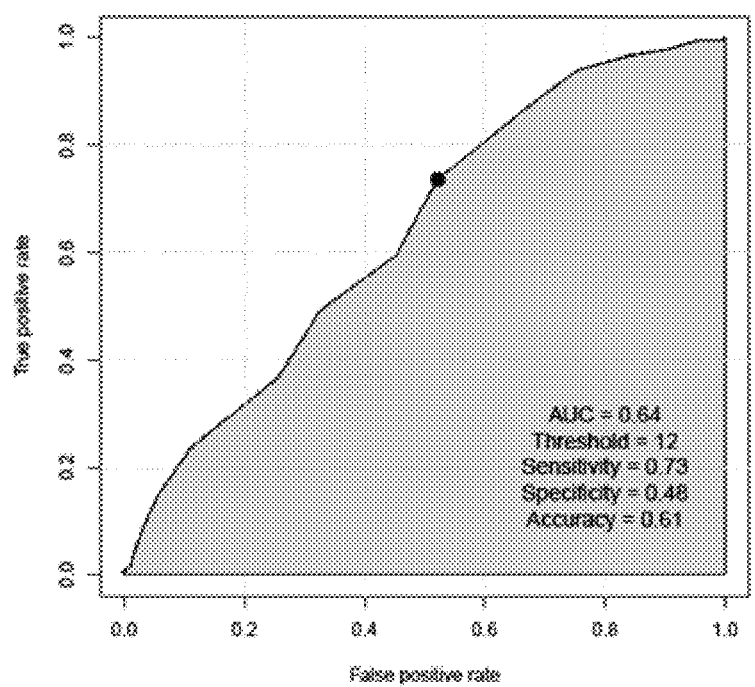
FIG. 18 is a graph demonstrating a ROC curve for Morise Score of All CAD (AUC=0.64; Threshold=12; Sensitivity=0.73; Specificity=0.48; Accuracy=0.61).

The Morise Score also performs poorly for prediction of Native CAD, but better for the prediction of All CAD. (FIGS. 3 and 4) For the latter, accuracy of 0.61 was obtained, which compares favorably to the minimum accuracy of 0.53, obtained by assigning all patients an equal probability of disease. (FIG. 18)

Clinical Model

Of the 888 analytes measured (705 metabolites and 183 complex lipids), 28 clinical variables exhibited a nominal univariate association (raw p<0.05) for Native CAD (Table 8). Table 9 provides the filtered list of the 28 clinical variables for All CAD.

TABLE 8

Age
Apo.B
B-Sitosterol
BMI
fast
FishOil
LDL.C
linoleic2
Log.ALP
Log.Campesterol
Log.GGT
Log.Glucose
Log.hsCRP
Log.Insulin
Log.Lp.a..C..mg.dL.
Log.Lp.a..mass
Log.Lp.a..P..nmol.L.
Log.palmleic2
Log.ProInsulin
Log.sdLDL.C
Log.Trig
Male
MHDM2
SMKCURR
Statin
Total.cholesterol
Uric.acid
Vit.D..ng.mL.

Figure 5:
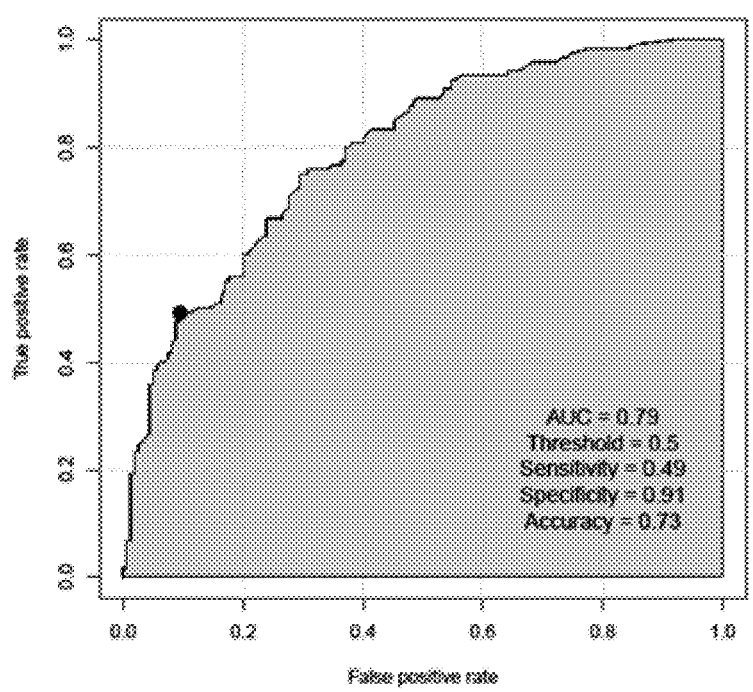
FIG. 5 is a graph demonstrating a ROC curve for the Clinical Model of Native CAD (AUC=0.79; Threshold=0.5; Sensitivity=0.49; Specificity=0.9; Accuracy=0.73).
Figure 6:
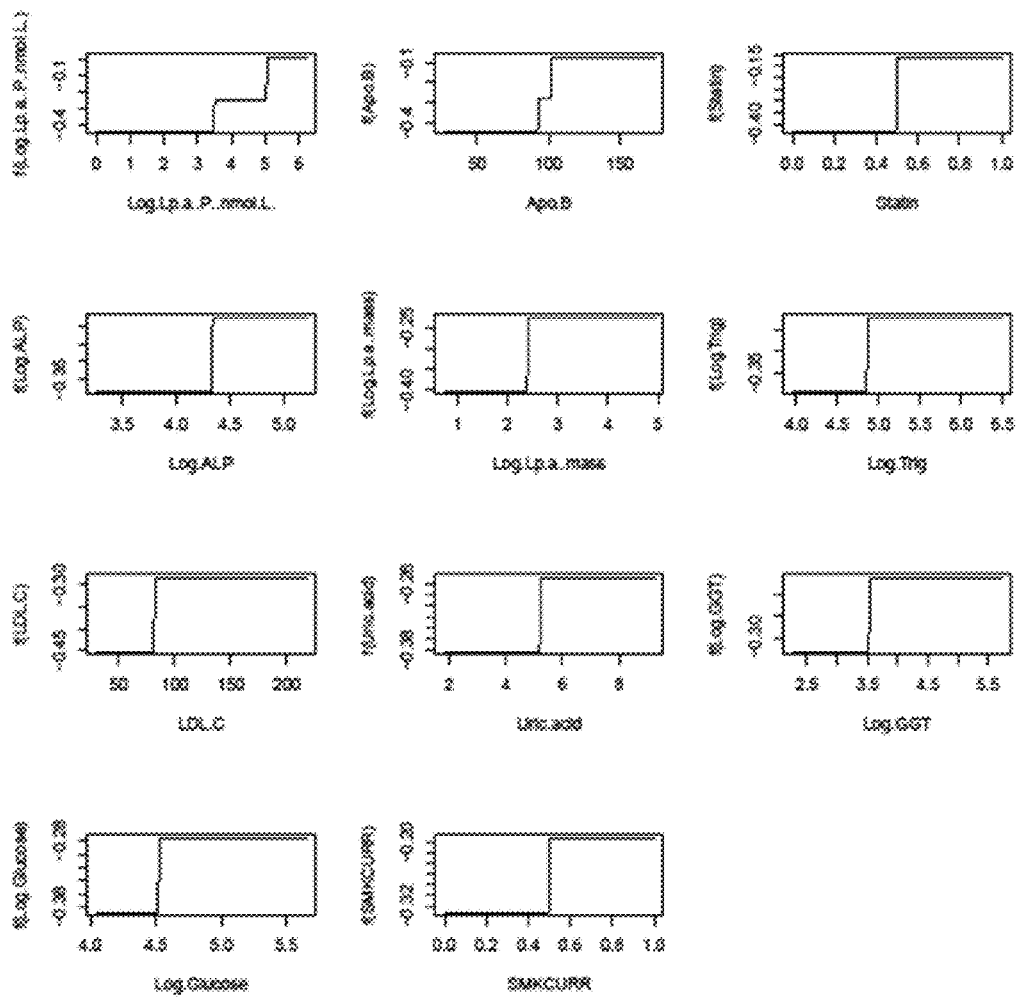
FIG. 6 is a series of graphs that provide Partial Dependence Plots for the eleven clinical variables for Clinical Model of Native CAD.

Of the 28 clinical variables exhibiting a nominal univariate association (raw p<0.05) for Native CAD, a panel of ten clinical variables were predictive for probability of CAD. Table 9 provides the relative influence of the eleven clinical variables for Clinical Model of Native CAD. FIG. 5 provides a ROC curve for the Clinical Model of Native CAD. FIG. 6 provides Partial Dependence Plot for the eleven clinical variables for Clinical Model of Native CAD.

TABLE 9

| Variable | Relative Influence | Direction of Change |
|---|---|---|
| Log.Lp.a..P..nmol.L. | 19.09 | Elevated |
| Apo.B | 15.25 | Elevated |
| Statin | 13.52 | Elevated |
| Log.ALP | 10.50 | Elevated |
| Log.Lp.a..mass | 7.93 | Elevated |
| Log.Trig | 6.71 | Elevated |
| LDL.C | 6.55 | Elevated |
| Uric.acid | 6.19 | Elevated |
| Log.GGT | 5.50 | Elevated |
| Log.Glucose | 4.63 | Elevated |
| SMKCURR | 4.13 | Elevated |

Metabolomics Model

Of the 888 analytes measured, 105 clinical variables exhibited a nominal univariate association (raw p<0.05) for Native CAD. Table 10 provides a filtered list of the 105 metabolomic variables for Native CAD.

Figure 7:
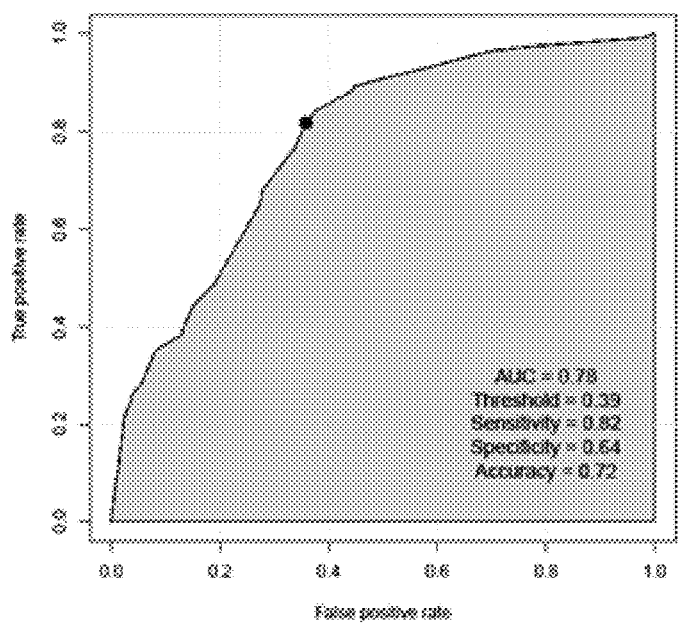
FIG. 7 is a graph demonstrating a ROC curve for the Metabolomic Model of Native CAD (AUC=0.78; Threshold=0.39; Sensitivity=0.82; Specificity=0.64; Accuracy=0.72).
Figure 8:
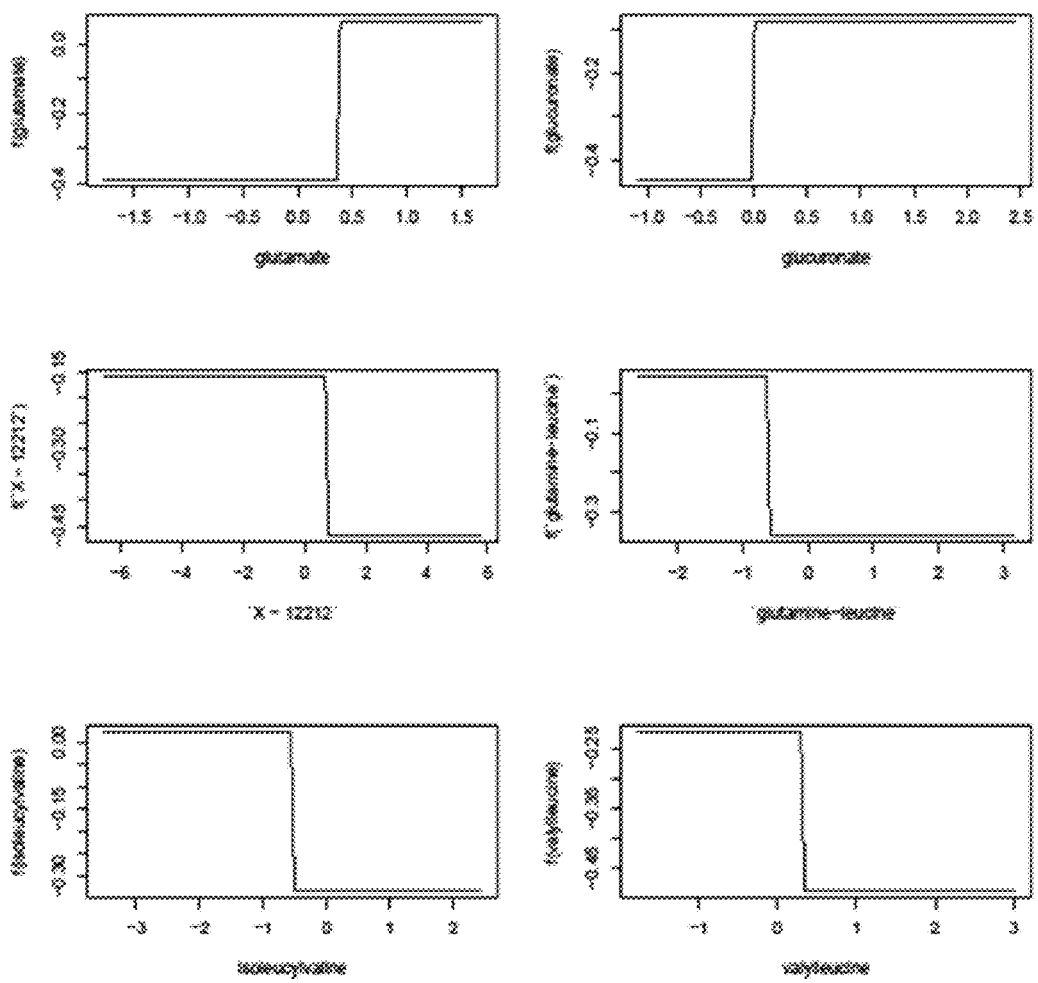
FIG. 8 is a series of graphs that provide Partial Dependence Plots for the six clinical variables for Metabolomic Model of Native CAD.

Of the 105 clinical variables exhibiting a nominal univariate association for Native CAD, a panel of six metabolomic variables were predictive for probability of CAD. Table 11 provides the relative influence of the six clinical variables for the Metabolomics Model of Native CAD. FIG. 7 provides a ROC curve for the Metabolomics Model of Native CAD. FIG. 8 provides Partial Dependence Plot for the six clinical variables for Metabolomics Model of Native CAD.

TABLE 11

| Variable | Relative Influence | Direction of Change |
|---|---|---|
| glutamate | 23.34 | Elevated |
| glucuronate | 19.02 | Elevated |
| 'X-12212' | 15.63 | Decreased |
| 'glutamine-leucine' | 15.12 | Decreased |
| isoleucylvaline | 14.46 | Decreased |
| valylleucine | 12.43 | Decreased |

Clinical-Metabolomic Model

Figure 9:
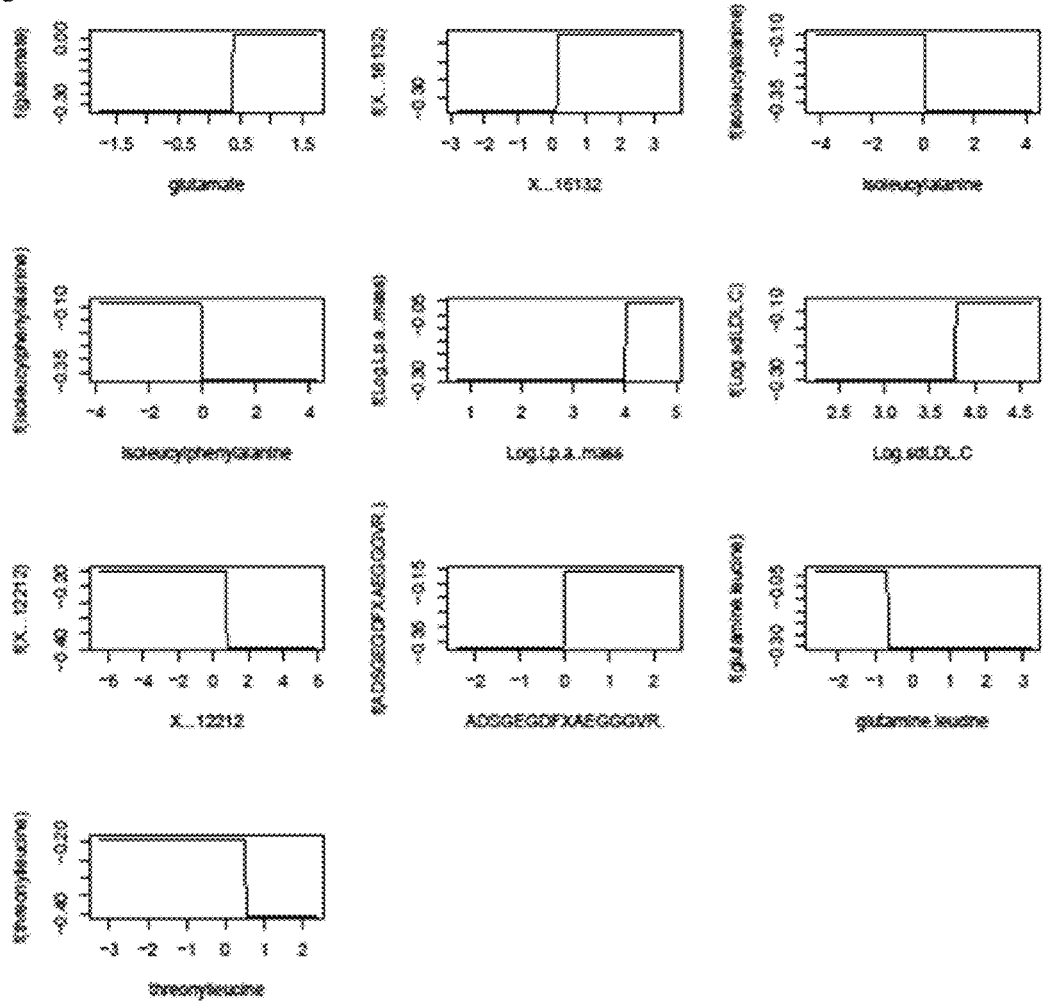
FIG. 9 is a series of graphs that provide Partial Dependence Plots for the ten clinical variables for Clinical-Metabolomic Model of Native CAD.
Figure 10:
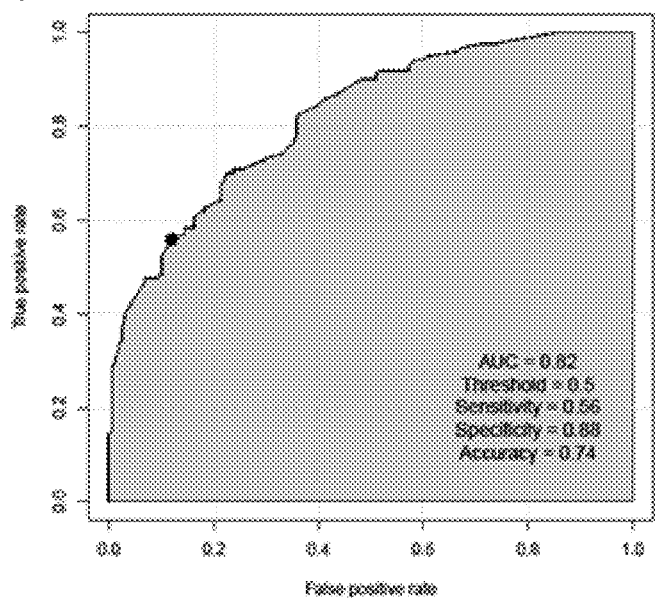
FIG. 10 is a graph demonstrating a ROC curve for the Clinical-Metabolomic Model of Native CAD (AUC=0.82; Threshold=0.5; Sensitivity=0.56; Specificity=0.88; Accuracy=0.74).

For the Clinical-Metabolomic Model, a panel of ten clinical variables were predictive for probability of CAD. Table 12 provides the relative influence of the ten clinical variables for the Clinical-Metabolomic Model of Native CAD. FIG. 9 provides Partial Dependence Plot for ten clinical variables for Clinical-Metabolomic Model of Native CAD. FIG. 10 provides a ROC curve for the Clinical-Metabolomic Model of Native CAD.

TABLE 10

| | | |
|---|---|---|
| 1-myristoylglycerol (14:0) | glycerol 3-phosphate (G3P) | serylleucine |
| 1-nonadecanoylglycerophosphocholine (19:0) | glycine | theobromine |
| 1-oleoylglycerol (18:1) | glycyltryptophan | threonate |
| 1-oleoylglycerophosphoglycerol | guanidinosuccinate | threonylleucine |
| 1-oleoyl-GPC (18:1) | histidylphenylalanine | tigloylglycine |
| 1-stearoylglycerophosphoglycerol | hydroxybutyrylcarnitine | tryptophylphenylalanine |
| 2-aminooctanoate | imidazole lactate | urate |
| 2-arachidonoyl-GPE (20:4) | imidazole propionate | valylglycine |
| 2-docosahexaenoylglycerophosphoethanolamine | indolepropionate | valylisoleucine |
| 2-hydroxybutyrate (AHB) | isobutyrylglycine (C4) | valylleucine |
| 2prime-deoxyuridine | isoleucylalanine | X - 12212 |
| 3 7-dimethylurate | isoleucylglycine | X - 12472 |
| 3-ethylphenylsulfate | isoleucylisoleucine | X - 12524 |
| 3-hydroxy-2-ethylpropionate | isoleucylleucine | X - 12544 |
| 3-methyl-2-oxobutyrate | isoleucylphenylalanine | X - 12824 |
| 3-methylglutarylcarnitine-1 | isoleucylvaline | X - 14056 |
| 3-methylxanthine | leucylglycine | X - 14291 |
| 4-hydroxyphenylacetate | leucylserine | X - 15245 |
| 7-methylurate | mannose | X - 16129 |
| 7-methylxanthine | methyl glucopyranoside (alpha + beta) | X - 16132 |
| acisoga | methyl indole-3-acetate | X - 17178 |
| ADSGEGDFXAEGGGVR | N2 N2-dimethylguanosine | X - 21289 |
| alpha-glutamyltyrosine | N4-acetylcytidine | X - 21335 |
| alpha-hydroxyisovaleroyl carnitine | N-acetylalanine | X - 21365 |
| alpha-ketobutyrate | N-acetyl-beta-alanine | X - 21452 |
| alpha-ketoglutarate | N-acetylputrescine | X - 21626 |
| asparagine | N-acetylthreonine | X - 21662 |
| carnitine | N-acetylvaline | xanthine |
| 1-myristoylglycerol (14:0) | glycerol 3-phosphate (G3P) | serylleucine |
| 1-nonadecanoylglycerophosphocholine (19:0) | glycine | theobromine |
| 1-oleoylglycerol (18:1) | glycyltryptophan | threonate |
| 1-oleoylglycerophosphoglycerol | guanidinosuccinate | threonylleucine |
| 1-oleoyl-GPC (18:1) | histidylphenylalanine | tigloylglycine |
| 1-stearoylglycerophosphoglycerol | hydroxybutyrylcarnitine | tryptophylphenylalanine |
| 2-aminooctanoate | imidazole lactate | urate |

TABLE 12

| Variable | Relative Influence | Direction of Change |
| --- | --- | --- |
| glutamate | 13.13 | Elevated |
| X-16132 | 11.78 | Elevated |
| isoleucylalanine | 11.43 | Decreased |
| isoleucylphenylalanine | 11.11 | Decreased |
| Log.Lp.a..mass | 9.38 | Elevated |
| Log.sdLDL.C | 9.04 | Elevated |
| X-12212 | 8.84 | Decreased |
| ADSGEGDFXAEGGGVR. | 8.82 | Elevated |
| glutamine.leucine | 8.66 | Decreased |
| threonylleucine | 7.82 | Decreased |

Lipidomics Model

Of the 138 lipids evaluated, 29 exhibited a nominal univariate association (raw $p<0.05$) for Native CAD. Table 13 provides a filtered list of the 29 lipidomic variables for Native CAD.

TABLE 13

Figure 11:
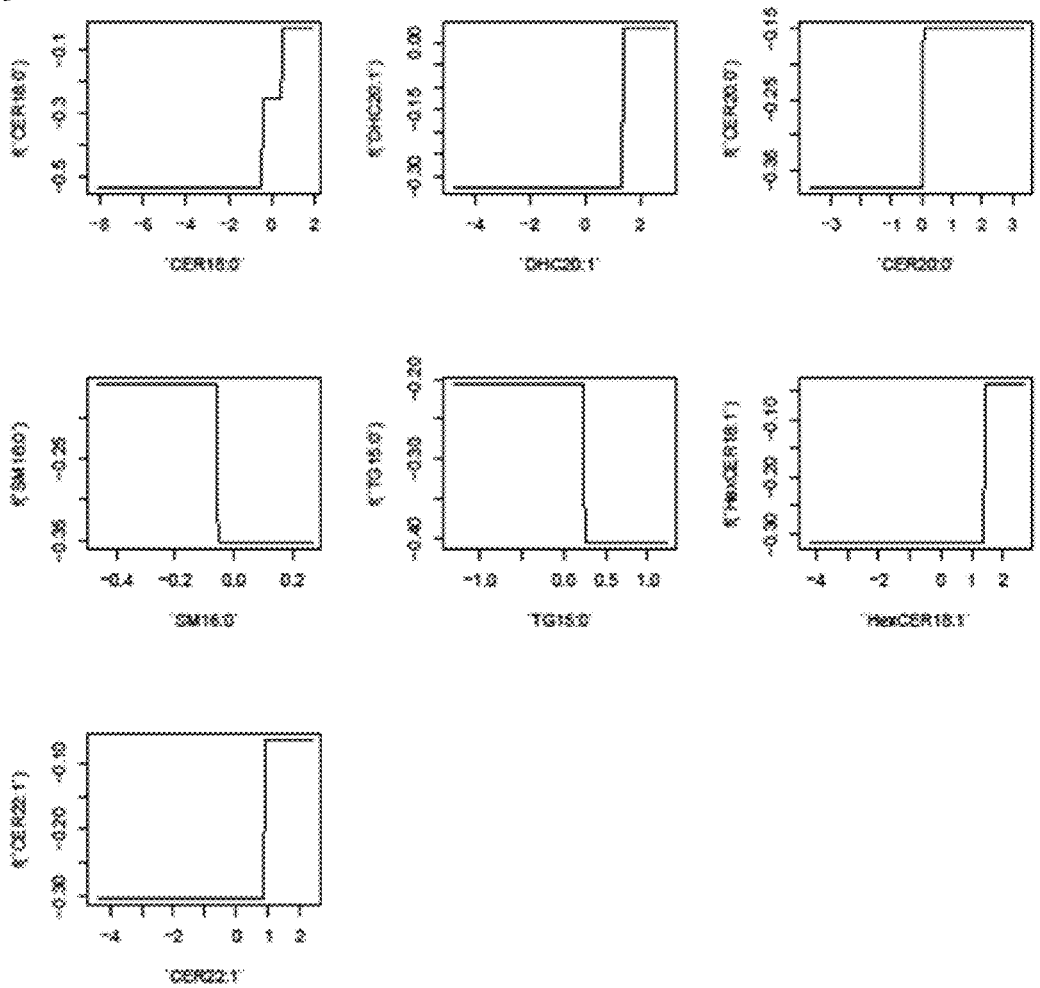
FIG. 11 is a series of graphs that provide Partial Dependence Plots for the seven clinical variables for Lipidomic Model of Native CAD.
Figure 12:
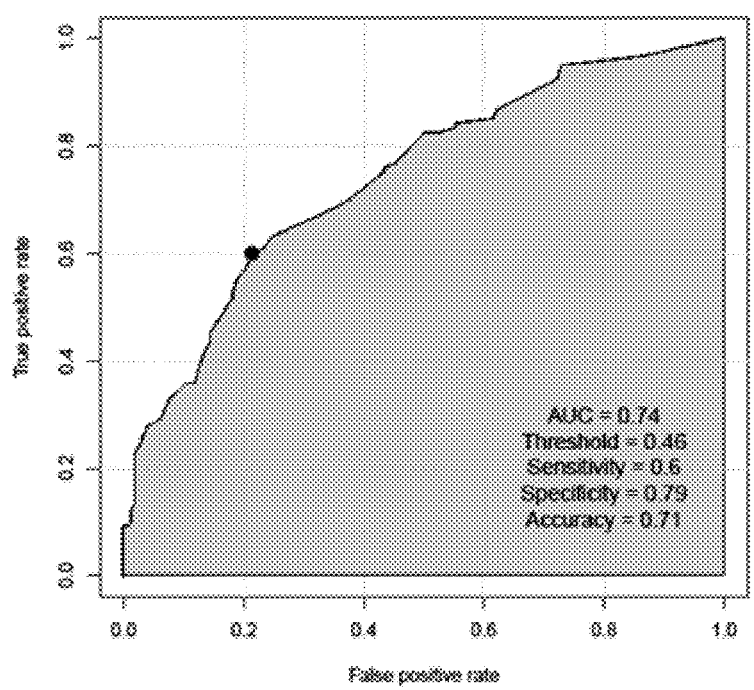
FIG. 12 is a graph demonstrating a ROC curve for Lipidomic Model of Native CAD (AUC=0.74; Threshold=0.46; Sensitivity=0.6; Specificity=0.79; Accuracy=0.71).

CE16:1n7
CE18:2n6
CE20:4n6
CER18:0
CER20:0
CER22:1
DG16:0
DG18:0
DG18:1n9
DG20:3n9
DHC18:0
DHC18:1
DHC20:1
DHC24:0
DHC24:1
FA18:3n6
FA20:3n6
HexCER14:0
HexCER16:0
HexCER18:1
LacCER16:0
PL15:0
PLdm16:0
PLdm18:1n9
SM16:0
SM20:1
TG15:0
TG16:0
Total Triacylglycerol For the Lipidomics Model, a panel of seven variables were predictive for probability of CAD. Table 14 provides the relative influence of seven lipidomic variables for the Lipidomics Model of Native CAD. FIG. 11 provides Partial Dependence Plot for seven clinical variables for Lipidomics Model of Native CAD. FIG. 12 provides a ROC curve for the Lipidomics Model of Native CAD.

TABLE 14

| Variable | Relative Influence | Direction of Change |
| --- | --- | --- |
| CER18:0 | 29.10 | Elevated |
| DHC20:1 | 17.10 | Elevated |
| CER20:0 | 12.54 | Elevated |
| SM16:0 | 12.25 | Decreased |
| TG15:0 | 10.54 | Decreased |
| HexCER18:1 | 10.31 | Elevated |
| CER22:1 | 8.15 | Elevated |

Clinical-Lipidomic Model

Figure 13:
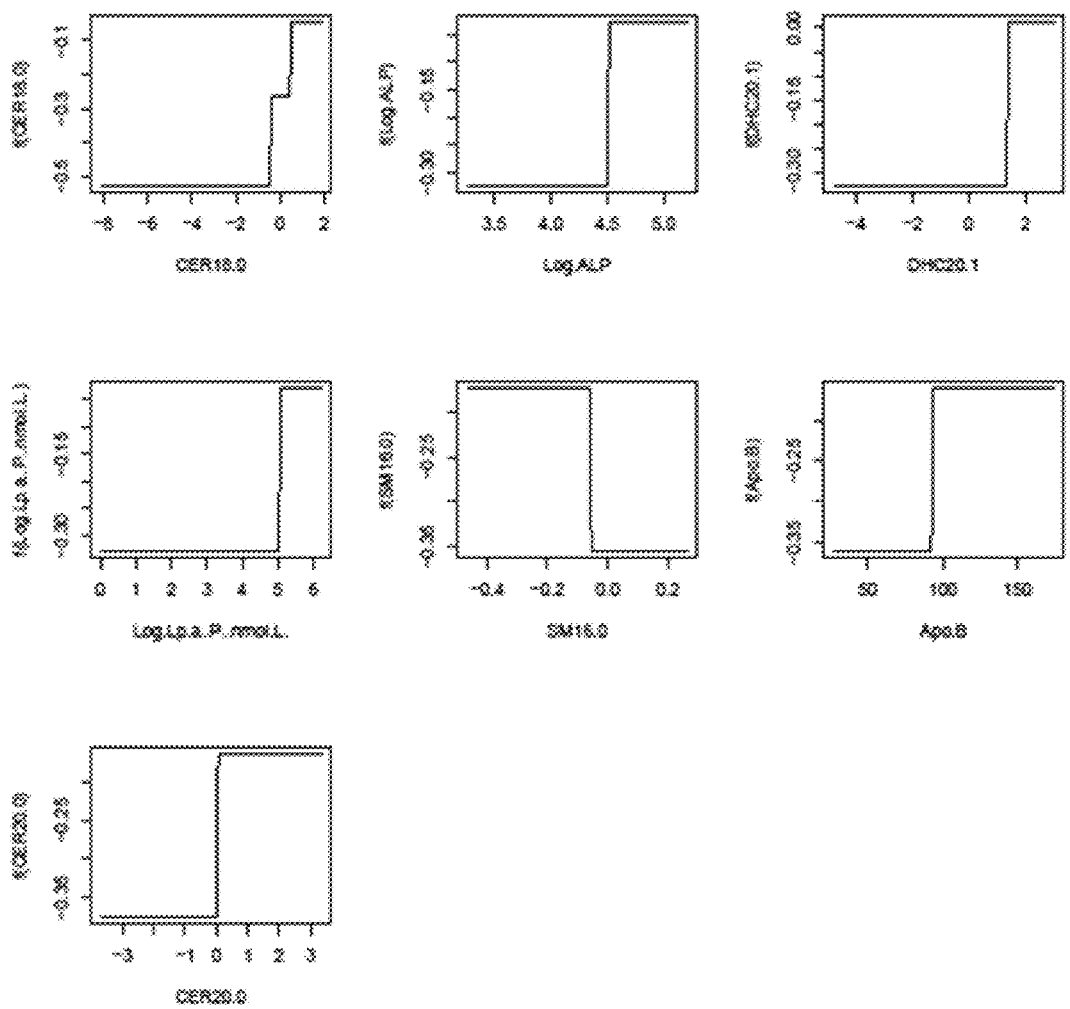
FIG. 13 is a series of graphs that provide Partial Dependence Plots for the seven clinical variables for Clinical-Lipidomic Model of Native CAD.
Figure 14:
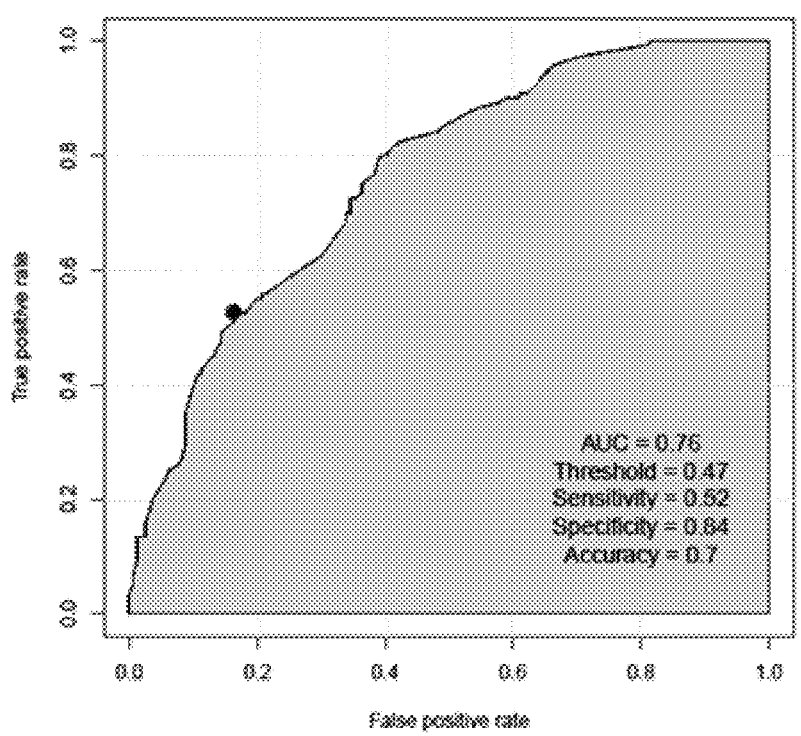
FIG. 14 is a graph demonstrating a ROC curve for the Clinical-Lipidomic Model of Native CAD (AUC=0.76; Threshold=0.47; Sensitivity=0.52; Specificity=0.84; Accuracy=0.7).

A panel of seven clinical variables were predictive for probability of CAD in the Clinical-Lipidomic Model. Table 15 provides the relative influence of those seven clinical variables for the Clinical-Lipidomics Model of Native CAD. FIG. 13 provides Partial Dependence Plot for seven clinical variables for Clinical-Lipidomics Model of Native CAD. FIG. 14 provides a ROC curve for the Clinical-Lipidomic Model of Native CAD.

TABLE 15

| Variable | Relative Influence | Direction of Change |
| --- | --- | --- |
| CER18.0 | 25.81 | Elevated |
| Log.ALP | 14.97 | Elevated |
| DHC20.1 | 14.88 | Elevated |
| Log.Lp.a..P..nmol.L. | 12.85 | Elevated |
| SM16.0 | 10.61 | Decreased |
| Apo.B | 10.49 | Elevated |
| CER20.0 | 10.40 | Elevated |

Clinical-Metabolomic-Lipidomic Model

Figure 15:
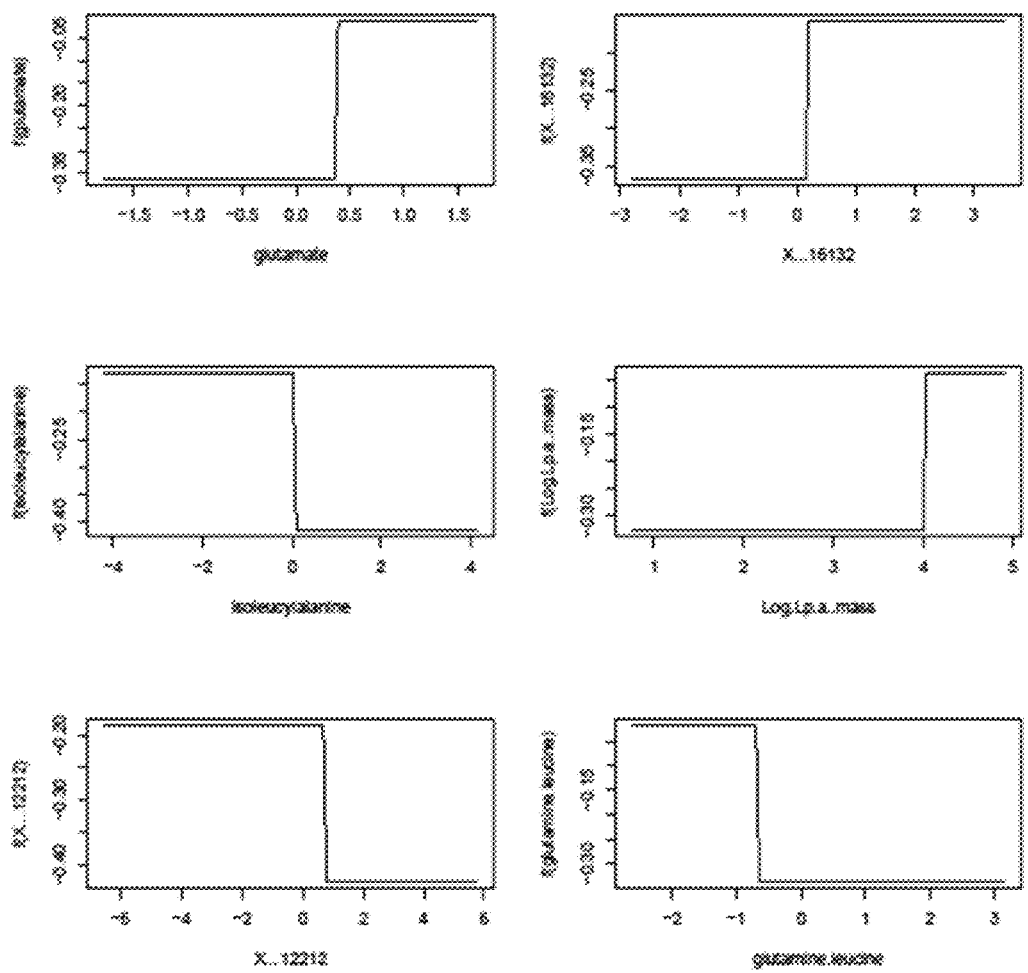
FIG. 15 is a series of graphs that provide Partial Dependence Plots for the six clinical variables for Clinical-Metabolomic-Lipidomic Model of Native CAD.
Figure 16:
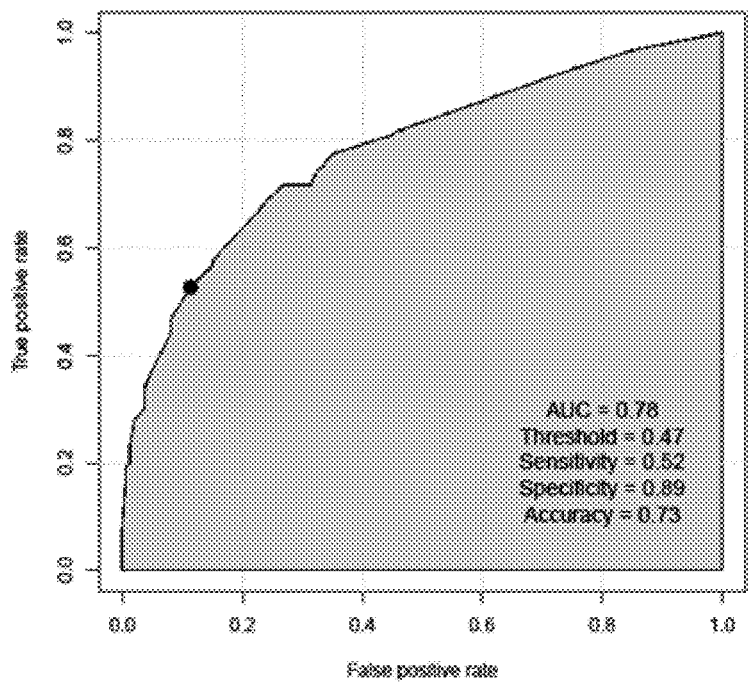
FIG. 16 is a graph demonstrating a ROC curve for the Clinical-Metabolomics-Lipidomic Model of Native CAD (AUC=0.78; Threshold=0.47; Sensitivity=0.52; Specificity=0.89; Accuracy=0.73).

A panel of six clinical variables were predictive for probability of CAD in the Clinical-Metabolomic-Lipidomic Model. Table 16 provides the relative influence of those six variables for the Clinical-Metabolomic-Lipidomic Model of Native CAD. FIG. 15 provides Partial Dependence Plot for six clinical variables for Clinical-Metabolomic-Lipidomics Model of Native CAD. FIG. 16 provides a ROC curve for the Clinical-Metabolomic-Lipidomic Model of Native CAD.

TABLE 16

| Variable | Relative Influence | Direction of Change |
| --- | --- | --- |
| glutamate | 20.76 | Elevated |
| X-16132 | 18.63 | Elevated |
| isoleucylalanine | 18.08 | Decreased |
| Log.Lp.a..mass | 14.83 | Elevated |
| X-12212 | 13.98 | Decreased |
| glutamine.leucine | 13.71 | Decreased |

Detailed Results for All CAD

Clinical Model 35 clinical variables exhibited a nominal univariate association (raw $p<0.05$) for Native CAD (Table 17). Table 17 provides a filtered list of the 35 clinical variables for All CAD.

TABLE 17

Age
B-Sitosterol
behenic2
BMI
cismontotl
Fast
FishOil
HDL3.C
linoleic2
Log.A1C
Log.Adiponectin
Log.Campesterol
Log.Desmosterol
Log.GGT
Log.Glucose
Log.HDL.C
Log.Insulin
Log.Lp.a..C..mg.dL.
Log.Lp.a..mass
Log.Lp.a..P..nmol.L.
Log.NT.ProBNP
Log.palmleic2
Log.ProInsulin TABLE 17-continued Log.sdLDL.C
Log.Trig
Male
MHDM2
nervonic2
O6total
oleic2
SMKCURR
Statin
transpalm2
Uric.acid
Vit.D..ng.mL.

Figure 19:
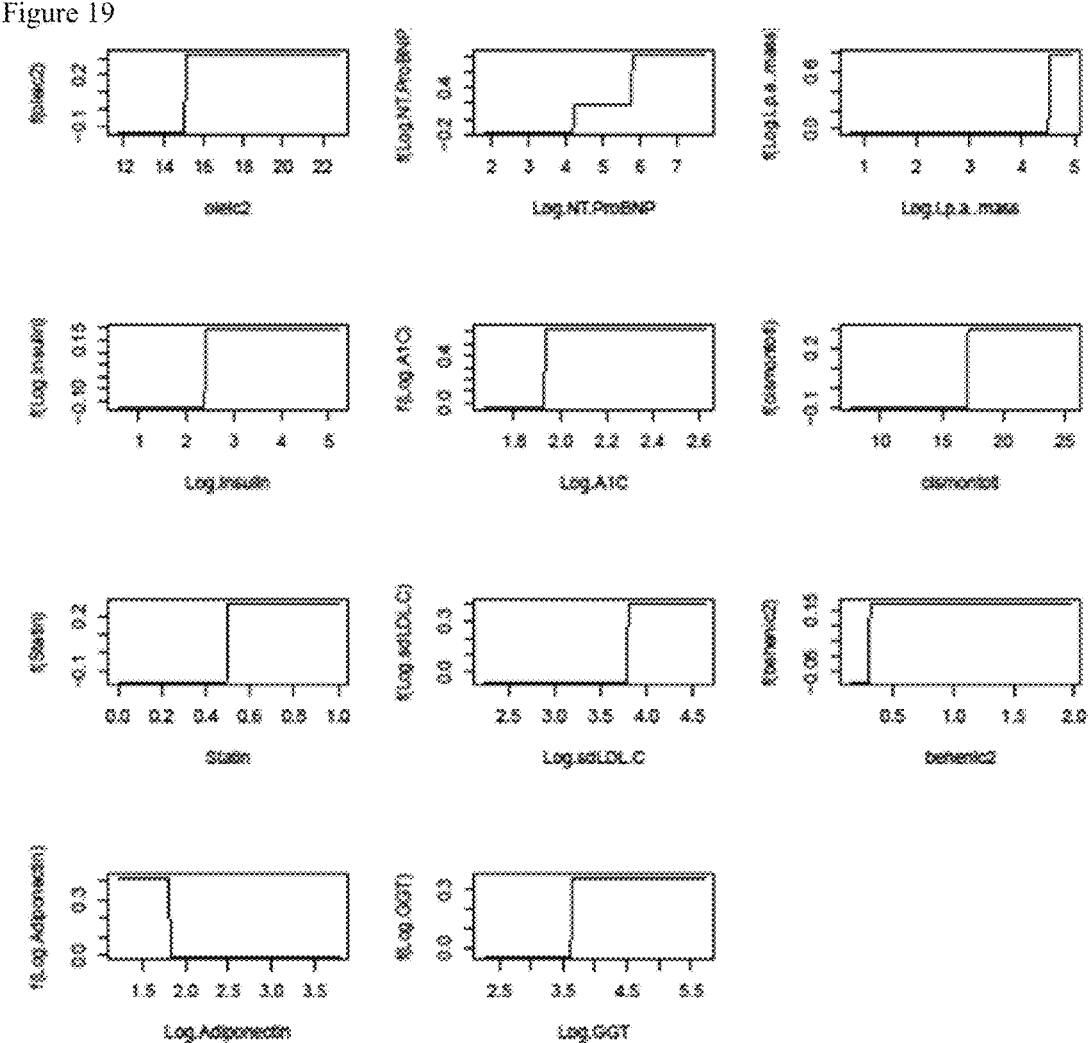
FIG. 19 is a series of graphs that provide Partial Dependence Plots for the eleven clinical variables for Clinical Model of All CAD.
Figure 20:
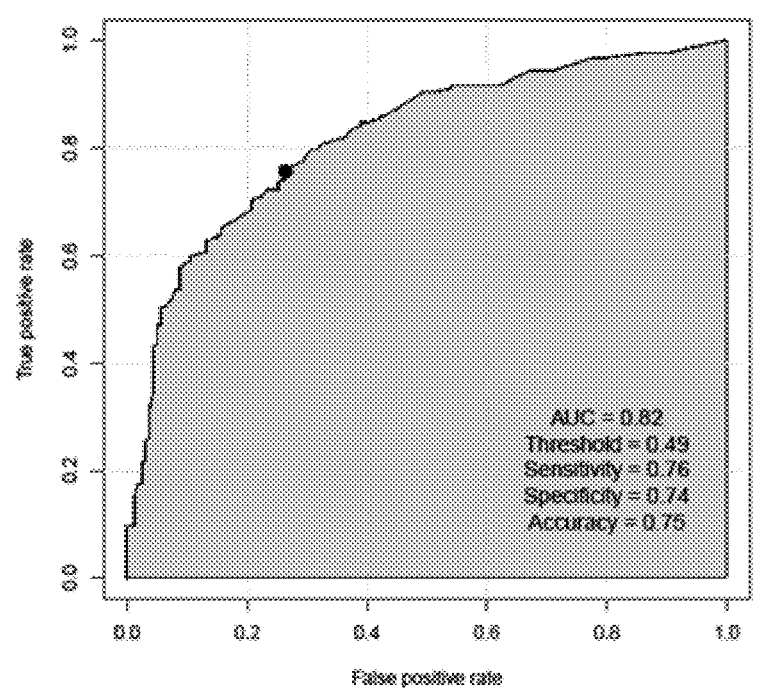
FIG. 20 is a graph demonstrating a ROC curve for the Clinical Model of All CAD (AUC=0.82; Threshold=0.49; Sensitivity=0.76; Specificity=0.74; Accuracy=0.75).

Of the 35 clinical variables exhibiting a nominal univariate association (raw p<0.05) for ALL CAD, a panel of eleven clinical variables were predictive for probability of CAD. Table 18 provides the relative influence of the eleven clinical variables for Clinical Model of All CAD. FIG. 19 provides Partial Dependence Plot for eleven clinical variables for Clinical Model of All Native CAD. FIG. 20 provides a ROC curve for the Clinical Model of All CAD.

TABLE 18

| Variable | Relative Influence | Direction of Change |
| --- | --- | --- |
| oleic2 | 12.78 | Elevated |
| Log.NT.ProBNP | 12.00 | Elevated |
| Log.Lp.a..mass | 11.62 | Elevated |
| Log.Insulin | 10.00 | Elevated |
| Log.A1C | 9.97 | Elevated |
| cismontotl | 8.93 | Elevated |
| Statin | 8.54 | Elevated |
| Log.sdLDL.C | 8.21 | Elevated |
| behenic2 | 6.23 | Elevated |
| Log.Adiponectin | 6.11 | Decreased |
| Log.GGT | 5.61 | Elevated |

Metabolomics Model

As shown in Table 19, a filtered list of 138 metabolomic variables a nominal univariate association (raw p<0.05) for All CAD.

TABLE 19

| | | |
| --- | --- | --- |
| 1 3-dimethylurate | glycerol 3-phosphate (G3P) | pyroglutamylglutamine |
| 1 7-dimethylurate | glycine | pyroglutamylglycine |
| 12-HETE | glycylphenylalanine | pyruvate |
| 1-linoleoyl-GPE (18:2) | glycyltryptophan | S-adenosylhomocysteine (SAH) |
| 1-methylurate | guanidinosuccinate | salicylate |
| 1-nonadecanoylglycerophosphocholine(19:0) | hexanoylcarnitine (C6) | serylleucine |
| 1-oleoylglycerol (18:1) | histidylphenylalanine | succinylcarnitine (C4) |
| 1-oleoylglycerophosphoglycerol | homostachydrine | threonate |
| 2-aminoadipate | hydroxybutyrylcarnitine | threonylleucine |
| 2-aminobutyrate | imidazole propionate | thymol sulfate |
| 2-aminooctanoate | indolepropionate | tigloylglycine |
| 2-arachidonoyl-GPE (20:4) | isobutyrylglycine (C4) | tryptophylglycine |
| 2-docosahexaenoylglycerophosphoethanolamine | isoleucylalanine | tryptophylphenylalanine |
| 2-hydroxybutyrate (AHB) | isoleucylglycine | tyrosylglutamine |
| 2-hydroxyhippurate (salicylurate) | isoleucylisoleucine | urate |
| 2-linoleoyl-GPE (18:2) | isoleucylleucine | valerylcarnitine (C5) |
| 2prime-deoxyuridine | isoleucylphenylalanine | valylglycine |
| 3-ethylphenylsulfate | isovalerylglycine | valylisoleucine |
| 3-hydroxyisobutyrate | kynurenine | valylleucine |
| 3-methyl-2-oxobutyrate | leucylaspartate | valylvaline |
| 3-methylglutarylcarnitine-1 | leucylglycine | X - 11429 |
| 3-methylglutarylcarnitine-2 | leucylserine | X - 11444 |
| 3-methylxanthine | lysylleucine | X - 11787 |
| 4-hydroxyphenylacetate | mannose | X - 11945 |
| 5alpha-androstan-3beta 17beta-diol monosulfate 2 | methyl glucopyranoside (alpha + beta) | X - 12212 |
| 7-methylurate | methyl indole-3-acetate | X - 12472 |
| 7-methylxanthine | N2 N2-dimethylguanosine | X - 12729 |
| acetylcarnitine (C2) | N4-acetylcytidine | X - 12824 |
| acisoga | N6-carbamoylthreonyladenosine | X - 14056 |
| ADSGEGDFXAEGGGVR | N-acetylalanine | X - 15245 |
| alpha-glutamyltyrosine | N-acetylglycine | X - 15492 |
| alpha-hydroxyisovaleroyl carnitine | N-acetylisoleucine | X - 16129 |
| alpha-ketobutyrate | N-acetylneuraminate | X - 16132 |
| alpha-ketoglutarate | N-acetylthreonine | X - 17178 |
| beta-tocopherol | N-acetylvaline | X - 17690 |
| butyrylcarnitine (C4) | N-methyl proline | X - 18914 |
| carnitine | octanoylcarnitine (C8) | X - 18922 |
| cysteine-glutathione disulfide | oleic ethanolamide | X - 19438 |
| cytidine | O-sulfo-L-tyrosine | X - 21289 |
| fucose | phenylalanylaspartate | X - 21335 |
| gamma-glutamylisoleucine | prolylphenylalanine | X - 21365 |
| gamma-glutamylvaline | propionylcarnitine (C3) | X - 21367 |
| glucose | propionylglycine (C3) | X - 21452 |
| glucuronate | pseudouridine | X - 21471 |
| glutamate | pyridoxal | X - 21626 |
| glutamine-leucine | pyridoxate | xanthine |

Figure 21:
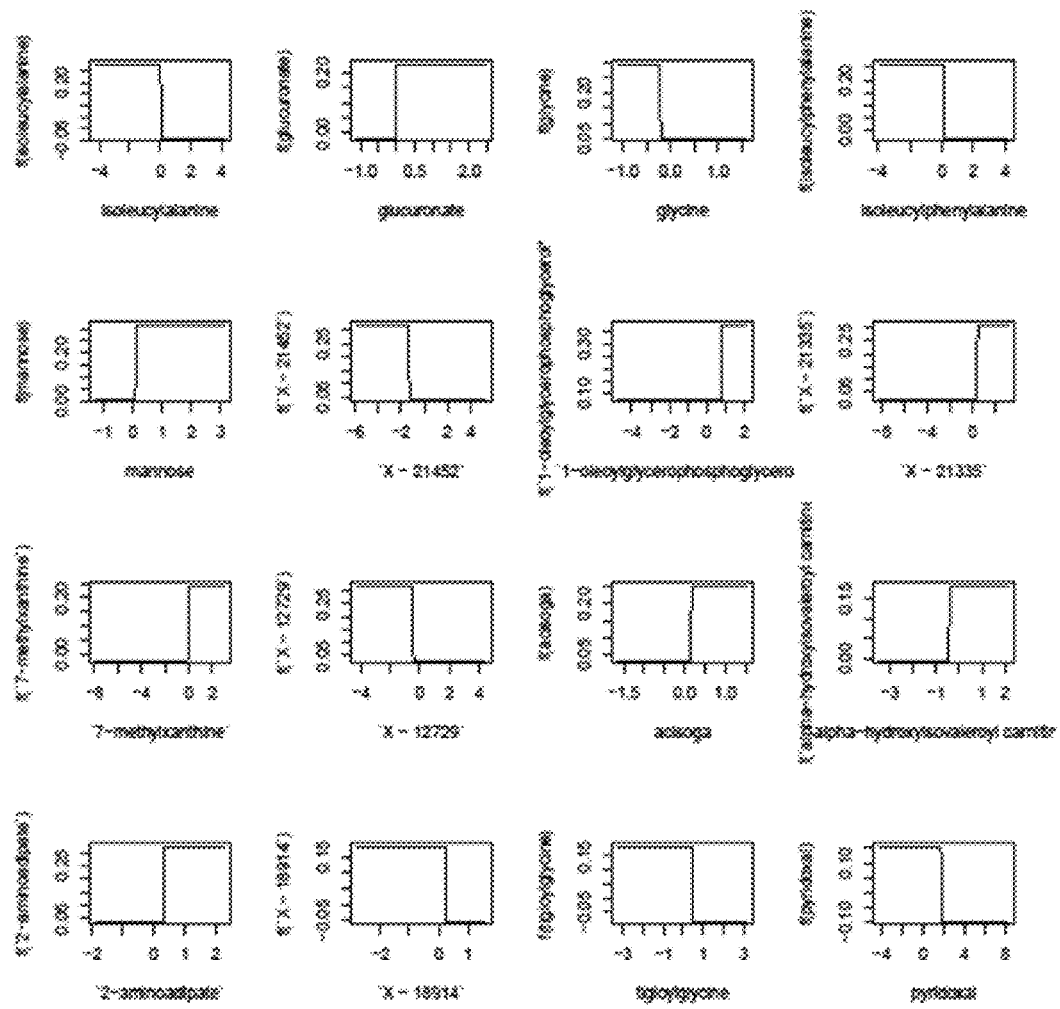
FIG. 21 is a series of graphs that provide Partial Dependence Plots for the sixteen clinical variables for Metabolomics Model of All CAD.
Figure 22:
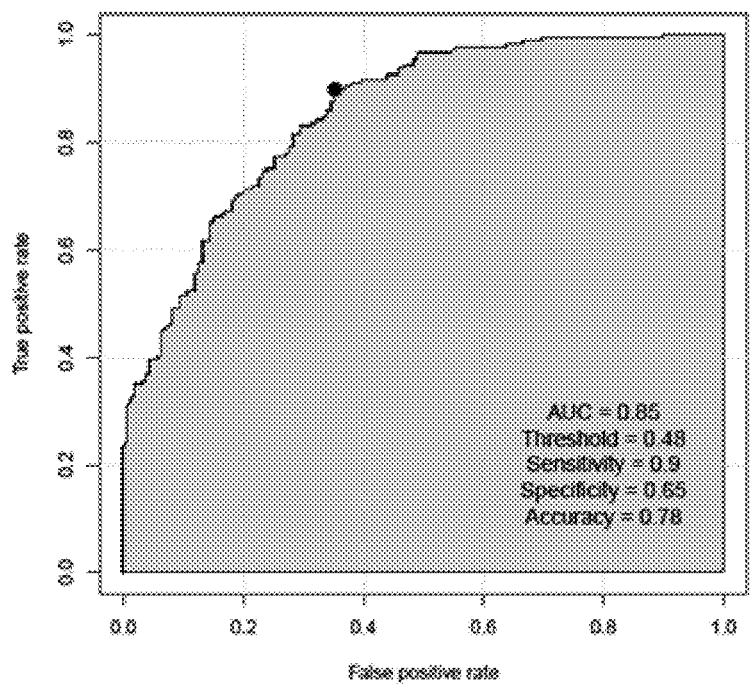
FIG. 22 is a graph demonstrating a ROC curve for Metabolomics Model of All CAD (AUC=0.85; Threshold=0.48; Sensitivity=0.9; Specificity=0.65; Accuracy=0.78).

Of the 138 clinical variables exhibiting a nominal univariate association for All CAD, a panel of sixteen metabolomic variables were predictive for probability of CAD. Table 20 provides the relative influence of the sixteen clinical variables for the Metabolomics Model of Native CAD. FIG. 21 provides Partial Dependence Plot for sixteen clinical variables for Metabolomics Model of All CAD. FIG. 22 provides a ROC curve for the Metabolomics Model of All CAD.

TABLE 20

| Variable | Relative Influence | Direction of Change |
|---|---|---|
| isoleucylalanine | 9.75 | Decreased |
| glucuronate | 8.31 | Elevated |
| glycine | 8.11 | Decreased |
| isoleucylphenylalanine | 7.69 | Decreased |
| mannose | 7.65 | Elevated |
| 'X-21452' | 6.93 | Decreased |
| '1-oleoylglycerophosphoglycerol' | 6.50 | Elevated |
| 'X-21335' | 5.94 | Elevated |
| '7-methylxanthine' | 5.77 | Elevated |
| 'X-12729' | 5.46 | Decreased |
| acisoga | 5.46 | Elevated |
| 'alpha-hydroxyisovaleroyl carnitine' | 5.11 | Elevated |
| '2-aminoadipate' | 4.80 | Elevated |
| 'X-18914' | 4.78 | Decreased |
| tigloylglycine | 4.16 | Decreased |
| pyridoxal | 3.56 | Decreased |

Clinical-Metabolomic Model

Figure 23:
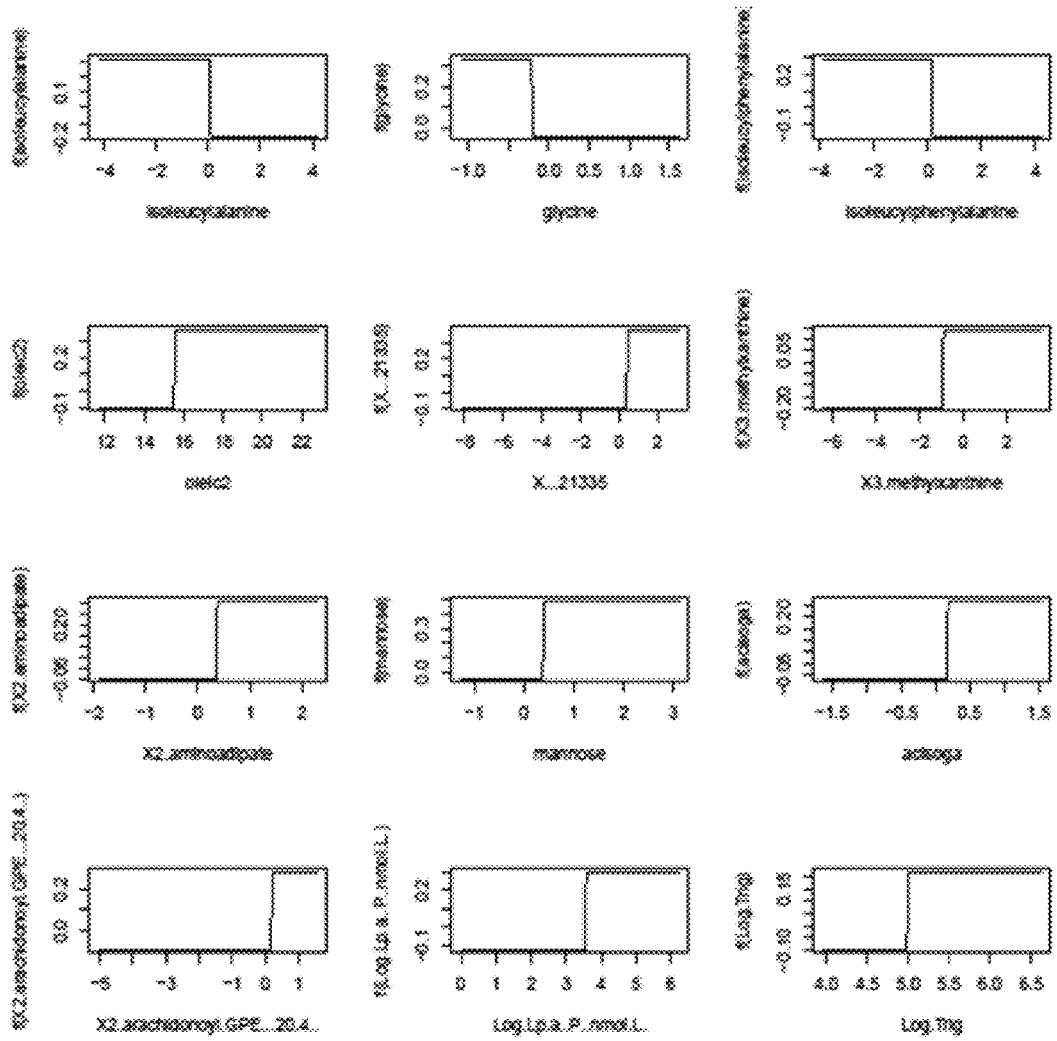
FIG. 23 is a series of graphs that provide Partial Dependence Plots for the twelve clinical variables for Clinical-Metabolomics Model of All CAD.
Figure 24:
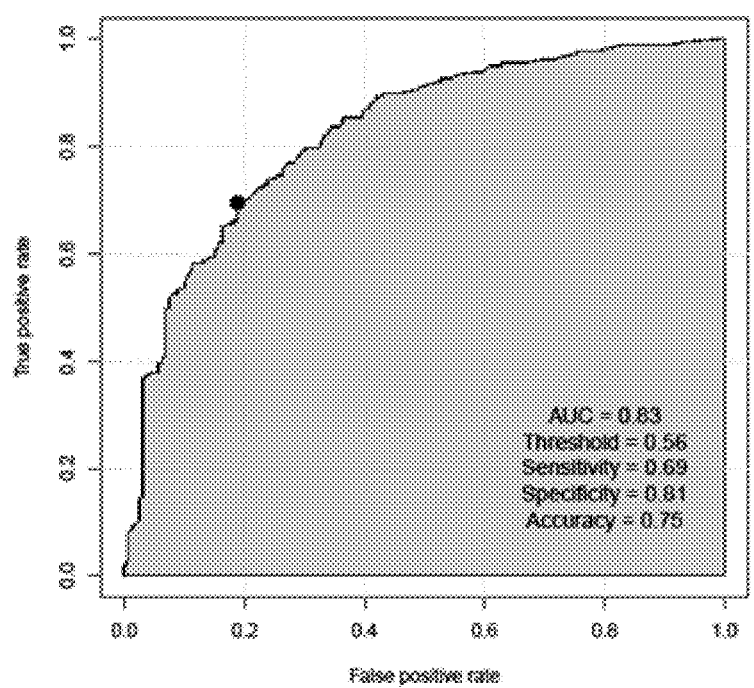
FIG. 24 is a graph demonstrating a ROC curve for the Clinical-Metabolomic Model of All CAD (AUC=0.83; Threshold=0.56; Sensitivity=0.69; Specificity=0.81; Accuracy=0.75).

A panel of twelve clinical variables were predictive for probability of CAD in the Clinical-Metabolomic Model for All CAD. Table 21 provides the relative influence of the twelve clinical variables for the Clinical-Metabolomic Model of All CAD and FIG. 23 provides Partial Dependence Plots for the twelve clinical variables for Clinical-Metabolomic Model of All CAD. FIG. 24 provides a ROC curve for the Clinical-Metabolomic Model of All CAD.

TABLE 21

| Variable | Relative Influence | Direction of Change |
|---|---|---|
| isoleucylalanine | 12.92 | Decreased |
| glycine | 10.75 | Decreased |
| isoleucylphenylalanine | 10.15 | Decreased |
| oleic2 | 9.55 | Elevated |
| X-21335 | 8.22 | Elevated |
| X3.methylxanthine | 7.97 | Elevated |
| X2.aminoadipate | 7.76 | Elevated |
| mannose | 7.28 | Elevated |
| acisoga | 6.73 | Elevated |
| X2.arachidonoyl.GPE..20.4.. | 6.51 | Elevated |
| Log.Lp.a..P..nmol.L. | 6.16 | Elevated |
| Log.Trig | 6.01 | Elevated |

Lipidomics Model 31 lipidomic variables exhibited a nominal univariate association (raw p<0.05) for All CAD. Table 22 provides a filtered list of the 29 lipidomic variables for All CAD.

TABLE 22

| | | | | |
|---|---|---|---|---|
| CE16:0 | DG18:0 | DHC18:1 | DHC26:1 | PL24:0 |
| CE16:1n7 | DG18:1n9 | DHC20:0 | FA14:1n5 | SM18:0 |
| CE18:1n9 | DG20:0 | DHC20:1 | PL15:0 | TG15:0 |
| CE18:2n6 | DG20:2n6 | DHC22:1 | PL18:2n6 | TG20:3n9 |
| CE20:4n6 | DG20:3n9 | DHC24:1 | PL20:3n9 | Total Diacylglycerol |
| CER18:0 | DHC18:0 | DHC26:0 | PL20:4n6 | Total Triacylglycerol |
| CER18:1 | | | | |

Figure 25:
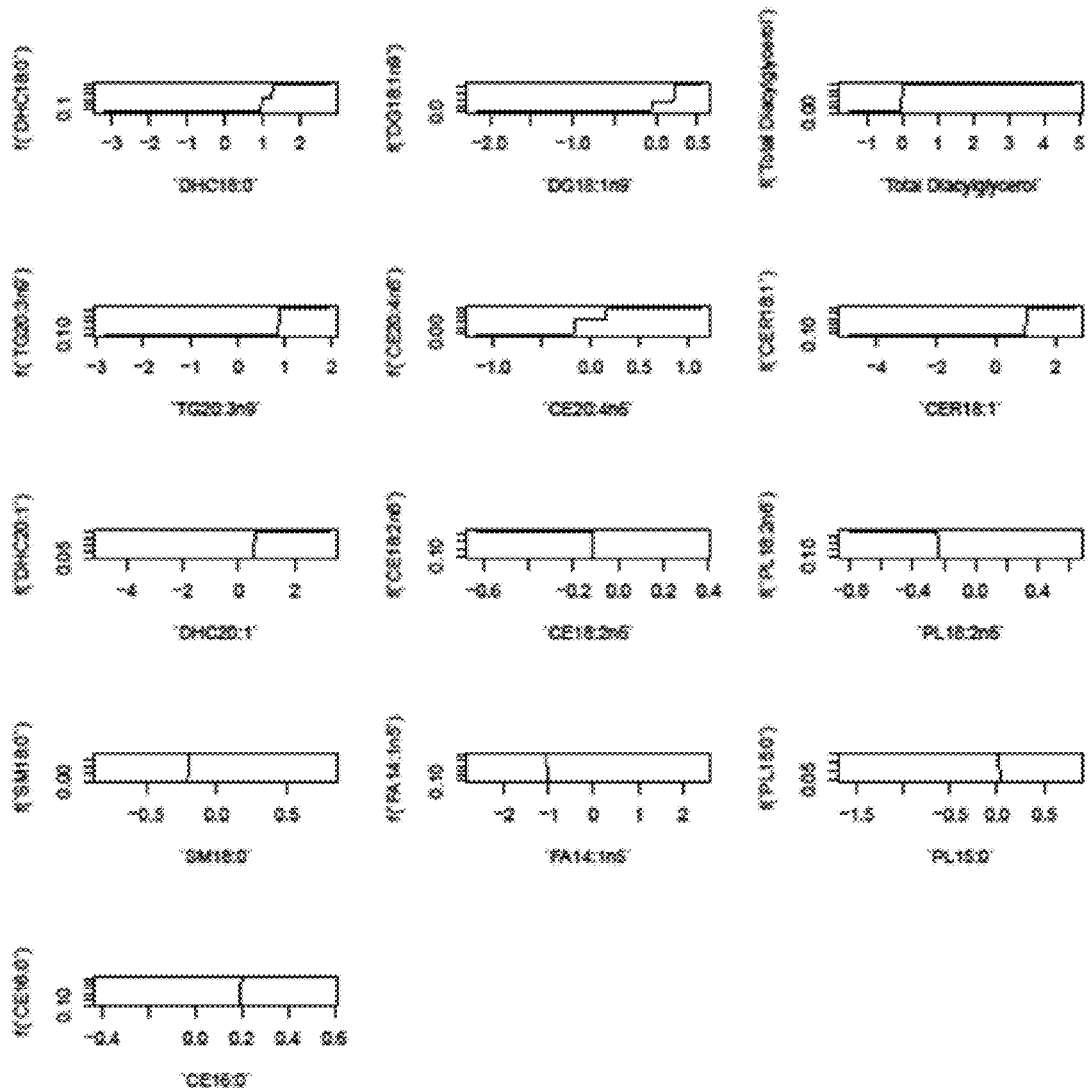
FIG. 25 is a series of graphs that provide Partial Dependence Plots for the thirteen clinical variables for Lipidomics Model of All CAD.
Figure 26:
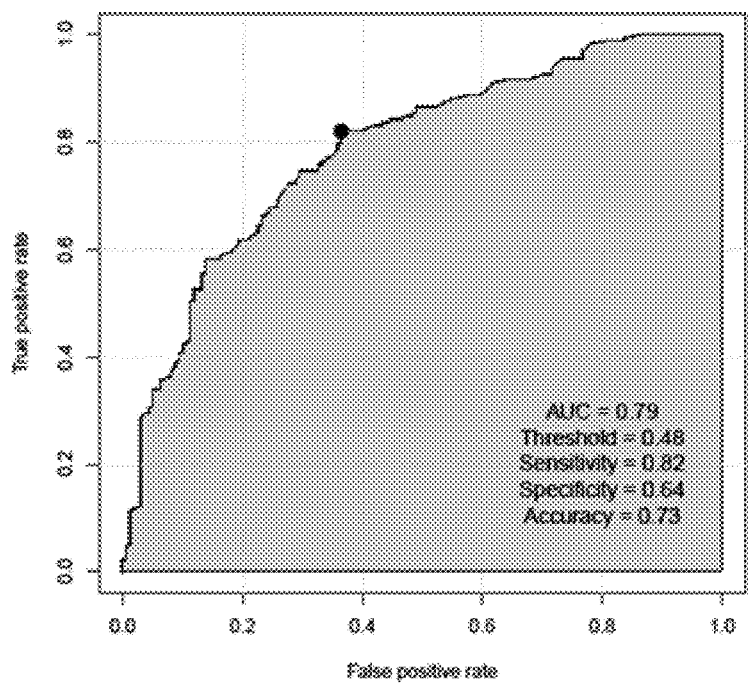
FIG. 26 is a graph demonstrating a ROC curve for Lipidomic Model of All CAD (AUC=0.79; Threshold=0.48; Sensitivity=0.82; Specificity=0.64; Accuracy=0.73).

A panel of thirteen variables were predictive for probability of CAD. Table 23 provides the relative influence of the thirteen lipidomic variables for the Lipidomics Model of All CAD. FIG. 25 provides Partial Dependence Plots for thirteen clinical variables for Lipidomics Model of All CAD. FIG. 26 provides a ROC curve for the Lipidomics Model of All CAD.

TABLE 23

| Variable | Relative Influence | Direction of Change |
|---|---|---|
| 'DHC18:0' | 14.54 | Elevated |
| 'DG18:1n9' | 12.23 | Elevated |
| 'Total Diacylglycerol' | 11.50 | Elevated |
| 'TG20:3n9' | 8.14 | Elevated |
| 'CE20:4n6' | 7.92 | Elevated |
| 'CER18:1' | 7.45 | Elevated |
| 'DHC20:1' | 7.28 | Elevated |
| 'CE18:2n6' | 6.24 | Decreased |
| 'PL18:2n6' | 5.97 | Decreased |
| 'SM18:0' | 5.34 | Elevated |
| 'FA14:1n5' | 5.31 | Decreased |
| 'PL15:0' | 4.66 | Decreased |
| 'CE16:0' | 3.41 | Elevated |

Clinical-Lipidomic Model

Figure 27:
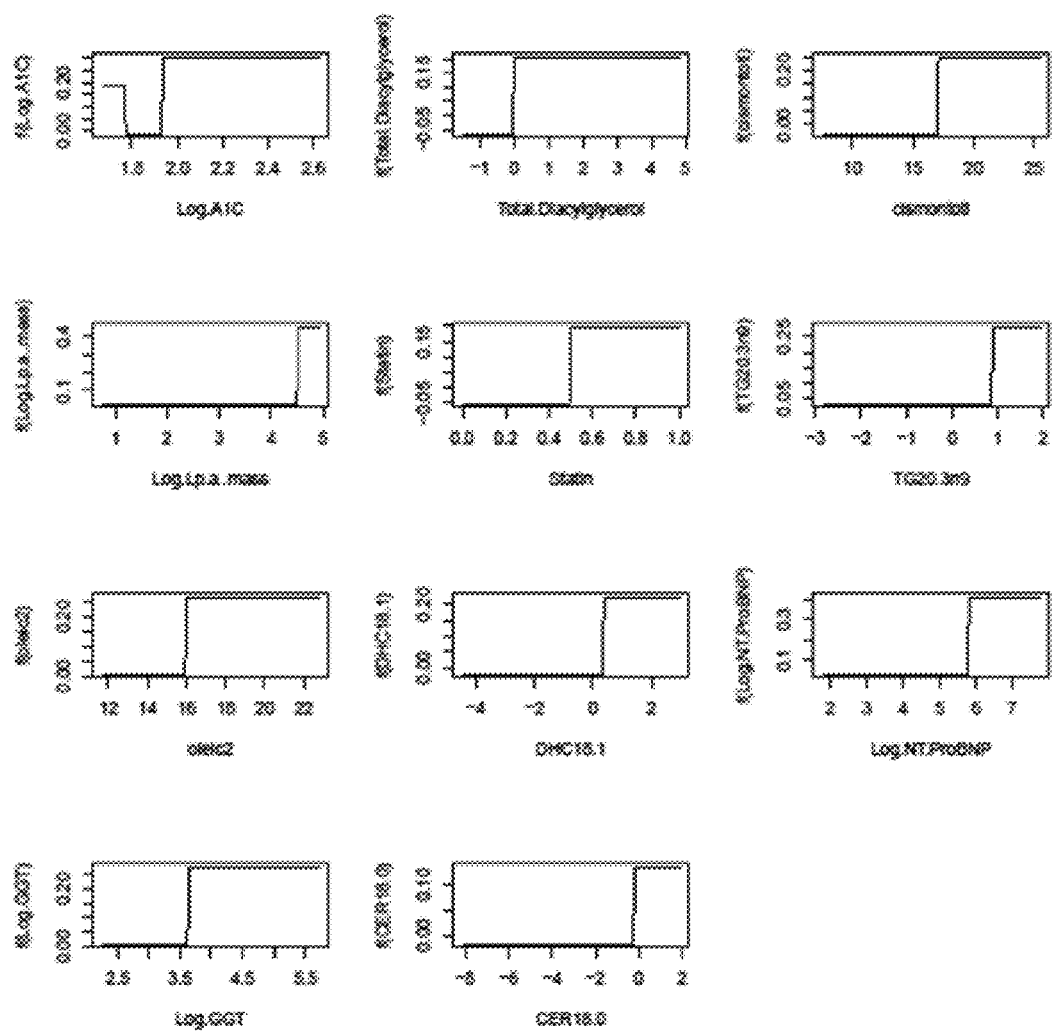
FIG. 27 is a series of graphs that provide Partial Dependence Plots for the eleven clinical variables for Clinical Lipidomics Model of All CAD.
Figure 28:
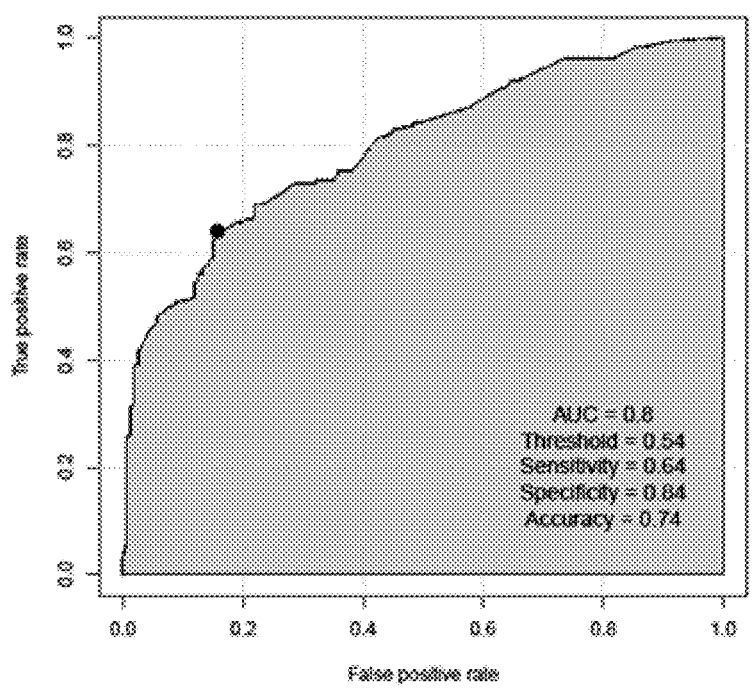
FIG. 28 is a graph demonstrating a ROC curve for the Clinical-Lipidomic Model of All CAD (AUC=0.8; Threshold=0.54; Sensitivity=0.64; Specificity=0.84; Accuracy=0.74).

A panel of eleven clinical variables were predictive for probability of CAD in the Clinical-Lipidomic Model for All CAD. Table 24 provides the relative influence of those eleven clinical variables for the Clinical-Lipidomics Model of All CAD. FIG. 27 provides Partial Dependence Plot for the eleven clinical variables for Clinical-Lipidomics Model of All CAD. FIG. 28 provides a ROC curve for the Clinical-Lipidomic Model of All CAD.

TABLE 24

Relative influence for Clinical-Lipidomic Model of All CAD

| Variable | Relative Influence | Direction of Change |
|---|---|---|
| Log.A1C | 15.78 | Decreased below a cutpoint and Elevated over another cutpoint represents risk |
| Total.Diacylglycerol | 11.49 | Elevated |
| cismontotl | 11.08 | Elevated |
| Log.Lp.a..mass | 9.27 | Elevated |
| Statin | 8.99 | Elevated |
| TG20.3n9 | 8.13 | Elevated |
| oleic2 | 7.67 | Elevated |
| DHC18.1 | 7.47 | Elevated |
| Log.NT.ProBNP | 7.12 | Elevated |
| Log.GGT | 6.68 | Elevated |
| CER18.0 | 6.32 | Elevated |

Clinical-Metabolomic-Lipidomic Model

Figure 29:
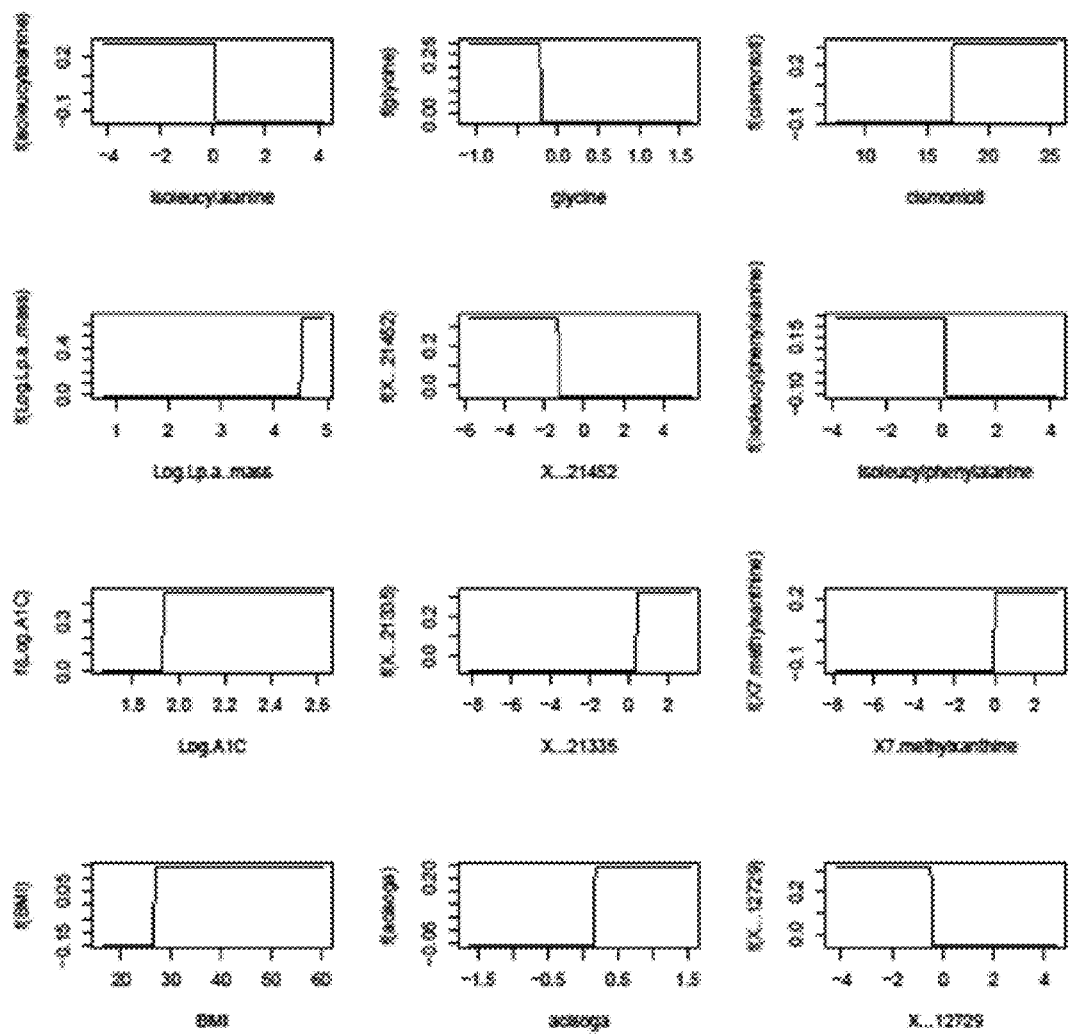
FIG. 29 is a series of graphs that provide Partial Dependence Plots for the twelve clinical variables for Clinical-Metabolomic-Lipidomic Model of All CAD.
Figure 30:
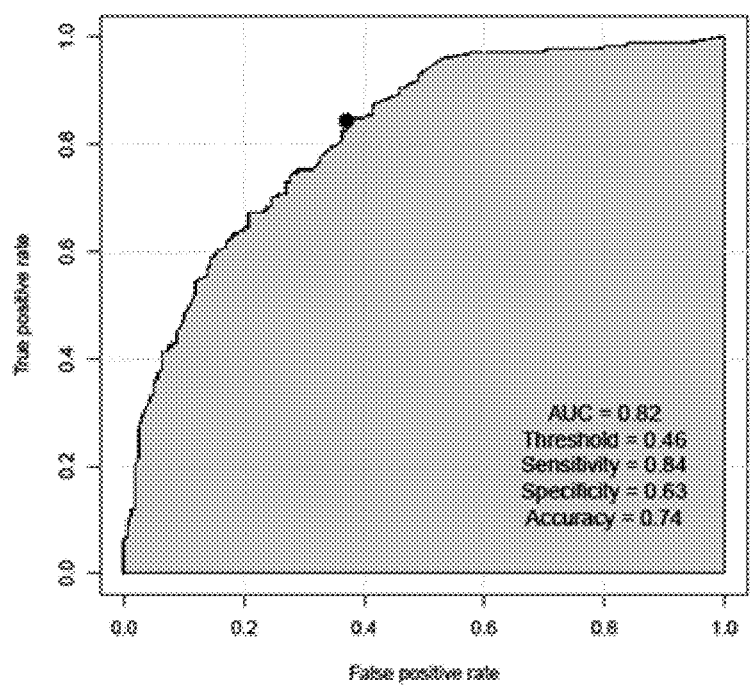
FIG. 30 is a graph demonstrating a ROC curve for the Clinical-Metabolomics-Lipidomic Model of All CAD (AUC=0.82; Threshold=0.46; Sensitivity=0.84; Specificity=0.63; Accuracy=0.74).

A panel of twelve clinical variables were predictive for probability of CAD in the Clinical-Metabolomic-Lipidomic Model of All CAD. Table 25 provides the relative influence of the twelve variables for the Clinical-Metabolomic-Lipidomic Model of All CAD. FIG. 29 provides Partial Dependence Plots for the twelve clinical variables for Clinical-Metabolomic-Lipidomic Model of All CAD. FIG. 30 provides a ROC curve for the Clinical-Metabolomic-Lipidomic Model of Native CAD.

TABLE 25

| Variable | Relative Influence | Direction of Change |
|---|---|---|
| isoleucylalanine | 12.49 | Decreased |
| Glycine | 10.39 | Decreased |

TABLE 25-continued

| Variable | Relative Influence | Direction of Change |
| --- | --- | --- |
| Cismontotl | 9.55 | Elevated |
| Log.Lp.a..mass | 9.01 | Elevated |
| X-21452 | 8.82 | Decreased |
| isoleucylphenylalanine | 7.81 | Decreased |
| Log.A1C | 7.59 | Elevated |
| X-21335 | 7.49 | Elevated |
| X7.methylxanthine | 7.12 | Elevated |
| BMI | 7.10 | Elevated |
| acisoga | 6.83 | Elevated |
| X-12729 | 5.79 | Decreased |

Throughout the examples described herein, a number of analytes are identified as "X-" compounds. The several X-compound are described in further detail in Table 26.

TABLE 26

| name | lib_id | comp_id | quant_mass | rt | tentative details of unnamed metabolites, if available | spectra |
| --- | --- | --- | --- | --- | --- | --- |
| X-12212 | LC/MS Neg | 46358 | 229.01793 | 3.47 | sulfated | 56.99574:5.1 59.98531:1 60.99317:0.6 68.99663:0.8 79.95761:13 80.96536:2 93.03481:0.3 108.02196:0.8 121.06626:0.2 122.03769:1.9 122.96783:0.7 130.04274:0.3 131.05064:0.5 134.03756:0.2 140.9786:0.5 147.04556:2.2 148.05347:3.8 149.06116:100 150.06449:11.1 162.9604:0.2 166.95785:0.4 184.96803:0.4 188.9398:2.5 206.95033:1.5 229.01806:0.7 |
| X-12472 | LC/MS Neg | 46628 | 241.11935 | 2.38 | | 58.0299:7.8 59.014:0.8 67.0304:3.4 72.00935:3.9 72.99325:1.2 74.0249:14.5 82.03117:6 84.0456:29.5 86.02505:3.2 95.05055:1 97.0409:3.2 98.02495:4 99.05655:4 101.0721:17.3 107.0253:3.5 109.0408:33.5 112.0771:1.1 125.0357:13.6 127.0514:95.7 128.03545:38.2 128.05505:5.6 145.062:100 146.06585:4.4 |
| X-12524 | LC/MS Neg | 46621 | 205.1599 | 5.54 | | 189.12873:8.1 190.13217:1.1 205.16003:100 206.16342:18.1 |
| X-12544 | LC/MS Pos | 34112 | 211.0962 | 4.25 | C11H14O4 | 53.0391:1 55.0183:0.9 55.05465:0.1 57.03405:0.2 65.0389:1.5 66.0445:0.2 67.05455:1 77.03865:1.3 78.0465:1.1 79.0544:11.9 80.05987:0.5 81.03375:0.1 81.06995:0.2 90.04655:0.2 91.05435:15.9 92.05913:0.9 93.07015:1.4 95.0493:7.3 95.08605:0.3 96.05265:0.4 103.0544:10.1 104.05735:1.1 105.0337:0.5 105.0448:1.2 105.07005:27.5 106.0414:0.6 106.07335:3.1 107.0494:0.8 107.0793:0.2 107.0859:0.2 108.05715:2.7 109.06545:1.5 115.0544:0.5 117.07:0.5 118.04135:0.8 119.04965:0.8 120.05715:4.8 121.02855:0.4 121.0651:11.8 122.0319:0.5 122.06715:0.9 123.0808:1.3 133.065:1.5 133.0841:2.2 134.0904:49.5 135.04445:0.8 135.081:8.4 135.0966:24.5 136.05205:1.2 136.08425:0.9 137.0598:0.1 139.0754:0.8 149.0235:1.4 149.0601:0.8 149.0793:0.1 150.027:3.5 150.0678:7.8 150.0853:1 151.0756:100 152.0789:10.6 152.09625:0.4 165.0912:44.2 166.09455:5.4 193.0861:2.2 194.0897:0.3 |

TABLE 26-continued

| name | lib_id | comp_id | quant_mass | rt | tentative details of unnamed metabolites, if available | spectra |
|---|---|---|---|---|---|---|
| X-12824 | LC/MS Neg | 46471 | 243.13513 | 2.72 | | 56.99603:4 58.02977:8.1 59.0142:1 61.98863:2.7 67.0303:1.4 74.02507:5.4 74.99407:1.4 79.9578:1 82.03013:3.6 83.05065:0.8 83.0618:4.6 84.0457:12.3 92.9294:1.9 97.066:3.4 101.07217:12.2 109.0408:14.8 110.0447:0.8 113.0973:0.8 114.09257:100 115.0766:1.1 115.09597:7.3 125.03593:2.4 127.0515:39.4 128.03547:11.2 128.05517:1.4 128.1083:1.4 136.9402:1.6 145.06197:23.5 147.03285:2.3 162.05645:6.2 162.8935:1.3 164.89587:9.3 181.13493:14.6 182.1383:1.9 188.93987:2 206.9505:1.3 210.9053:1.1 242.8729:8.5 |
| X-14056 | LC/MS Pos | 46632 | 192.03254 | 0.9 | | 55.01832:1 55.93465:1.6 56.04993:2.9 57.98756:2.5 58.99541:96.7 59.99693:1.3 67.04195:1 71.01293:0.4 72.93729:1.1 73.01092:2.7 73.02854:0.5 76.02167:2.7 77.00568:1.1 85.01076:2.6 85.02846:0.6 86.99001:38.5 87.99308:1.2 88.03939:35.8 89.04262:1.2 90.94774:0.7 100.02161:100 101.00566:5.5 101.02507:4.3 105.00054:26.1 106.00399:0.6 110.98994:1.4 113.00562:1.3 118.03217:0.9 128.01649:3.4 129.00051:4.7 146.02709:40.1 147.01132:1 147.03064:2.4 175.0062:0.7 |
| X-14291 | LC/MS Pos | 46414 | 195.11274 | 2.26 | | 55.9349:30 70.06541:100 71.06908:4 98.06023:67.3 99.06351:3.7 195.11306:26.4 196.11652:3.3 |
| X-15245 | LC/MS Neg | 46661 | 233.03033 | 0.55 | | 57.03447:14.6 59.014:4.4 67.01913:3.7 71.01412:4.3 73.02963:9.6 81.03482:4 83.01418:1.7 83.05046:4.8 87.0089:10.8 94.99334:4.2 99.00891:17.3 101.02453:100 102.02798:5.2 111.00896:11.4 127.04026:4.4 127.99036:1.3 128.98645:2.7 145.00866:32.6 188.99888:6.3 233.15516:13.1 234.1583:1.9 |
| X-16129 | LC/MS Pos | 46642 | 287.65062 | 1.39 | | 55.05471:6.7 56.04994:9.1 57.05657:0.5 60.05593:9.2 68.04974:1.3 70.06546:33.3 71.06867:1.2 72.08095:72 73.08427:3.4 84.04451:100 85.02856:1 85.04719:3.9 87.05555:14 88.07577:1.7 96.04446:7.1 97.07616:0.7 102.05503:7.8 106.08634:1.4 112.08699:4.9 113.07096:3.6 114.1027:1.3 115.05029:7.7 115.08666:3.5 116.07066:11.7 127.05026:1.6 129.1023:18.8 130.09762:3.7 130.10606:1 137.59745:0.8 141.06593:7.5 142.09755:3.1 157.0973:1.1 158.09249:8.3 169.06086:6.2 175.11909:17.5 274.18752:3 331.20942:1.3 |

TABLE 26-continued

| name | lib_id | comp_id | quant_mass | rt | tentative details of unnamed metabolites, if available | spectra |
|---|---|---|---|---|---|---|
| X-17178 | LC/MS Neg | 46406 | 661.25524 | 2.31 | | 58.02997:2 60.99327:1.4 67.03042:2.4 70.03061:14.1 71.02544:6.5 72.00932:5.2 73.04091:8.8 74.02488:21.8 82.02999:23.3 83.0253:4.4 84.00973:9.5 85.04103:3.2 86.02505:3.3 94.02995:3.5 95.02522:12.2 96.00928:47.6 96.04563:4.8 97.04086:4.3 98.02489:8.3 99.0202:6.6 104.03548:12.9 109.04084:24.6 110.02489:5.7 110.03631:4.1 111.02022:4.4 111.04392:4.4 112.04059:4.4 113.03584:24.4 114.01979:10 115.08781:4.5 116.05071:7 118.06646:2.9 123.05663:11.8 124.02836:1.5 124.04055:31.7 125.03579:4 125.07224:6 127.05149:100 128.03551:44.4 128.05521:4.8 129.03898:2.5 137.03613:2.2 137.07225:83.7 138.05649:5.8 138.07584:6.3 139.01529:3.1 139.05149:12.5 141.06716:14.4 145.06521:2.2 146.06133:12.9 147.04553:2 151.08791:9 153.0671:6.1 154.09889:39.1 155.08291:2.8 155.10235:3.3 160.07707:6.5 164.07199:3 165.05452:6.2 166.06246:67.9 167.04649:32.4 167.06622:4.5 168.05006:2.4 172.07704:15.7 172.10929:2.8 181.0623:4 184.07311:34.2 185.07305:8.5 189.06719:1.9 190.08768:2.5 194.09386:3.7 222.07612:9.2 265.1308:56.4 266.13418:7.8 283.14148:8.1 |
| X-21289 (renamed as X-14465) | LC/MS Pos | 46310 | 211.14353 | 3.17 | | 53.00271:0.2 53.03908:0.3 55.01833:0.5 55.05472:0.5 55.93482:2.4 57.07036:0.5 61.03997:0.8 67.05449:0.8 68.04967:0.7 69.0701:2.3 70.06538:100 71.0624:0.3 71.06913:3.7 71.08566:0.3 72.08094:0.3 72.93724:0.6 74.95295:0.2 77.0387:0.2 79.05434:1 80.04958:0.6 81.0336:0.9 81.06996:0.7 82.06524:0.6 84.08092:0.2 86.09651:23.6 87.09881:1 90.94778:1.4 91.05433:1.2 93.06995:0.6 95.04921:2.3 95.08559:0.4 96.08085:0.3 97.06483:0.3 98.04746:0.3 98.06009:0.8 99.09154:0.2 104.95094:0.3 105.03354:4.9 105.04462:0.3 105.06992:0.9 105.93487:0.4 106.03689:0.3 109.06487:0.5 110.06012:1 112.02687:1 113.07095:0.5 114.05501:0.3 114.09139:10.1 115.09475:0.7 119.08549:0.4 121.084:0.3 125.07085:0.3 126.07878:0.6 126.12785:0.2 127.08668:1.1 135.04423:0.8 137.07117:0.7 138.05506:0.2 138.12781:11.2 139.13129:1.1 149.05985:0.9 150.08528:0.4 153.06583:1.7 154.07373:14.1 155.07773:1 155.15428:3.2 166.12275:1.4 183.14922:4.1 184.15265:0.4 194.11745:1.5 211.14404:5.7 212.14739:0.7 |

TABLE 26-continued

| name | lib_id | comp_id | quant_mass | rt | tentative details of unnamed metabolites, if available | spectra |
|---|---|---|---|---|---|---|
| X-21335 (renamed as X-16132) | LC/MS Neg | 46380 | 313.44374 | 0.95 | | 56.99582:14.9 58.02984:4.1 59.01394:1.1 59.98543:2.2 67.03042:1.4 70.03066:16.5 71.01414:2 74.02489:39.5 82.03012:33.4 84.00923:7.4 84.04569:5.6 85.04109:10.7 87.05662:1.8 91.02232:2 93.00156:1.9 94.03002:2.2 95.02524:17.5 96.00927:100 96.04572:4.5 97.01255:4.5 97.04092:1.6 98.02491:9.8 98.06135:1.5 109.04084:17.5 110.02493:4.6 110.03621:2.7 110.06129:1.7 111.0202:2 111.04401:4.3 111.05659:3.9 112.02798:3.9 112.04051:6.7 113.03583:54.1 113.0722:5 114.01982:8 114.03913:2 115.08784:5.7 123.05656:6.9 124.04057:23.7 125.03584:2.9 125.07221:6.3 127.05151:60.1 128.03553:84.9 128.05516:3.3 129.03903:5 136.04062:1.6 137.07226:70.9 138.05631:4.5 138.07575:5.3 139.0153:1.3 139.05146:9.4 141.06721:51 142.07062:3 149.03607:1.3 151.08797:4.4 153.06716:3.8 154.09886:38 155.08295:2.2 155.10235:2 162.96043:1.9 165.05463:4.7 166.06244:6.8 167.04641:13.1 172.1095:1.9 181.06215:2 183.0414:3 184.0732:3.1 185.05707:17.2 188.93964:23.8 206.95024:14.2 222.0761:6.7 223.02876:1.8 265.13086:38.6 266.13405:5.8 283.14168:4.3 |
| X-21365 | LC/MS Pos | 46410 | 160.13326 | 0.91 | | 53.03916:2.2 55.05479:100 56.05004:1.4 56.05833:4.8 57.03401:1.2 57.07041:0.7 58.06576:6.6 59.04963:26.7 59.07262:1.1 60.05298:0.7 60.08128:80.5 61.0848:2.3 67.05459:0.8 69.03384:0.6 69.07022:0.5 70.06544:0.7 71.04943:0.6 72.04467:2.2 72.93739:0.5 73.06505:1.2 83.04937:37.1 84.05268:2.1 84.08102:1.9 84.95992:1.4 87.04431:3.6 91.05443:0.6 95.08577:0.8 101.05997:86.6 101.10755:2.5 102.06325:5.1 105.0701:0.8 160.1335:35.9 161.13707:3.5 |
| X-21452 (renamed as X-02269) | LC/MS Neg | 46497 | 255.08761 | 1.49 | hydroxy metabolite of CMPF | 55.0189:100 57.03468:17.2 59.01397:19.3 71.05051:5.3 73.02978:5.6 84.02189:7.9 85.02967:47.7 86.037:28.8 93.03473:9.8 107.05039:37 109.06599:68.2 139.07662:16.6 147.08171:24 149.09737:16.6 153.05596:11.8 167.10795:23.2 211.09786:31.9 237.8701:8.4 254.91917:11.4 255.23316:50.7 256.23649:11.2 |

TABLE 26-continued

| name | lib_id | comp_id | quant_mass | rt | tentative details of unnamed metabolites, if available | spectra |
|---|---|---|---|---|---|---|
| X-21626 | LC/MS Neg | 46694 | 696.77661 | 2.4 | | 58.02983:1.8 66.03515:0.8 67.03025:2.6 68.05086:0.6 70.03052:13 71.01414:1.9 71.02533:6 72.00938:0.6 72.04573:0.6 73.04118:8.9 74.02484:2.5 80.05081:1 82.01751:1.3 82.03001:22 83.02528:4.1 83.03341:0.7 84.00975:10.7 84.04565:2 85.04097:2.3 86.02505:1.2 87.0566:1.2 88.04059:60.8 89.0437:1.8 91.05553:1.5 94.03005:2.8 94.06643:0.5 95.02526:12.4 96.0093:43.2 96.04566:4 97.01273:1.6 97.0409:2.8 98.0124:1.6 98.02495:8.3 98.06133:0.6 99.0202:6.9 99.05659:7.8 100.04064:0.9 101.07217:5.3 106.03:0.5 107.02526:1.6 108.03323:0.6 109.02861:1.4 109.04085:24.3 110.01249:0.9 110.02493:5.3 110.03632:4.1 110.04395:1.2 110.0612:1.9 111.02026:6.2 111.04409:4.8 111.05643:2.2 112.02816:1.1 112.04056:4.5 113.03584:22.1 113.07218:2.2 114.01981:9.4 114.03904:0.6 115.08788:4.2 116.05076:5.2 118.06643:3.2 121.04083:1.1 122.02497:0.6 123.05659:9.8 124.02795:1.3 124.0406:29.6 125.03585:3.8 125.04412:1.7 125.07225:6.1 127.05153:100 128.03555:38.3 128.05529:5.3 129.03913:2 130.06567:0.7 131.04677:1.1 135.05658:1.9 136.04068:1 137.03619:2 137.07226:78.8 138.05655:5.3 138.07601:5.7 139.01528:2.4 139.05147:10.5 139.08788:0.7 140.07209:0.9 140.08279:0.7 141.03084:0.9 141.0672:13.4 142.06758:1 145.06211:10.8 146.06132:11.6 147.04558:0.9 147.06506:1 149.03591:1.7 151.05172:1 151.08795:8.9 152.07198:0.9 152.08264:1 153.03092:1.3 153.06711:4.8 154.09888:37.3 155.08325:3.3 155.10263:2.7 156.0783:1.8 157.0626:1.1 158.06144:2.7 158.09379:0.7 160.07705:3.7 163.05154:1 163.08804:2 164.07197:1.2 165.05471:6.6 166.06249:50.9 167.04654:26.1 167.06708:3.4 167.08272:1.3 168.05029:1.8 171.09326:1 172.07742:0.7 172.10944:2.6 173.07229:1.5 175.08778:0.8 177.0674:1.8 180.07808:0.7 181.06225:3.1 184.0732:27.4 185.05684:1.4 185.07237:15.4 186.05647:9.5 186.07532:1.7 187.06032:0.9 188.07211:1 189.06713:2.3 193.02589:0.9 194.09383:3.8 195.07808:0.9 195.11422:1.1 201.06731:1 202.09936:2.3 203.08317:3.2 210.05257:0.7 212.1046:1 213.10414:0.6 215.08308:0.8 220.10956:1.4 222.07619:11.7 222.12498:0.9 223.0805:1.2 229.09872:1.1 |

TABLE 26-continued

| name | lib_id | comp_id | quant_mass | rt | tentative details of unnamed metabolites, if available | spectra |
|---|---|---|---|---|---|---|
| X- 21662 | LC/MS Pos | 46731 | 510.35583 | 5.62 | 15-methylpalmitoyl-GPC | 231.11421:5.9 232.11622:1 238.08375:1.9 238.12027:1.2 243.11435:1.3 248.10805:1.3 256.11026:1.9 265.13091:53.2 266.13433:7.5 274.11996:1.7 276.10381:1 283.14159:7.7 284.14486:1 292.1308:0.9 313.13127:7.1 314.13535:0.9 331.14176:2.3 53.0027:0.7 55.0547:2.7 56.0499:4.1 56.96523:0.4 57.03436:1.2 57.0703:7.3 58.06545:2.8 58.07365:0.2 59.04953:3.2 59.0734:0.6 60.08115:36.5 61.08445:1.2 65.0389:0.2 67.05448:3.6 69.0701:2.1 70.06533:0.7 71.0731:22.1 71.0857:3.2 72.07738:0.7 73.0285:1.4 79.05432:1.4 81.07:3.3 83.08558:1.2 85.10112:1.2 86.09653:100 87.04413:0.5 87.09423:0.3 87.0998:4.8 89.05973:1.8 91.05425:1.3 93.06997:1.3 95.0492:0.2 95.0856:3.1 96.0889:0.2 97.10122:0.6 98.98423:17.9 104.10703:73.8 105.06988:1.1 105.11032:3.7 107.08547:0.5 109.10108:1 119.0854:1 124.9999:65.1 126.0032:1.3 131.08543:0.4 133.10083:0.3 143.01033:0.3 163.01535:0.3 184.07342:44 185.07693:2.2 |

For Table 26, the data is in the following format: name; lib_id; comp_id; quant_mass; rt; tentative details of unnamed metabolites, if available; and spectra. The spectra data format (x:y) indicates the mass of the ion (m/z=x) and relative peak intensity (y). Each ion in the spectra is separated by a space.

Methods: Univariate Analysis of Secondary Endpoints

Example 2. Discovery and Validation

Analysis Populations

The "Discovery-Full Analysis Set" ("Discovery FAS") consisted of pilot study patients with clinical data and a CT-based designation of either Revascularization CAD case, Native CAD case, or Control (N=748 for the Discovery-FAS group).

The "Discovery-Native CAD Set" was the subset of the Discovery-FAS with Native CAD as verified by CT, who had analyte (metabolomic) data (N=366 for the Discovery-Native CAD Set). These were subjects without previous revascularization procedures, such as percutaneous coronary intervention (PCI) or coronary artery bypass grafting (CABG).

The "Discovery-Revasc CAD Set" was the subset of the Discovery-FAS who had undergone previous revascularization, such as percutaneous coronary intervention (PCI) or coronary artery bypass grafting (CABG), and who had analyte data (N=44).

The "Discovery-All CAD Set" was the union of the Discovery-Native CAD Set and the Discovery-Revasc CAD Set (N=410).

The "Discovery-Control Set" was the subset of Discovery-FAS who had a calcium score of zero and were designated a Control after inspection of CT data, and who had analyte data. (N=338 for the Discovery-Control Set.)

The "Validation-Full Analysis Set" ("Validation-FAS") consisted of pilot study patients with clinical data and a CT-based designation of either Revascularization CAD case, Native CAD case, or Control (N=348 for the Validation-FAS group).

The "Validation-Native CAD Set" was the subset of the Validation-FAS with Native CAD as verified by CT, who had analyte (metabolomic) data (N=207 for the Validation-Native CAD Set). These were subjects without previous revascularization procedures, such as percutaneous coronary intervention (PCI) or coronary artery bypass grafting (CABG).

The "Validation-Revasc CAD Set" was the subset of the Validation-FAS who had undergone previous revascularization, such as percutaneous coronary intervention (PCI) or coronary artery bypass grafting (CABG), and who had analyte data (N=15).

The "Validation-All CAD Set" was the union of the Validation-Native CAD Set and the Validation-Revasc CAD Set (N=222).

The "Validation-Control Set" was the subset of Validation-FAS who had a calcium score of zero and were designated a Control after inspection of CT data, and who had analyte data. (N=126 for the Validation-Control Set)

It is noted that by design, the only racial group represented in the study was White. Therefore, race-based subpopulations were not defined.

A. Study Endpoints

For the GLOBAL Pilot Discovery Cohort, there were four primary endpoints in the analysis: (1) Native CAD; (2) All CAD (Native or Revascularization); (3) 50% Stenosis without Revascularization; (4) 50% Stenosis or Revascularization. All analyses were applied to all primary endpoints.

B. Statistical Hypothesis

The null hypothesis of no association, between the metabolite or lipid and the endpoint, was tested against the two-sided alternative that association exists.

C. Multiple Comparisons and Multiplicity

False discovery rate (FDR) q-values were calculated (Benjamini and Hochberg, 1995). Associations with FDR q<0.05 were considered preliminary associations. In some circumstances, test results with raw p<0.05 were reported as well.

D. Missing Data

Endpoint data was not imputed. Potential covariates with more than 5% missing data were excluded. Potential covariates with less than 5% missing data were imputed to the mean.

Metabolites with more than 10% missing data were excluded from the main analyses. Missing values for metabolites and lipids with less than 10% missing were imputed to the observed minimum after normalization.

E. Analysis of Subgroups

Figure 50:
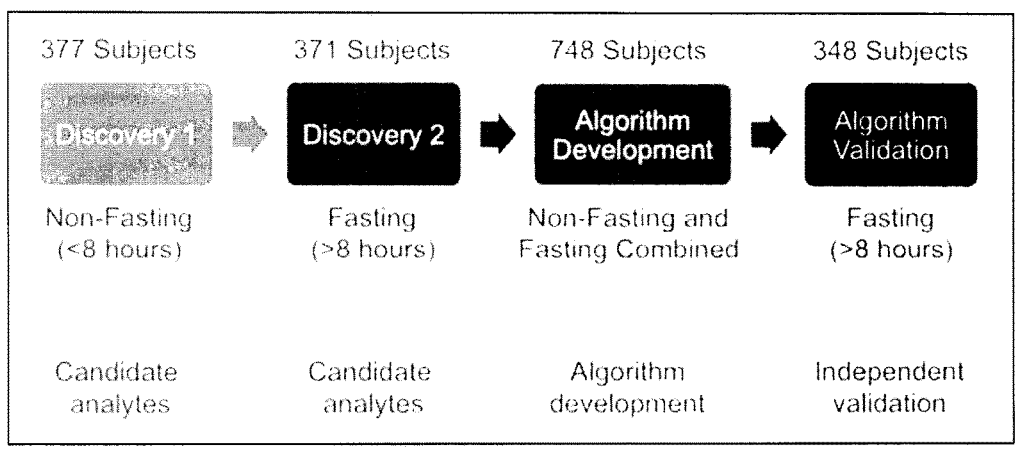
FIG. 50 is a schematic diagram describing the development and validation of an algorithm for a subset of the "Full Analysis Set" (FAS) group based on participants' fasting status.

The first and third primary endpoints were addressed using a subset of the FAS. Specifically the Native CAS Set and the Control Set were considered to the exclusion of the Revasc. CAD Set. For the purposes of discovery, further subsets were created on the basis of participants' fasting status, where patients were categorized as Fasting if they had not eaten for eight or more hours. The remainder, either known not to be fasted, or with unknown fasting status were categorized as 'Non-Fasting'. See FIG. 50.

I. Demographic and Baseline Characteristics

The baseline and demographic characteristics of patients in the pilot study were tabulated. Continuous variables were summarized by the mean and standard error; binary variables were summarized by the count and percentage.

Table 27 shows general patient characteristics for the Discovery Set by clinical group (Revasc CAD vs. Native CAD vs. Control). A Kruskall-Wallis test was performed to investigate homogeneity of continuous measures; a Pearson's chi-squared test was conducted for binary measures; unadjusted p-values are reported.

Table 28 shows general patient characteristics for the Validation Set by clinical group (Revasc CAD vs. Native CAD vs. Control). A Kruskall-Wallis test was performed to investigate homogeneity of continuous measures; a Pearson's chi-squared test was conducted for binary measures; unadjusted p-values are reported.

TABLE 27

|  | All Controls | Native CAD | Revasc CAD | P-value |
|---|---|---|---|---|
| N | 338 | 366 | 44 | |
| Age | | | | |
| mean (SE) | 53.8 (0.57) | 58.02 (0.54) | 59.55 (1.40) | 3.93E−07 |
| SBP | | | | |
| mean (SE) | 129.62 (0.91) | 132.6 (0.92) | 128.09 (2.32) | 0.0550 |
| DBP | | | | |
| mean (SE) | 79.03 (0.56) | 79.73 (0.58) | 75.12 (1.57) | 0.0402 |
| Male | | | | |
| N (%) | 151 (44.67) | 195 (53.28) | 30 (68.18) | 0.0037 |
| Hypertension | | | | |
| N (%) | 172 (51.04) | 244 (66.85) | 40 (90.91) | 1.61E−08 |
| Dyslipidemia | | | | |
| N (%) | 184 (55.42) | 259 (71.15) | 43 (100.00) | 4.95E−10 |
| Diabetes (Any) | | | | |
| N (%) | 25 (7.40) | 54 (14.75) | 10 (22.73) | 8.00E−04 |
| Type I Diabetes | | | | |
| N (%) | 1 (0.30) | 1 (0.27) | 0 (0.00) | 0.9377 |
| Type II Diabetes | | | | |
| N (%) | 24 (7.10) | 53 (14.48) | 10 (22.73) | 6.00E−04 |
| Current Smoker | | | | |
| N (%) | 39 (11.54) | 67 (18.31) | 5 (11.36) | 0.0331 |
| Former Smoker | | | | |
| N (%) | 84 (24.85) | 130 (35.52) | 21 (47.73) | 5.00E−04 |
| Chest Pain | | | | |
| N (%) | 221 (65.38) | 212 (57.92) | 30 (68.18) | 0.0850 |
| Angina Equivalent | | | | |
| N (%) | 126 (37.28) | 122 (33.33) | 19 (43.18) | 0.3115 |
| Shortness of Breath | | | | |
| N (%) | 74 (21.89) | 71 (19.40) | 8 (18.18) | 0.6635 |

TABLE 27-continued

|  | All Controls | Native CAD | Revasc CAD | P-value |
| --- | --- | --- | --- | --- |
| Family History of CAD N (%) | 179 (52.96) | 223 (60.93) | 28 (63.64) | 0.0710 |
| Fasting N (%) | 120 (35.50) | 207 (56.56) | 44 (100.00) | 8.28E−18 |
| Statin N (%) | 111 (32.84) | 184 (50.27) | 38 (86.36) | 1.28E−12 |
| Niacin N (%) | 5 (1.48) | 4 (1.09) | 3 (6.82) | 0.0164 |
| Fibrate N (%) | 12 (3.55) | 21 (5.74) | 3 (6.82) | 0.3254 |
| Ezetimibe N (%) | 6 (1.78) | 11 (3.01) | 8 (18.18) | 7.97E−08 |
| Fish Oil N (%) | 26 (7.69) | 50 (13.66) | 5 (11.36) | 0.0388 |
| Bile Acid Sequestrant N (%) | 3 (0.89) | 4 (1.09) | 0 (0.00) | 0.7705 |
| Aspirin N (%) | 98 (28.99) | 157 (42.90) | 34 (77.27) | 3.15E−10 |
| Clopidogrel N (%) | 7 (2.07) | 11 (3.01) | 15 (34.09) | 5.21E−22 |
| Vitamin K Antagonist N (%) | 7 (2.07) | 17 (4.64) | 2 (4.55) | 0.1629 |
| Nitrate N (%) | 7 (2.07) | 16 (4.37) | 11 (25.00) | 5.57E−11 |
| Beta Blocker N (%) | 114 (33.73) | 140 (38.25) | 34 (77.27) | 1.68E−07 |
| ACE Inhibitor N (%) | 63 (18.64) | 106 (28.96) | 24 (54.55) | 3.13E−07 |

TABLE 28

|  | All Controls | Native CAD | Revasc CAD | P-value |
| --- | --- | --- | --- | --- |
| N | 126 | 207 | 15 |  |
| Age mean (SE) | 49.48 (0.93) | 60.83 (0.59) | 68.6 (2.05) | 3.35E−22 |
| SBP mean (SE) | 127.25 (1.55) | 131.46 (1.10) | 131.8 (4.16) | 0.0276 |
| DBP mean (SE) | 77.33 (0.98) | 78.99 (0.77) | 78.87 (3.16) | 0.2091 |
| Male N (%) | 46 (36.51) | 138 (66.67) | 15 (100.00) | 1.36E−09 |
| Hypertension N (%) | 51 (40.48) | 132 (63.77) | 13 (86.67) | 9.44E−06 |
| Dyslipidemia N (%) | 65 (53.72) | 152 (74.88) | 14 (100.00) | 1.33E−05 |
| Diabetes (Any) N (%) | 12 (9.52) | 44 (21.36) | 4 (26.67) | 0.0134 |
| Type I Diabetes N (%) | 1 (0.79) | 3 (1.45) | 1 (6.67) | 0.1954 |
| Type II Diabetes N (%) | 11 (8.73) | 41 (19.81) | 3 (20.00) | 0.0244 |

TABLE 28-continued

|  | All Controls | Native CAD | Revasc CAD | P-value |
|---|---|---|---|---|
| Current Smoker | | | | |
| N (%) | 20 (15.87) | 28 (13.53) | 0 (0.00) | 0.238 |
| Former Smoker | | | | |
| N (%) | 25 (19.84) | 78 (37.68) | 8 (53.33) | 6.00E-04 |
| Chest Pain | | | | |
| N (%) | 96 (76.19) | 110 (53.14) | 7 (46.67) | 7.78E-05 |
| Angina Equivalent | | | | |
| N (%) | 46 (36.51) | 53 (25.60) | 5 (33.33) | 0.1037 |
| Shortness of Breath | | | | |
| N (%) | 28 (22.22) | 30 (14.49) | 7 (46.67) | 0.0038 |
| Family History of CAD | | | | |
| N (%) | 53 (42.06) | 129 (62.32) | 6 (40.00) | 8.00E-04 |
| Fasting | | | | |
| N (%) | 126 (100.00) | 207 (100.00) | 15 (100.00) | NA |
| Statin | | | | |
| N (%) | 39 (30.95) | 125 (60.39) | 13 (86.67) | 2.28E-08 |
| Niacin | | | | |
| N (%) | 1 (0.79) | 3 (1.45) | 0 (0.00) | 0.7872 |
| Fibrate | | | | |
| N (%) | 4 (3.17) | 7 (3.38) | 1 (6.67) | 0.7797 |
| Ezetimibe | | | | |
| N (%) | 1 (0.79) | 5 (2.42) | 0 (0.00) | 0.4745 |
| Fish Oil | | | | |
| N (%) | 8 (6.35) | 23 (11.11) | 1 (6.67) | 0.3251 |
| Bile Acid Sequestrant | | | | |
| N (%) | 0 (0.00) | 0 (0.00) | 0 (0.00) | NA |
| Aspirin | | | | |
| N (%) | 28 (22.22) | 99 (47.83) | 9 (60.00) | 4.91E-06 |
| Clopidogrel | | | | |
| N (%) | 1 (0.79) | 2 (0.97) | 4 (26.67) | 3.16E-11 |
| Vitamin K Antagonist | | | | |
| N (%) | 6 (4.76) | 3 (1.45) | 1 (6.67) | 0.1432 |
| Nitrate | | | | |
| N (%) | 3 (2.38) | 10 (4.83) | 3 (20.00) | 0.0084 |
| Beta Blocker | | | | |
| N (%) | 36 (28.57) | 77 (37.20) | 12 (80.00) | 4.00E-04 |
| ACE Inhibitor | | | | |
| N (%) | 26 (20.63) | 59 (28.50) | 9 (60.00) | 0.0039 |

II. Exploratory Data Analyses for Metabolites

Sample preparation and mass spectrometry analyses were conducted by Metabolon, Inc. The raw data contained a total of 1088 analytes, measured for 1096 pilot study participants.

Of the 1088 analytes (including unnamed metabolites and complex lipids), 481 named metabolites had less than 10% missing data. All 1096 patients had less than 10% missing data for these metabolites. Statistical analyses were therefore applied to 481 analytes and 1096 patients. The data was normalized in advance of receipt. A logarithm (base 2) transformation was applied and histograms were created to show the distribution of expression by analyte (data not shown).

The metabolomics data were generated in multiple batches; however, a principal components analysis (PCA) showed no evidence of any systematic site effects.

III. Prediction Modeling for Primary Endpoints

Methods. Patients in the Discovery-FAS Set were categorized according to whether they had fasted for at least eight hours. By this criteria, a total of 377 participants were Fasted and 371 were Non-Fasted. Association testing, with adjustment for age and gender was conducted for the four primary endpoints, and nominal associations were defined in three ways as follows:

1 Significant in Fasting and Non-Fasting combined

2 Significant in Fasting and Non-Fasting independently

3 Significant in Fasting alone

It is emphasized that, at this stage, 'significant' pertains to any association with raw, unadjusted $p<0.05$.

In this way, twelve scenarios were considered as follows:
a) Atherosclerosis in Native CAD—$A^{nCAD}$
  c. Significant in Fasting & Non-Fasting Combined—$A_{FNF}^{nCAD}$
  c. Independently Significant in Fasting and Non-Fasting—$A_{IFNF}^{nCAD}$
  c. Significant in Fasting—$A_F^{nCAD}$
b) Atherosclerosis in All CAD (including revascularization)—$A^{aCAD}$
  c. Significant in Fasting & Non-Fasting Combined—$A_{FNF}^{aCAD}$
  c. Independently Significant in Fasting and Non-Fasting—$A_{IFNF}^{aCAD}$
  c. Significant in Fasting—$A_F^{aCAD}$
c) 50% stenosis in Native CAD—$S^{nCAD}$
  c. Significant in Fasting & Non-Fasting Combined—$S_{FNF}^{nCAD}$
  c. Independently Significant in Fasting and Non-Fasting—$S_{IFNF}^{nCAD}$
  c. Significant in Fasting—$S_F^{nCAD}$
d) 50% stenosis in ALL CAD (including revascularization)—$S^{aCAD}$
  c. Significant in Fasting & Non-Fasting Combined—$S_{FNF}^{aCAD}$
  c. Independently Significant in Fasting and Non-Fasting—$S_{IFNF}^{aCAD}$
  c. Analytes Significant in Fasting—$S_F^{aCAD}$.

When more than 9 variables had p<0.05, Age and Gender were added to the variables, and gradient boosting (see below) was applied to select 9 predictors.

Twelve prediction models were obtained by generalized linear (logistic) regression as follows. When fewer than nine variables had p<0.05, Age and Gender were added to the variables, and the full model was fitted. Otherwise, the nine variables selected by gradient boosting variables were combined with Age and Gender in a generalized linear (logistic) model.

Gradient boosting is an approach to determine a regression function that minimizes the expectation of a loss function. (Freidman J H (2001) and Friedman J H (2002)) It is an iterative method, in which the negative gradient of the loss function is calculated, a regression model is fitted, the gradient descent step size is selected, and the regression function is updated. The gradient is approximated by means of a regression tree, which makes use of covariate information, and at each iteration the gradient determines the direction in which the function needs to move, in order to improve the fit to the data.

The loss function was assumed Bernoulli, due to the binary nature of the primary endpoints. A learning rate ($\lambda$) was introduced to dampen proposed moves and to protect against over-fitting. The optimal number of iterations, given by T, was determined by 5-fold cross-validation. The minimum number of observations in each terminal node was 10. Two-way interactions were allowed. Random sub-sampling, without replacement, of half of the observations was applied to achieve variance reduction in gradient estimation.

For current purposes, 50 rounds of gradient boosting were run for each scenario, and the nine variables most often showing highest estimated relative influence were taken forwards to generalized linear modeling.

The twelve models were used to generate probability predictions for each patient in the Validation-FAS. For each model, the sensitivity, specificity, positive predictive value (PPV) and negative predictive value (NPV) were calculated for the range of predicted probability thresholds. A Receiver Operating Characteristic (ROC) curve was generated to plot sensitivity as a function of (1-specificity). The optimal classification threshold was determined on the basis of accuracy, defined as the proportion of correct predictions. In addition, the Area Under the Curve (AUC) and accuracy was estimated (Tables 27, 28, 29, 30 for the four primary endpoints, respectively).

The performance of model-based predictions were compared to the performance of probability predictions obtained by Diamond-Forrester scoring. (Diamond and Forrester (1979)).

Detailed Results for Native CAD

The results show that the Diamond-Forrester score provides poor prediction of the GLOBAL phenotypes (FIGS. 34, 38, 42, 46). The estimates of AUC and accuracy for prediction of Native CAD indicate that performance is no better than assigning all patients as 'at risk' of disease, by which 62% of predictions in the Validation Set for Native CAD (Validation-Native CAD plus Validation-Control) are correct, and 64% of predictions in the Validation Set for All CAD (Validation Native CAD plus Validation-Revasc. CAD plus Validation-Control), are correct.

Metabolomics Model

I. Atherosclerosis in Native CAD—$A\ n^{nCAD}$
  a. Significant in Fasting & Non-Fasting Combined—$A_{FNF}^{nCAD}$
    i. Of the 481 analytes measured, 83 metabolomic variables exhibited a nominal univariate association (raw p<0.05) for $A_{FNF}^{nCAD}$. Table 29 provides a list of the 83 metabolomic variables for $A_{FNF}^{nCAD}$.

TABLE 29

| | | |
|---|---|---|
| glutamate | serylleucine | 1-linoleoyl-GPC (18:2) |
| acisoga | 3-methoxytyrosine | 1-methylguanosine |
| threonate | prolylhydroxyproline | 12 13-DiHOME |
| urate | valerylcarnitine (C5) | O-sulfo-L-tyrosine |
| mannose | caproate (6:0) | erucamide |
| oleic ethanolamide | tigloylglycine | inositol 1-phosphate (I1P) |
| cysteine-glutathione disulfide | guanidinosuccinate | isoleucylvaline |
| pyroglutamylglutamine | isobutyrylglycine (C4) | gamma-tocopherol |
| valylleucine | glycocholenate sulfate* | 1-eicosenoylglycerophosphocholine (20:1n9)* |
| butyrylcarnitine (C4) | o-cresol sulfate | tyrosylglutamine |
| cytidine | N-acetylthreonine | indolepropionate |

TABLE 29-continued

| | | |
|---|---|---|
| palmitoyl ethanolamide | leucylglycine | gamma-glutamylvaline |
| phenylalanylvaline | 2-hydroxybutyrate (AHB) | 2-aminoadipate |
| hydroxybutyrylcarnitine* | leucylaspartate | aspartate |
| 1-nonadecanoylglycerophosphocholine (19:0) | 1-arachidoyl-GPC (20:0) | N6-carbamoylthreonyladenosine |
| glycine | N6-methyladenosine | methyl glucopyranoside (alpha + beta) |
| propionylglycine (C3) | hexanoylcarnitine (C6) | myo-inositol |
| pseudouridine | valylisoleucine | alpha-ketobutyrate |
| ADSGEGDFXAEGGGVR* | beta-alanine | S-adenosylhomocysteine (SAH) |
| 2-hydroxyhippurate (salicylurate) | 1-linoleoyl-GPE (18:2)* | 1-oleoylglycerol (18:1) |
| alpha-glutamyltyrosine | gamma-glutamylglutamate | tartronate (hydroxymalonate) |
| fucose | 3-hydroxy-2-ethylpropionate | 3-methylglutarylcarnitine-2 |
| glucuronate | adenine | 1-methylurate |
| 3-methylglutarylcarnitine-1 | xylitol | N-acetyl-beta-alanine |
| xanthine | N2 N2-dimethylguanosine | histidyltryptophan |
| 12-HETE | methyl indole-3-acetate | 1-oleoyl-GPC (18:1)* |
| glucose | homostachydrine* | 3-hydroxydecanoate |
| salicylate | phenylacetylglutamine | — |

Figure 35:
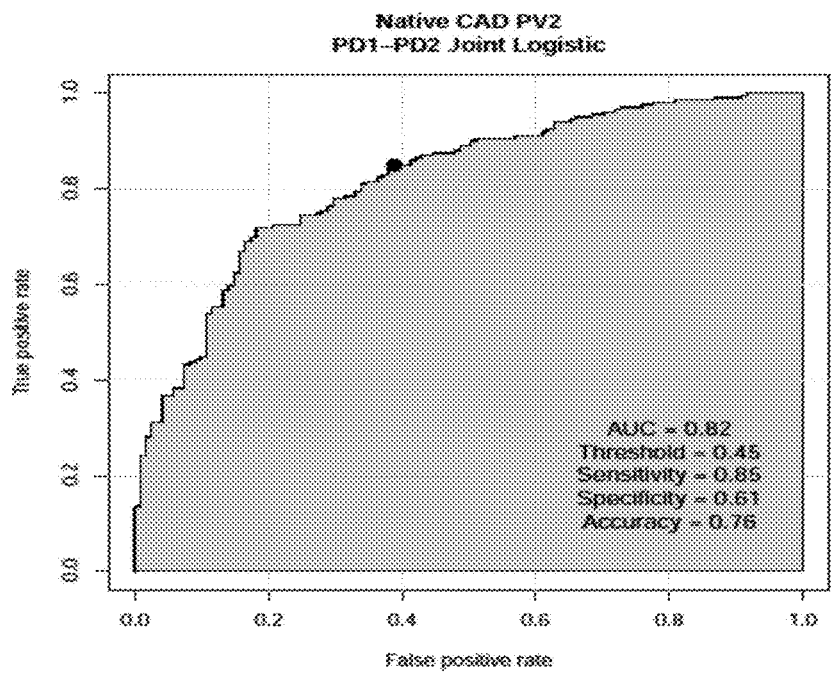
FIG. 35 is a graph demonstrating a ROC curve for the Metabolomic Model of $A_{FNF}^{nCAD}$ (AUC=0.82; Threshold=0.45; Sensitivity=0.85; Specificity=0.61; Accuracy=0.76).

Of the 83 metabolomic variables exhibiting a nominal univariate association for $A_{FNF}^{nCAD}$, a panel of eight metabolomic variables were selected as best predictors; these were combined with age and gender in a prediction model for CAD. Table 30 provides the relative influence of the eight metabolomic variables, in combination with age and gender, for the Metabolomics Model of $A_{FNF}^{nCAD}$. FIG. 35 provides a ROC curve for the Metabolomics Model of $A_{FNF}^{nCAD}$. Table 53 provides the sensitivity, specificity, positive predictive value (PPV) and negative predictive value (NPV) for the range of predicted probability thresholds; Area Under the Curve (AUC) and accuracy was estimated.

TABLE 30

| Variable | Relative Influence | Direction of Change |
|---|---|---|
| valylleucine | 28.88 | Decreased |
| glutamate | 14.47 | Elevated |
| acisoga | 14.25 | Elevated |
| urate | 10.39 | Elevated |
| glucuronate | 9.26 | Elevated |
| age | 6.68 | Elevated |
| fucose | 6.18 | Elevated |
| Butyrylcarnitine (C4) | 4.72 | Elevated |
| mannose | 4.46 | Elevated |
| Male gender | 0.70 | Present§ |

§The term "present" conveys that male gender was taken into account in the prediction model, with 'relative influence' denoting the association of male gender with the outcome (i.e., ASCAD or the presents of a coronary atherosclerotic plaque).

b. Independently Significant in Fasting and Non-Fasting—$A_{IFNF}^{nCAD}$
   i. Of the 481 analytes measured, 4 metabolomic variables exhibited a nominal univariate association (raw p<0.05) for $A_{IFNF}^{nCAD}$. Table 31 provides a list of the 4 metabolomic variables for $A_{IFNF}^{nCAD}$.

TABLE 31

| | | |
|---|---|---|
| acisoga | o.cresol.sulfate | Cysteine.glutathione.disulfide |
| threonate | — | — |

Figure 36:
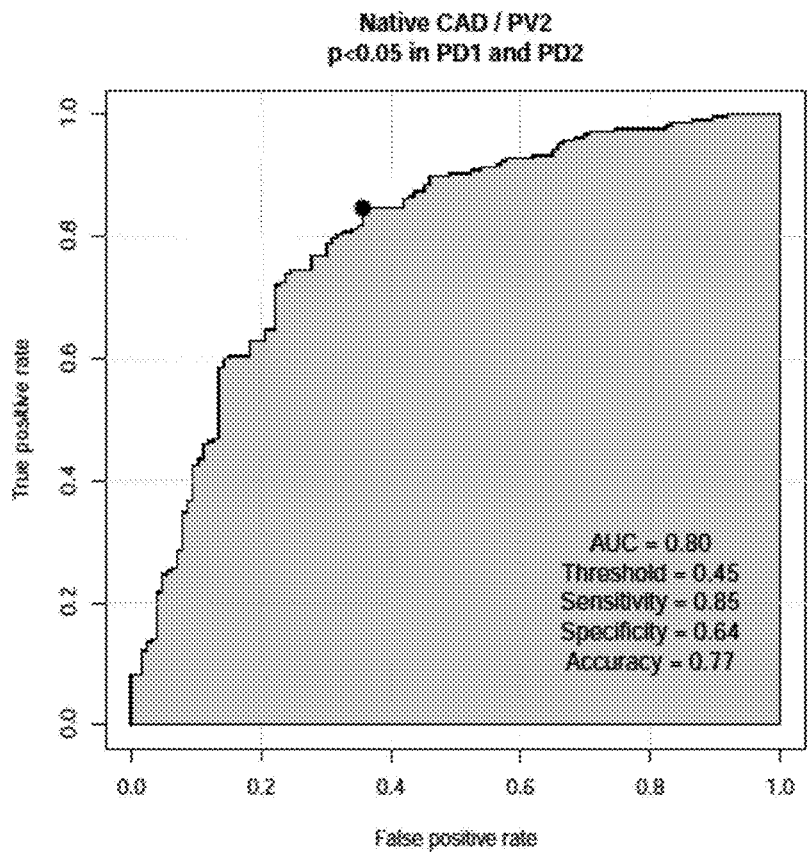
FIG. 36 is a graph demonstrating a ROC curve for the Metabolomic Model of $A_{IFNF}^{nCAD}$ (AUC=0.80; Threshold=0.45; Sensitivity=0.85; Specificity=0.64; Accuracy=0.77).

Of the 4 metabolomic variables exhibiting a nominal univariate association for $A_{IFNF}^{nCAD}$; a panel of all four metabolomic variables were selected as best predictors; these were combined with age and gender in a prediction model for CAD. Table 32 provides the relative influence of the four metabolomic variables, in combination with age and gender, for the Metabolomics Model of $A_{IFNF}^{nCAD}$. FIG. 36 provides a ROC curve for the Metabolomics Model of $A_{IFNF}^{nCAD}$. Table 53 provides the sensitivity, specificity, positive predictive value (PPV) and negative predictive value (NPV) for the range of predicted probability thresholds; Area Under the Curve (AUC) and accuracy was estimated.

TABLE 32

| Variable | Relative Influence | Direction of Change |
|---|---|---|
| acisoga | 40.74 | Elevated |
| age | 20.77 | Elevated |
| cysteine.glutathione.disulfide | 18.87 | Decreased |
| threonate | 12.67 | Decreased |
| o-cresol.sulfate | 4.49 | Elevated |
| Male gender | 2.45 | Present | c. Significant in Fasting—$A_F^{nCAD}$
   i. Of the 481 analytes measured, 34 metabolomic variables exhibited a nominal univariate association (raw p<0.05) for $A_F^{nCAD}$. Table 33 provides a list of the 34 metabolomic variables for $A_F^{nCAD}$.

TABLE 33

| | | |
|---|---|---|
| xylitol | valylleucine | cysteine-glutathione disulfide |
| 3-carboxy-4-methyl-5-propyl-2-furanpropanoate (CMPF) | N-acetylleucine | threonate |
| serylleucine | alpha-glutamyltyrosine | fucose |
| phenylalanylvaline | 4-androsten-3alpha 17alpha-diol monosulfate 2 | adenosine |
| 12-HETE | inositol 1-phosphate (I1P) | valylisoleucine |
| glycocholenate sulfate* | 1-docosahexaenoyl-GPC* (22:6)* | phenylalanylserine |
| oleic ethanolamide | 2-hydroxyhippurate (salicylurate) | gamma-tocopherol |

TABLE 33-continued

| | | |
|---|---|---|
| acisoga | salicylate | palmitoyl ethanolamide |
| leucylglycine | phenylalanylglycine | hydroquinone sulfate |
| N-acetylphenylalanine | glycylphenylalanine | propionylglycine (C3) |
| o-cresol sulfate | 3-methoxytyrosine | — |
| histidyltryptophan | adenine | — |

Figure 37:
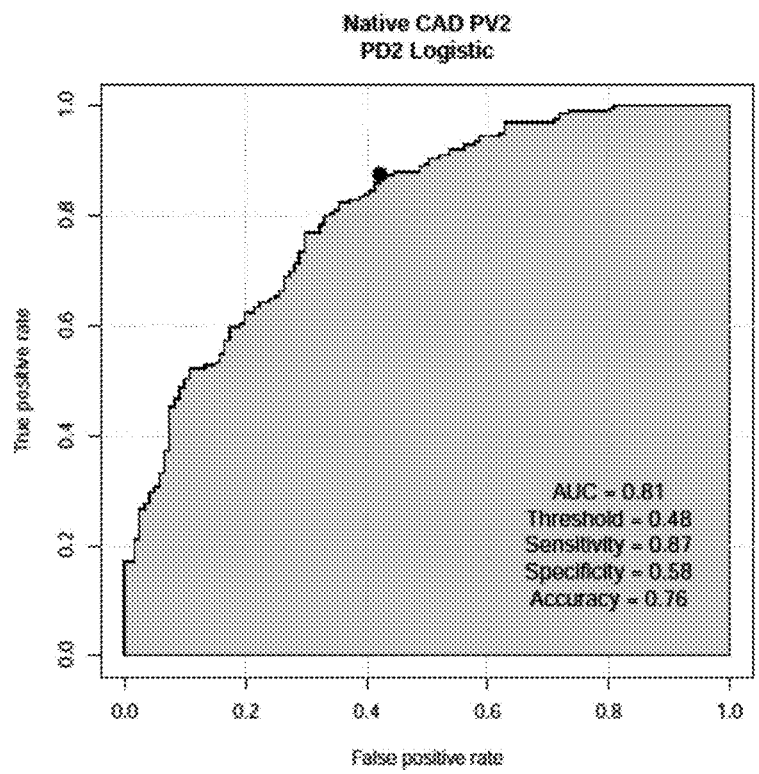
FIG. 37 is a graph demonstrating a ROC curve for the Metabolomic Model of $A_{F}^{nCAD}$ (AUC=0.81; Threshold=0.48; Sensitivity=0.87; Specificity=0.58; Accuracy=0.76).
Figure 38:
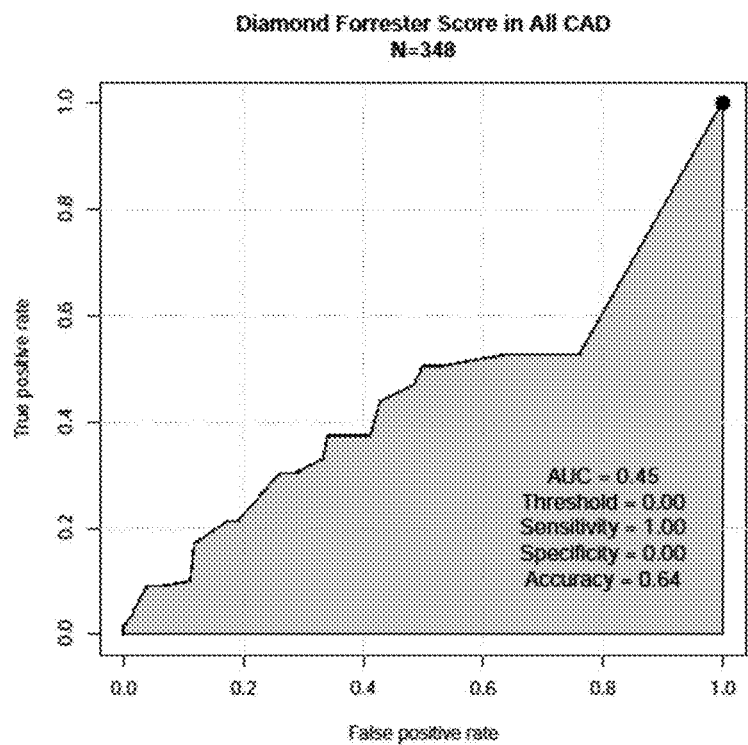
FIG. 38 is a graph demonstrating a ROC curve for Diamond Forrester Score and $A^{aCAD}$ (AUC=0.45; Threshold=0.00; Sensitivity=1.00; Specificity=0.00; Accuracy=0.64).

Of the 34 metabolomic variables exhibiting a nominal univariate association for $A_F^{nCAD}$, a panel of eight metabolomic variables were selected as best predictors; these were combined with age and gender in a prediction model for CAD. Table 34 provides the relative influence of the eight metabolomic variables, in combination with age and gender, for the Metabolomics Model of $A_F^{nCAD}$. FIG. 37 provides a ROC curve for the Metabolomics Model of $A_F^{nCAD}$. Table 53 provides the sensitivity, specificity, positive predictive value (PPV) and negative predictive value (NPV) for the range of predicted probability thresholds; Area Under the Curve (AUC) and accuracy was estimated.

TABLE 34

| Variable | Relative Influence | Direction of Change |
|---|---|---|
| N-acetylphenylalanine | 22.27 | Elevated |
| age | 18.18 | Elevated |
| valylleucine | 17.61 | Decreased |
| xylitol | 8.07 | Elevated |
| 2-hydroxyhippurate (salicylurate) | 6.97 | Elevated |
| N-acetylleucine | 6.15 | Elevated |
| serylleucine | 6.15 | Decreased |
| fucose | 6.06 | Elevated |
| glycylphenylalanine | 4.97 | Decreased |
| Male gender | 3.56 | Present |

II. Atherosclerosis in All CAD (inc revasc)—$A^{aCAD}$ a. Significant in Fasting & Non-Fasting Combined—$A_{FNF}^{aCAD}$ i. Of the 481 analytes measured, 92 metabolomic variables exhibited a nominal univariate association (raw p<0.05) for $A_{FNF}^{aCAD}$. Table 41 provides a filtered list of the 92 metabolomic variables for $A_{FNF}^{aCAD}$.

TABLE 41

| | | |
|---|---|---|
| acisoga | tyrosylglutamine | N6-carbamoylthreonyladenosine |
| Glutamate | xanthine | 2-linoleoyl-GPC* (18:2)* |
| Threonate | beta-alanine | 3-methyl-2-oxobutyrate |
| Mannose | isobutyrylglycine (C4) | methyl glucopyranoside (alpha + beta) |
| Urate | 3-methylglutarylcarnitine-1 | serylleucine |
| cysteine-glutathione disulfide | valerylcarnitine (C5) | caproate (6:0) |
| oleic ethanolamide | 1-linoleoyl-GPC (18:2) | N-methyl proline |
| pyroglutamylglutamine | hexanoylcarnitine (C6) | laurylcarnitine (C12)* |
| butyrylcarnitine (C4) | 2-hydroxybutyrate (AHB) | o-cresol sulfate |
| Cytidine | 1-arachidoyl-GPC (20:0) | gamma-glutamylglutamate |
| hydroxybutyrylcarnitine* | guanidinosuccinate | N-acetyl-beta-alanine |
| alpha-glutamyltyrosine | fucose | 1-eicosenoylglycerophosphocholine (20:1n9)* |
| 2-hydroxyhippurate (salicylurate) | phenylacetylglutamine | N-acetylglycine |
| Valylleucine | 3-methylglutarylcarnitine-2 | seryltyrosine |
| propionylglycine (C3) | glycohyocholate | 4-guanidinobutanoate |
| 1-nonadecanoylglycerophosphocholine (19:0) | N6-methyladenosine | S-methylcysteine |
| Glycine | N2 N2-dimethylguanosine | isoleucylvaline |
| 12-HETE | gamma-glutamylvaline | adenine |
| pseudouridine | leucylaspartate | 1-methylurate |
| Salicylate | 2-hydroxyoctanoate | xylitol |
| Glucose | alpha-ketobutyrate | phenylalanylalanine |
| ADSGEGDFXAEGGGVR* | glycocholenate sulfate* | O-sulfo-L-tyrosine |
| 1-linoleoyl-GPE (18:2)* | valylisoleucine | erucamide |
| Phenylalanylvaline | homostachydrine* | pregnanediol-3-glucuronide |
| Tigloylglycine | methyl indole-3-acetate | 3-hydroxy-2-ethylpropionate |
| Glucuronate | leucylglycine | pyridoxal |
| palmitoyl ethanolamide | N-acetylthreonine | 1-oleoyl-GPC (18:1)* |
| 1-oleoylglycerol (18:1) | 2-hydroxydecanoate | 2prime-deoxyuridine |
| 12 13-DiHOME | 1-methylguanosine | threonylphenylalanine |
| 3-methoxytyrosine | prolylhydroxyproline | 2-aminoadipate |
| 2-linoleoyl-GPE* (18:2)* | prolylglycine | — |

Figure 39:
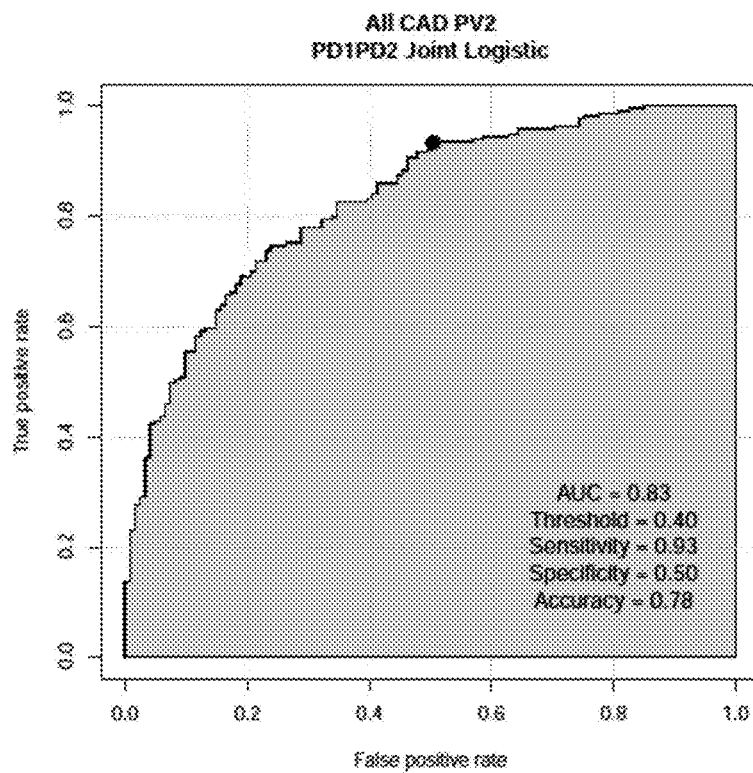
FIG. 39 is a graph demonstrating a ROC curve for the Metabolomic Model of $A_{FNF}^{aCAD}$ (AUC=0.83; Threshold=0.40; Sensitivity=0.93; Specificity=0.50; Accuracy=0.78).

Of the 92 metabolomic variables exhibiting a nominal univariate association for $A_{FNF}^{aCAD}$, a panel of eight metabolomic variables were selected as best predictors; these were combined with age and gender in a prediction model for CAD. Table 36 provides the relative influence of the eight metabolomic variables combined with age and gender for the Metabolomics Model of $A_{FNF}^{aCAD}$. FIG. 39 provides a ROC curve for the Metabolomics Model of $A_{FNF}^{aCAD}$. Table 54 provides the sensitivity, specificity, positive predictive value (PPV) and negative predictive value (NPV) for the range of predicted probability thresholds; Area Under the Curve (AUC) and accuracy was estimated.

TABLE 36

| Variable | Relative Influence | Direction of Change |
|---|---|---|
| valylleucine | 26.79 | Decreased |
| acisoga | 16.87 | Elevated |
| glutamate | 13.93 | Elevated |
| urate | 9.74 | Elevated |
| glucuronate | 8.74 | Elevated |
| mannose | 7.13 | Elevated |
| age | 6.24 | Elevated |
| 12-HETE | 5.03 | Decreased |
| Valerylcarnitine (C5) | 4.81 | Elevated |
| Male gender | 0.72 | Present | b. Independently Significant in Fasting and Non-Fasting—$A_{IFNF}^{aCAD}$ i. Of the 481 analytes measured, 6 metabolomic variables exhibited a nominal univariate association (raw p<0.05) for $A_{IFNF}^{aCAD}$. Table 37 provides a list of the 6 metabolomic variables for $A_{IFNF}^{aCAD}$.

TABLE 37

| threonate | threonate | cysteine-glutathione disulfide |
|---|---|---|
| o-cresol sulfate | 1-nonadecanoylglycerophosphocholine (19:0) | glucose |

Figure 40:
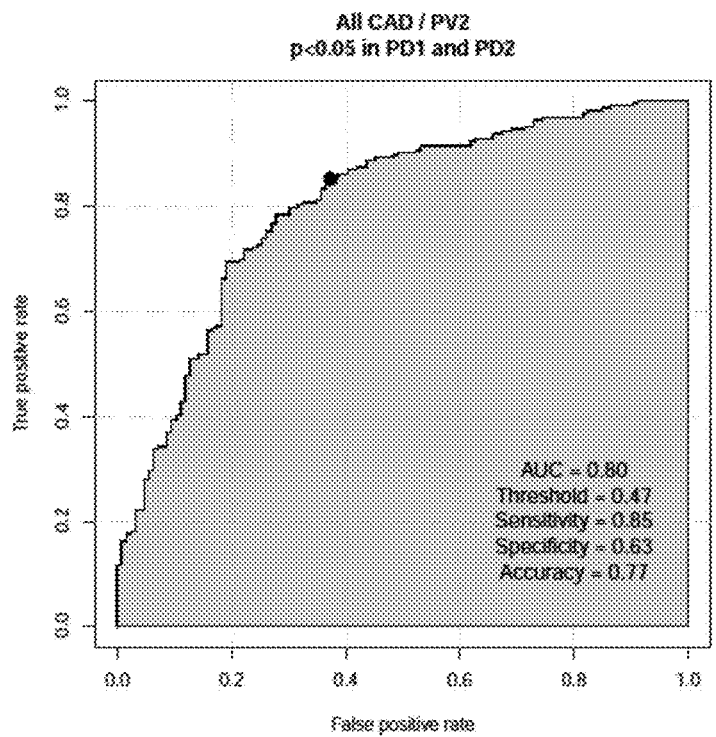
FIG. 40 is a graph demonstrating a ROC curve for the Metabolomic Model of $A_{IFNF}^{aCAD}$ (AUC=0.80; Threshold=0.47; Sensitivity=0.85; Specificity=0.63; Accuracy=0.77).

Of the 6 metabolomic variables exhibiting a nominal univariate association for $A_{IFNF}^{aCAD}$, a panel of all six metabolomic variables were selected as best predictors; these were combined with age and gender in a prediction model for CAD. Table 38 provides the relative influence of the six metabolomic variables, in combination with age and gender, for the Metabolomics Model of $A_{IFNF}^{aCAD}$. FIG. 40 provides a ROC curve for the Metabolomics Model of $A_{IFNF}^{aCAD}$. Table 54 provides the sensitivity, specificity, positive predictive value (PPV) and negative predictive value (NPV) for the range of predicted probability thresholds; Area Under the Curve (AUC) and accuracy was estimated.

TABLE 38

| Variable | Relative Influence | Direction of Change |
|---|---|---|
| acisoga | 39.32 | Elevated |
| age | 17.31 | Elevated |
| 1.nonadecanoylglycerophosphocholine (19:0) | 12.00 | Decreased |
| cysteine-glutathione disulfide | 10.91 | Decreased |
| threonate | 10.71 | Decreased |
| glucose | 6.64 | Elevated |
| Male gender | 2.06 | Present |
| o-cresol sulfate | 1.05 | Elevated | c. Significant in Fasting —$A_F^{aCAD}$ i. Of the 481 analytes measured, 48 metabolomic variables exhibited a nominal univariate association (raw p<0.05) for $A_F^{aCAD}$. Table 39 provides a list of the 48 metabolomic variables for $A_F^{aCAD}$.

TABLE 39

| | | |
|---|---|---|
| 12-HETE | N-acetylphenylalanine | 1-arachidonylglycerol |
| alpha-glutamyltyrosine | N-acetylleucine | Pyroglutamylvaline |
| salicylate | 4-androsten-3alpha 17alpha-diol monosulfate 2 | phenylalanyltryptophan |
| 2-hydroxyhippurate (salicylurate) | o-cresol sulfate | methyl indole-3-acetate |
| acisoga | phenylalanylvaline | Histidyltryptophan |
| 3-carboxy-4-methyl-5-propyl-2-furanpropanoate (CMPF) | leucylglycine | 4-ethylphenyl sulfate |
| threonate | phenylalanylglycine | 1-myristoylglycerol (14:0) |
| glycocholenate sulfate* | propionylglycine (C3) | inositol 1-phosphate (I1P) |
| xylitol | mannitol | 1-nonadecanoylglycerophosphocholine (19:0) |
| 1-docosahexaenoyl-GPC* (22:6)* | serylleucine | Glucose |
| phenylalanylserine | hydroquinone sulfate | N-stearoyltaurine |
| 3-methoxytyrosine | adenosine | Valylisoleucine |
| oleic ethanolamide | 2-hydroxydecanoate | beta-alanine |
| cysteine-glutathione disulfide | tyrosylglutamine | N-acetylglycine |
| glycylphenylalanine | N-octanoylglycine | Allantoin |
| valylleucine | adenine | Phenylalanylphenylalanine |

Figure 41:
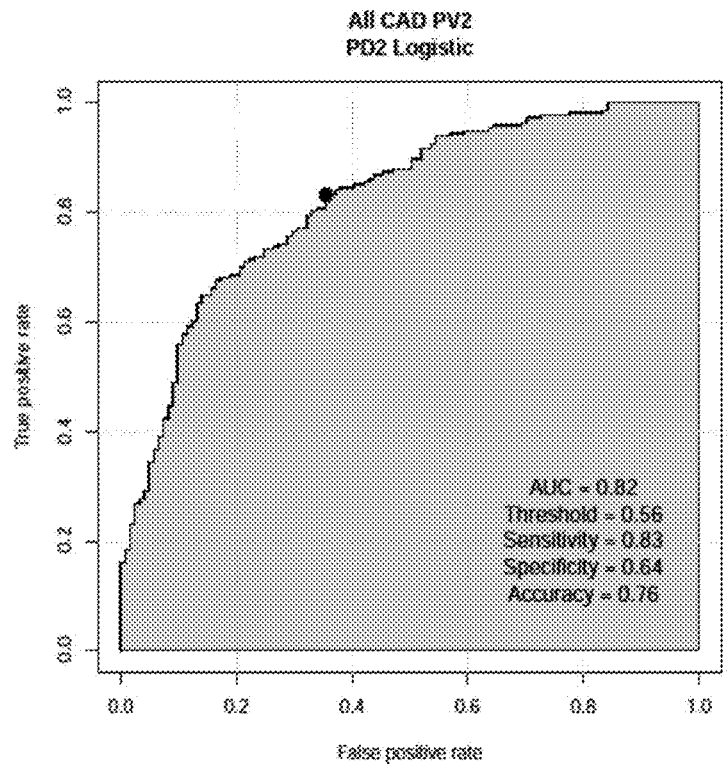
FIG. 41 is a graph demonstrating a ROC curve for the Metabolomic Model of $A_{F}^{aCAD}$ (AUC=0.82; Threshold=0.56; Sensitivity=0.83; Specificity=0.64; Accuracy=0.76).
Figure 42:
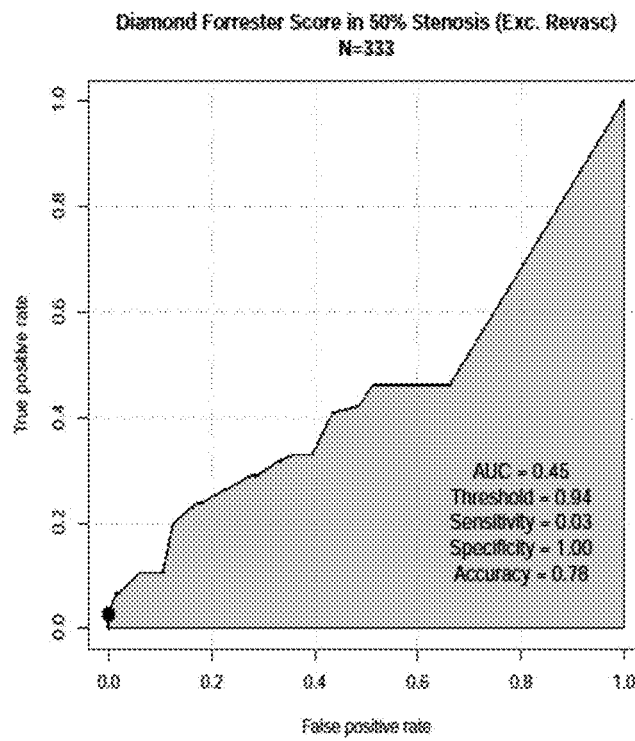
FIG. 42 is a graph demonstrating a ROC curve for Diamond Forrester Score and $S^{nCAD}$ (AUC=0.45; Threshold=0.94; Sensitivity=0.03; Specificity=1.00; Accuracy=0.78).

Of the 48 metabolomic variables exhibiting a nominal univariate association for $A_F^{aCAD}$, a panel of seven metabolomic variables were selected as best predictors; these were combined with age and gender in a prediction model for CAD. Table 40 provides the relative influence of the seven metabolomic variables, in combination with age and gender, for the Metabolomics Model of $A_F^{aCAD}$. FIG. 41 provides a ROC curve for the Metabolomics Model of $A_F^{aCAD}$. Table 54 provides the sensitivity, specificity, positive predictive value (PPV) and negative predictive value (NPV) for the range of predicted probability thresholds; Area Under the Curve (AUC) and accuracy was estimated.

TABLE 40

| Variable | Relative Influence | Direction of Change |
| --- | --- | --- |
| age | 21.21 | Elevated |
| valylleucine | 20.76 | Decreased |
| N-acetylphenylalanine | 18.59 | Elevated |
| 2-hydroxyhippurate (salicylurate) | 12.20 | Elevated |
| N-acetylleucine | 6.10 | Elevated |
| 12-HETE | 5.96 | Decreased |
| xylitol | 5.40 | Elevated |
| glycylphenylalanine | 5.39 | Decreased |
| Male gender | 4.40 | Present |

III. 50% stenosis in Native CAD—$S^{nCAD}$ a. Significant in Fasting & Non-Fasting Combined—$S_{FNF}^{nCAD}$ i. Of the 481 analytes measured, 49 metabolomic variables exhibited a nominal univariate association (raw p<0.05) for $S_{FNF}^{nCAD}$. Table 41 provides a list of the 49 metabolomic variables for $S_{FNF}^{nCAD}$.

TABLE 41

| | | |
| --- | --- | --- |
| threonate | serotonin (5HT) | 5alpha-androstan-3alpha 17beta-diol disulfate |
| N-acetylglycine | xanthine | 1-stearoyl-GPC (18:0) |
| glycerate | 2-oleoyl-GPE* (18:1)* | serine |
| isobutyrylglycine (C4) | 4-guanidinobutanoate | acisoga |
| valerylcarnitine (C5) | leucylleucine | mannose |
| fumarate | cholate | valylleucine |
| 1-nonadecanoylglycerophosphocholine (19:0) | propionylglycine (C3) | gamma-tocopherol |
| tartronate (hydroxymalonate) | glycocholate | 3-ethylphenylsulfate |
| 2-hydroxyhippurate (salicylurate) | N-octanoylglycine | glutamate |
| 1-arachidoyl-GPC (20:0) | glycoursodeoxycholate | sphingosine 1-phosphate |
| threitol | isovalerylglycine | carnitine |
| N-(2-furoyl)glycine | pregnanediol-3-glucuronide | arabonate |
| tigloylglycine | 5alpha-androstan-3beta 17beta-diol monosulfate 2 | cyclo(leu-pro) |
| salicylate | arabinose | indoleacetylglutamine |
| N-acetylthreonine | 1-linoleoyl-GPE (18:2)* | prolylglycine |
| xylonate | 5-HETE | — |
| xylose | hydroquinone sulfate | — |

Figure 43:
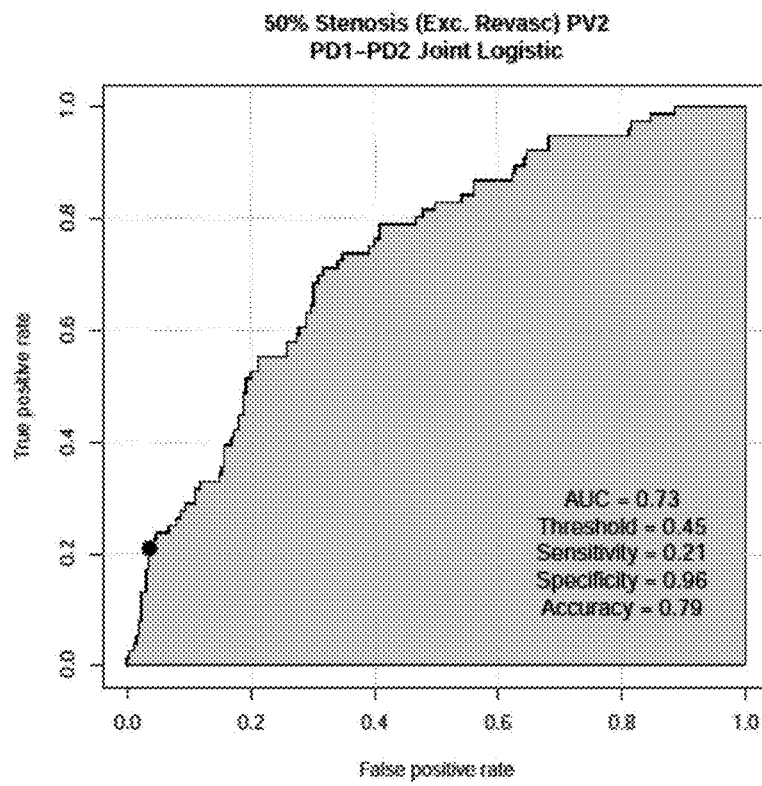
FIG. 43 is a graph demonstrating a ROC curve for the Metabolomic Model of $S_{FNF}^{nCAD}$ (AUC=0.73; Threshold=0.45; Sensitivity=0.21; Specificity=0.96; Accuracy=0.79).

Of the 49 metabolomic variables exhibiting a nominal univariate association for $S_{FNF}^{nCAD}$, a panel of eight metabolomic variables were selected as best predictors; these were combined with age and gender in a prediction model for CAD. Table 42 provides the relative influence of the eight metabolomic variables, in combination with age and gender, for the Metabolomics Model of $S_{FNF}^{nCAD}$. FIG. 43 provides a ROC curve for the Metabolomics Model of $S_{FNF}^{nCAD}$. Table 55 provides the sensitivity, specificity, positive predictive value (PPV) and negative predictive value (NPV) for the range of predicted probability thresholds; Area Under the Curve (AUC) and accuracy was estimated.

TABLE 42

| Variable | Relative Influence | Direction of Change |
| --- | --- | --- |
| Age | 37.04 | Elevated |
| valerylcarnitine (C5) | 14.32 | Elevated |
| N-acetylthreonine | 10.39 | Elevated |
| tigloylglycine | 8.72 | Decreased |
| 2-hydroxyhippurate (salicylurate) | 7.06 | Elevated |
| glycerate | 6.42 | Decreased |
| salicylate | 5.67 | Decreased |
| threonate | 5.58 | Decreased |
| tartronate (hydroxymalonated); | 4.25 | Elevated |
| Male gender | 0.55 | Present | b. Independently Significant in Fasting and Non-Fasting —$S_{IFNF}^{nCAD}$ i. Of the 481 analytes measured, 2 metabolomic variables exhibited a nominal univariate association (raw p<0.05) for $S_{IFNF}^{nCAD}$. Table 43 provides a list of the 2 metabolomic variables for $S_{IFNF}^{nCAD}$.

TABLE 43

| | | |
| --- | --- | --- |
| N-acetylglycine | 3-ethylphenylsulfate | — |

Figure 44:
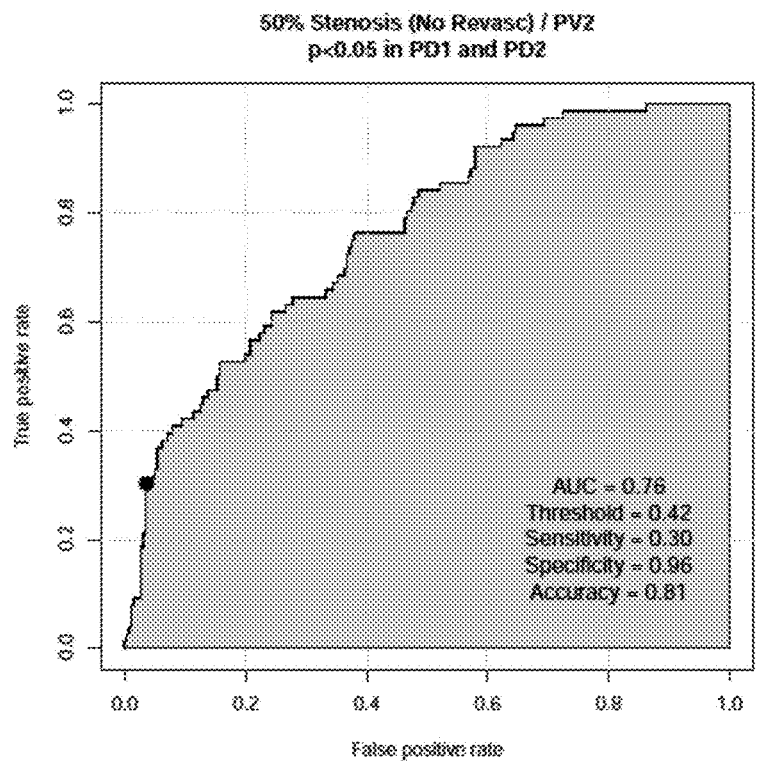
FIG. 44 is a graph demonstrating a ROC curve for the Metabolomic Model of $S_{IFNF}^{nCAD}$ (AUC=0.76; Threshold=0.42; Sensitivity=0.30; Specificity=0.96; Accuracy=0.81).

Of the 2 metabolomic variables exhibiting a nominal univariate association for $S_{IFNF}^{nCAD}$, a panel of both variables were selected as best predictors; these were combined with age and gender in a prediction model for CAD. Table 44 provides the relative influence of the two metabolomic variables in combination with age and gender for the Metabolomics Model of $S_{IFNF}^{nCAD}$. FIG. 44 provides a ROC curve for the Metabolomics Model of $S_{IFNF}^{nCAD}$. Table 55 provides the sensitivity, specificity, positive predictive value (PPV) and negative predictive value (NPV) for the range of predicted probability thresholds; Area Under the Curve (AUC) and accuracy was estimated.

TABLE 44

| Variable | Relative Influence | Direction of Change |
|---|---|---|
| age | 67.33 | Elevated |
| N-acetylglycine | 14.67 | Decreased |
| 3-ethylphenylsulfate | 12.88 | Elevated |
| Male gender | 5.12 | Elevated | c. Significant in Fasting—$S_F^{nCAD}$
 i. Of the 481 analytes measured, 28 metabolomic variables exhibited a nominal univariate association (raw p<0.05) for $S_F^{nCAD}$. Table 45 provides a filtered list of the 28 metabolomic variables for $S_F^{nCAD}$.

TABLE 45

| | | |
|---|---|---|
| leucylleucine | valylisoleucine | 7-methylguanine |
| asparagine | glycocholenate sulfate* | cyclo(leu-pro) |
| glycerate | arabitol | Methionine |
| threitol | N-acetylglycine | propionylglycine (C3) |
| cholate | serotonin (5HT) | Serine |
| N-octanoylglycine | xylose | 2-oleoyl-GPE* (18:1)* |
| xylonate | N-acetylputrescine | Tigloylglycine |
| isobutyrylglycine (C4) | arabonate | 3-ethylphenylsulfate |
| isovalerylglycine | lysine | — |
| fumarate | N-(2-furoyl)glycine | — |

Figure 45:
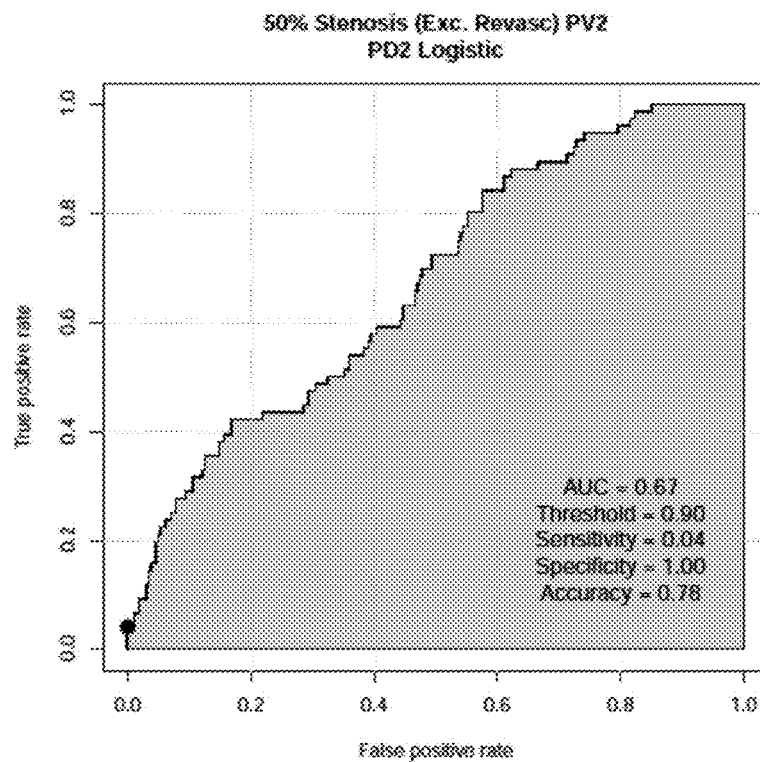
FIG. 45 is a graph demonstrating a ROC curve for the Metabolomic Model of $S_{F}^{nCAD}$ (AUC=0.67; Threshold=0.90; Sensitivity=0.04; Specificity=1.0; Accuracy=0.78).
Figure 46:
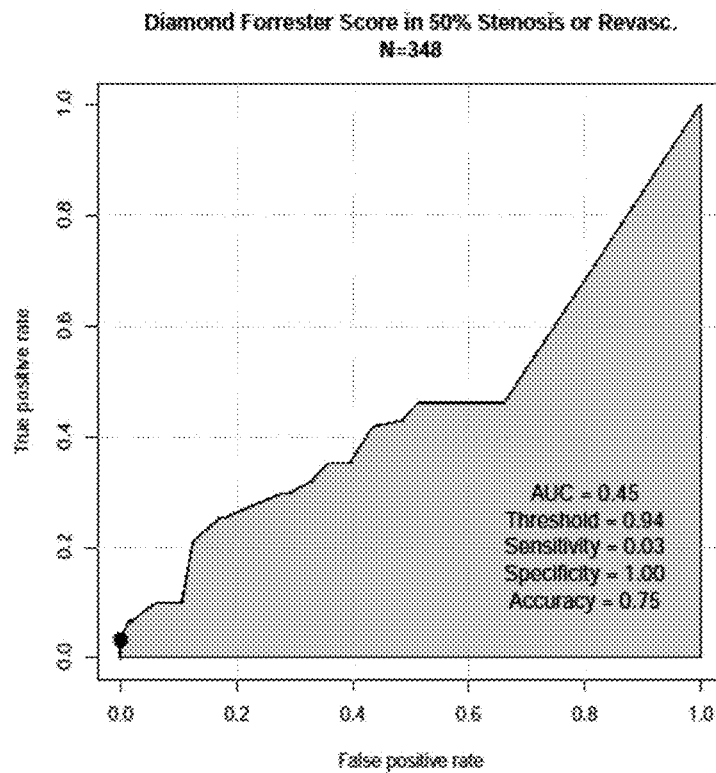
FIG. 46 is a graph demonstrating a ROC curve for Diamond Forrester Score and $s^{aCAD}$ (AUC=0.45; Threshold=0.94; Sensitivity=0.03; Specificity=1.00; Accuracy=0.75).

Of the 28 metabolomic variables exhibiting a nominal univariate association for $S_F^{nCAD}$, a panel of eight metabolomic variables were selected as best predictors; they were combined with age and gender in a prediction model for CAD. Table 46 provides the relative influence of the eight metabolomic variables, in combination with age and gender, for the Metabolomics Model of $S_F^{nCAD}$. FIG. 45 provides a ROC curve for the Metabolomics Model of $S_F^{nCAD}$. Table 55 provides the sensitivity, specificity, positive predictive value (PPV) and negative predictive value (NPV) for the range of predicted probability thresholds; Area Under the Curve (AUC) and accuracy was estimated.

TABLE 46

| Variable | Relative Influence | Direction of Change |
|---|---|---|
| age | 24.44 | Elevated |
| leucylleucine | 21.83 | Decreased |
| serotonin (5HT) | 11.37 | Elevated |
| N-acetylputrescine | 9.68 | Decreased |
| glycocholenate sulfate | 8.56 | Decreased |
| propionylglycine (C3) | 6.95 | Decreased |
| cholate | 6.14 | Decreased |
| asparagine | 5.73 | Elevated |
| 3-ethylphenylsulfate | 4.79 | Elevated |
| Male gender | 0.50 | Present |

IV. 50% stenosis in ALL CAD (inc revasc)—$S^{aCAD}$
 a. Significant in Fasting & Non-Fasting Combined—$S_{FNF}^{aCAD}$
  i. Of the 481 analytes measured, 72 metabolomic variables exhibited a nominal univariate association (raw p<0.05) for $S_{FNF}^{aCAD}$. Table 47 provides a list of the 72 metabolomic variables for $S_{FNF}^{aCAD}$.

TABLE 47

| | | |
|---|---|---|
| threonate | prolylglycine | 2-hydroxydecanoate |
| 1-linoleoyl-GPE (18:2)* | N-octanoylglycine | glutamate |
| N-acetylglycine | threitol | N-acetylthreonine |
| glycoursodeoxycholate | fumarate | taurine |
| 2-hydroxyhippurate (salicylurate) | pregnanediol-3-glucuronide | 1-oleoylplasmenylethanolamine* |
| salicylate | 1-oleoyl-GPI (18:1)* | 1-palmitoyl-GPE (16:0) |
| 2-linoleoyl-GPE* (18:2)* | serotonin (5HT) | N-acetylglutamate |
| mannose | xylonate | 13-HODE + 9-HODE |
| tigloylglycine | cyclo(leu-pro) | 1-palmitoyl-GPI* (16:0)* |
| 2-linolenoylglycerophosphocholine (18:3n3)* | glycerate | hydroquinone sulfate |
| 1-nonadecanoylglycerophosphocholine (19:0) | tartronate (hydroxymalonate) | caprylate (8:0) |
| 2-oleoyl-GPE* (18:1)* | xylose | 1-stearoyl-GPC (18:0) |
| isovalerylglycine | glycohyocholate | glycochenodeoxycholate |
| isobutyrylglycine (C4) | glucose | p-cresol sulfate |
| N-(2-furoyl)glycine | xanthine | 12-HETE |
| glycocholate | cyclo(L-phe-L-pro) | 5-hydroxyindoleacetate |
| acisoga | beta-alanine | arabonate |
| 4-guanidinobutanoate | pyridoxate | 2-hydroxyoctanoate |
| 1-arachidoyl-GPC (20:0) | tartarate | urate |
| propionylglycine (C3) | 1-linoleoyl-GPC (18:2) | valylleucine |
| valerylcarnitine (C5) | pyridoxal | carnitine |
| 1-oleoylglycerol (18:1) | cholate | 1-linoleoyl-GPI* (18:2)* |
| 1-oleoyl-GPE (18:1) | serine | N-acetylputrescine |
| arabinose | homostachydrine* | succinate |

Figure 47:
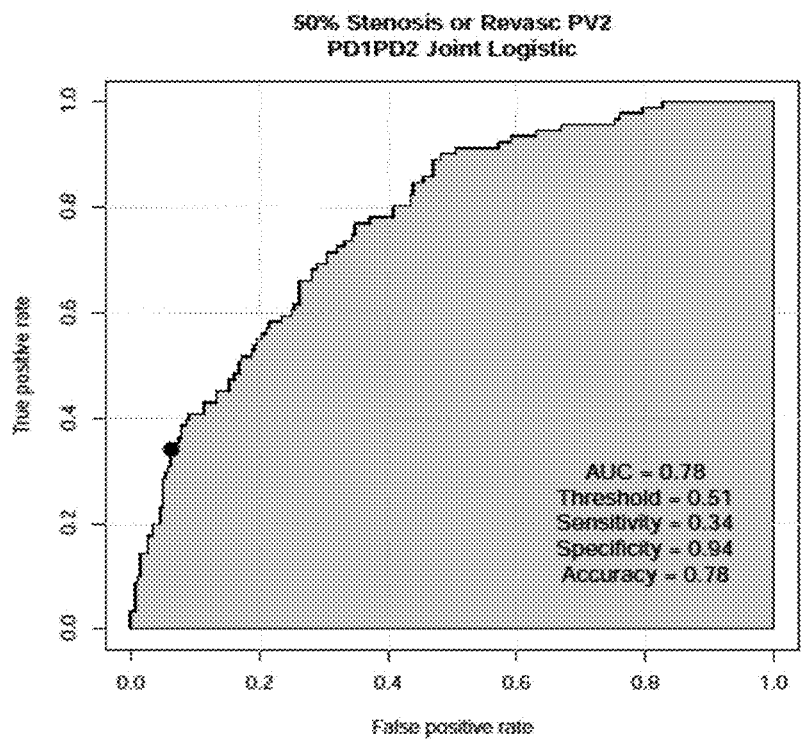
FIG. 47 is a graph demonstrating a ROC curve for the Metabolomic Model of $S_{FNF}^{aCAD}$ (AUC=0.78; Threshold=0.51; Sensitivity=0.34; Specificity=0.94; Accuracy=0.78).

Of the 72 metabolomic variables exhibiting a nominal univariate association for $S_{FNF}^{aCAD}$, a panel of eight metabolomic variables were selected as best predictors; these were combined with age and gender in a prediction model for CAD. Table 48 provides the relative influence of the eight metabolomic variables in combination with age and gender for the Metabolomics Model of $S_{FNF}^{aCAD}$. FIG. 47 provides a ROC curve for the Metabolomics Model of $S_{FNF}^{aCAD}$. Table 56 provides the sensitivity, specificity, positive predictive value (PPV) and negative predictive value (NPV) for the range of predicted probability thresholds; Area Under the Curve (AUC) and accuracy was estimated.

TABLE 48

| Variable | Relative Influence | Direction of Change |
| --- | --- | --- |
| Age | 18.38 | Elevated |
| glycoursodeoxycholate | 16.52 | Decreased |
| acisoga | 12.81 | Elevated |
| 2-hydroxyhippurate (salicylurate) | 10.33 | Elevated |
| 1-linoleoyl.GPE (18:2) | 10.26 | Decreased |
| valerylcarnitine (C5), | 8.91 | Elevated |
| threonate | 7.13 | Decreased |
| mannose | 7.12 | Elevated |
| salicylate | 7.02 | Elevated |
| Male gender | 1.52 | Present | b. Independently Significant in Fasting and Non-Fasting—$S_{IFNF}^{aCAD}$ i. Of the 481 analytes measured, 5 metabolomic variables exhibited a nominal univariate association (raw p<0.05) for $S_{IFNF}^{aCAD}$. Table 49 provides a filtered list of the 5 metabolomic variables for $S_{IFNF}^{aCAD}$.

TABLE 49

| | | |
| --- | --- | --- |
| N-acetylglycine | threonate | Salicylate |
| 2-hydroxyhippurate (salicylurate) | 3-ethylphenylsulfate | — |

Figure 48:
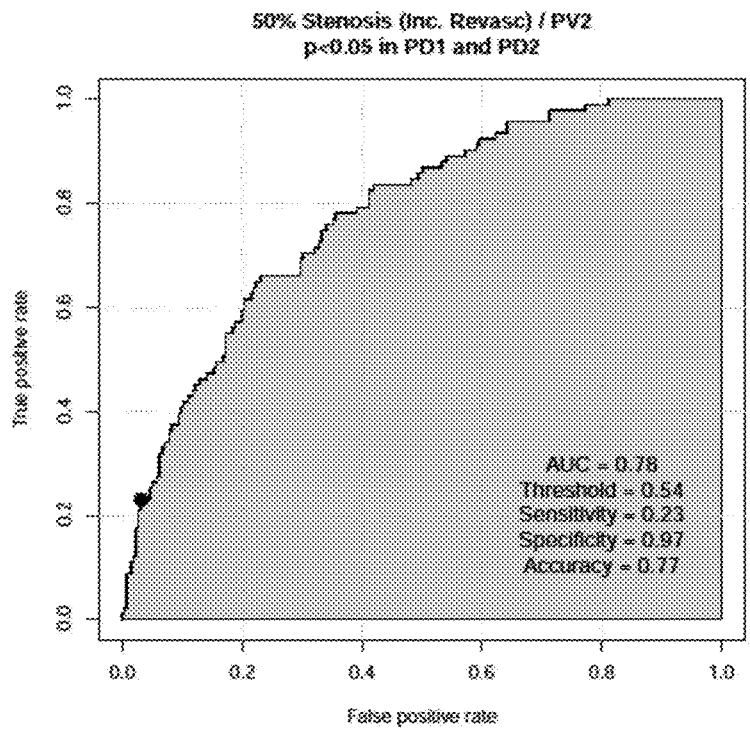
FIG. 48 is a graph demonstrating a ROC curve for the Metabolomic Model of $S_{IFNF}^{aCAD}$ (AUC=0.78; Threshold=0.54; Sensitivity=0.23; Specificity=0.97; Accuracy=0.77).

Of the 5 metabolomic variables exhibiting a nominal univariate association for $S_{IFNF}^{aCAD}$, a panel of all five metabolomic variables were selected as best predictors; these were combined with age and gender in a prediction model for CAD. Table 50 provides the relative influence of the five metabolomic variables in combination with age and gender for the Metabolomics Model of $S_{IFNF}^{aCAD}$. FIG. 48 provides a ROC curve for the Metabolomics Model of $S_{IFNF}^{aCAD}$. Table 56 provides the sensitivity, specificity, positive predictive value (PPV) and negative predictive value (NPV) for the range of predicted probability thresholds; Area Under the Curve (AUC) and accuracy was estimated.

TABLE 50

| Variable | Relative Influence | Direction of Change |
| --- | --- | --- |
| Age | 40.82 | Elevated |
| 2-hydroxyhippurate (salicylurate) | 19.56 | Elevated |
| threonate | 14.84 | Decreased |
| salicylate | 12.23 | Elevated |
| Male gender | 7.00 | Present |
| N-acetylglycine | 3.13 | Decreased |
| 3-ethylphenylsulfate | 2.42 | Elevated | c. Analytes Significant in Fasting—$S_F^{aCAD}$ i. Of the 481 analytes measured, 40 metabolomic variables exhibited a nominal univariate association (raw p<0.05) for $S_F^{aCAD}$. Table 51 provides a filtered list of the 40 metabolomic variables for $S_F^{aCAD}$.

TABLE 51

| | | |
| --- | --- | --- |
| N-octanoylglycine | salicylate | Dimethylglycine |
| 1-oleoylglycerol (18:1) | 7-methylguanine | xylonite |
| isovalerylglycine | lysine | Phenylalanylphenylalanine |
| N-acetylglycine | glycoursodeoxycholate | Valylisoleucine |
| 2-linolenoylglycerophosphocholine(18:3n3)* | 3-indoxyl sulfate | Glycerate |
| asparagine | 6-oxopiperidine-2-carboxylic acid | 1-arachidonylglycerol |
| isobutyrylglycine (C4) | 1-arachidonoylglyercophosphate | Fumarate |
| cyclo (leu-pro) | 2-hydroxyhippurate (salicylurate) | 3-ethylphenylsulfate |
| cholate | threitol | 7-HOCA |
| serotonin (5HT) | methionine | Taurine |
| threonate | acisoga | Cholesterol |
| N-acetylputrescine | tigloylglycine | Arabitol |
| propionylglycine (C3) | 1-linoleoylglycerol (18:2) | — |
| 2-oleoyl-GPE* (18:1)* | 1-oleoyl-GPI (18:1)* | — |

Figure 49:
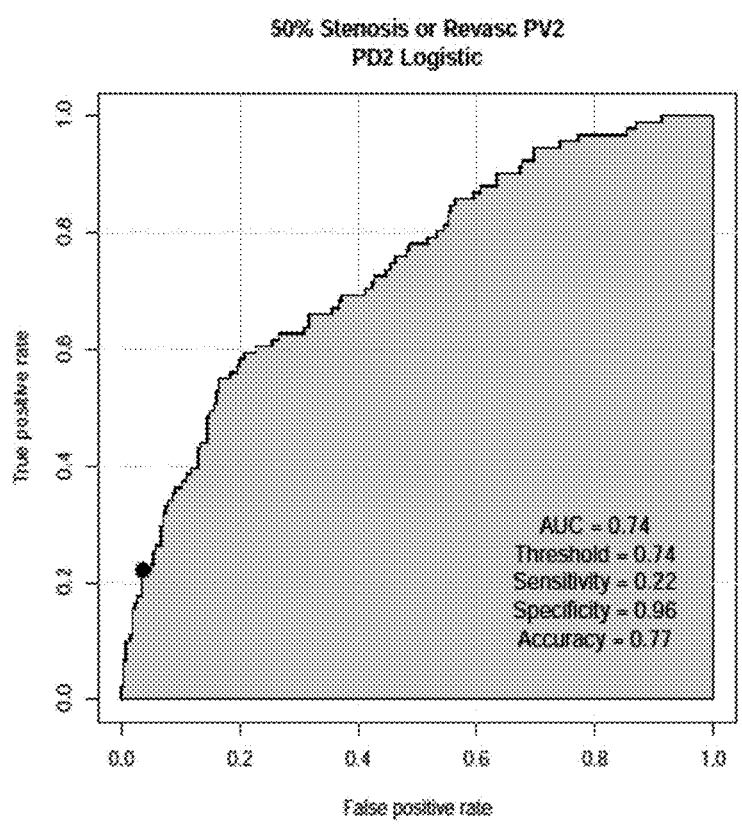
FIG. 49 is a graph demonstrating a ROC curve for the Metabolomic Model of $S_F^{aCAD}$ (AUC=0.74; Threshold=0.74; Sensitivity=0.22; Specificity=0.96; Accuracy=0.77).

Of the 40 metabolomic variables exhibiting a nominal univariate association for $S_F^{aCAD}$, a panel of eight metabolomic variables were selected as best predictors; these were combined with age and gender in a prediction model for CAD. Table 52 provides the relative influence of the eight metabolomic variables in combination with age and gender for the Metabolomics Model of $S_F^{aCAD}$. FIG. 49 provides a ROC curve for the Metabolomics Model of $S_F^{aCAD}$. Table 56 provides the sensitivity, specificity, positive predictive value (PPV) and negative predictive value (NPV) for the range of predicted probability thresholds; Area Under the Curve (AUC) and accuracy was estimated.

TABLE 52

| Variable | Relative Influence | Direction of Change |
| --- | --- | --- |
| age | 15.37 | Elevated |
| cholesterol | 15.19 | Decreased |
| 1-oleoylglycerol (18:1) | 15.12 | Elevated |
| acisoga | 14.01 | Elevated |
| 2.hydroxyhippurate (salicylurate) | 9.47 | Elevated |
| asparagine | 8.18 | Elevated |
| taurine | 7.93 | Decreased |
| 6-oxopiperidine-2-carboxylic acid | 7.50 | Elevated |
| propionylglycine (C3) | 6.66 | Decreased |
| Male gender | 0.56 | Present |

For each model below, the sensitivity, specificity, positive predictive value (PPV) and negative predictive value (NPV) were calculated for the range of predicted probability thresholds (Tables 53, 54, 55, 56). A Receiver Operating Characteristic (ROC) curve was generated to plot sensitivity as a function of (1-specificity). The optimal classification threshold was determined on the basis of accuracy, defined as the proportion of correct predictions. In addition, the Area Under the Curve (AUC) and accuracy was estimated (Tables 53, 54, 55, 56 for Native CAD, All CAD, 50% stenosis in Native CAD, and 50% stenosis in All CAD, respectively). The first row for each model indicates the performance of the maximum accuracy threshold, the optimal balance between sensitivity and specificity. Those models with a second row were optimized for a high negative predictive value (NPV).

TABLE 53

| Model | AUC | Sensitivity | Specificity | Positive Predictive Value | Negative Predictive Value | Accuracy |
| --- | --- | --- | --- | --- | --- | --- |
| DF | 0.45 | 1.00 | 0.00 | 0.62 | N/A | 0.62 |
| $A_{FNF}^{nCAD}$ | 0.82 | 0.85 | 0.61 | 0.78 | 0.71 | 0.76 |
| | | 0.99 | 0.09 | 0.64 | 0.92 | 0.65 |
| $A_{IFNF}^{nCAD}$ | 0.80 | 0.85 | 0.64 | 0.80 | 0.72 | 0.77 |
| | | 1.00 | 0.10 | 0.65 | 0.93 | 0.66 |
| $A_F^{nCAD}$ | 0.81 | 0.87 | 0.58 | 0.77 | 0.74 | 0.76 |
| | | 0.99 | 0.26 | 0.69 | 0.94 | 0.72 |

DF = Diamond-Forrester

TABLE 54

| Model | AUC | Sensitivity | Specificity | Positive Predictive Value | Negative Predictive Value | Accuracy |
| --- | --- | --- | --- | --- | --- | --- |
| DF | 0.45 | 1.00 | 0.00 | 0.64 | N/A | 0.64 |
| $A_{FNF}^{aCAD}$ | 0.83 | 0.93 | 0.50 | 0.77 | 0.81 | 0.78 |
| | | 1.00 | 0.16 | 0.68 | 0.95 | 0.69 |

TABLE 54-continued

| Model | AUC | Sensitivity | Specificity | Positive Predictive Value | Negative Predictive Value | Accuracy |
| --- | --- | --- | --- | --- | --- | --- |
| $A_{IFNF}^{aCAD}$ | 0.81 | 0.85 | 0.66 | 0.81 | 0.71 | 0.78 |
| | | 1.00 | 0.07 | 0.65 | 0.90 | 0.66 |
| $A_F^{aCAD}$ | 0.82 | 0.83 | 0.64 | 0.80 | 0.68 | 0.76 |
| | | 1.00 | 0.16 | 0.68 | 0.95 | 0.69 |

DF = Diamond-Forrester

TABLE 55

| Model | AUC | Sensitivity | Specificity | Positive Predictive Value | Negative Predictive Value | Accuracy |
| --- | --- | --- | --- | --- | --- | --- |
| DF | 0.45 | 0.03 | 1.00 | 1.00 | 0.78 | 0.78 |
| $S_{FNF}^{nCAD}$ | 0.73 | 0.21 | 0.96 | 0.64 | 0.80 | 0.79 |
| | | 0.95 | 0.30 | 0.29 | 0.95 | 0.45 |
| $S_{IFNF}^{nCAD}$ | 0.76 | 0.30 | 0.96 | 0.72 | 0.82 | 0.81 |
| | | 0.93 | 0.37 | 0.31 | 0.95 | 0.50 |
| $S_F^{nCAD}$ | 0.67 | 0.04 | 1.00 | 1.00 | 0.78 | 0.78 |
| | | 0.96 | 0.20 | 0.26 | 0.95 | 0.38 |

DF = Diamond-Forrester

TABLE 56

| Model | AUC | Sensitivity | Specificity | Positive Predictive Value | Negative Predictive Value | Accuracy |
| --- | --- | --- | --- | --- | --- | --- |
| DF | 0.45 | 0.03 | 1.00 | 1.00 | 0.74 | 0.75 |
| $S_{FNF}^{aCAD}$ | 0.78 | 0.34 | 0.94 | 0.66 | 0.80 | 0.78 |
| | | 0.96 | 0.30 | 0.33 | 0.95 | 0.47 |
| $S_{IFNF}^{aCAD}$ | 0.78 | 0.23 | 0.97 | 0.72 | 0.78 | 0.77 |
| | | 0.96 | 0.30 | 0.33 | 0.95 | 0.47 |
| $S_F^{aCAD}$ | 0.74 | 0.22 | 0.96 | 0.69 | 0.78 | 0.77 |
| | | 0.97 | 0.22 | 0.31 | 0.95 | 0.42 |

DF = Diamond-Forrester

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for evaluating a human subject for having atherosclerotic coronary artery disease (ASCAD) or as having a coronary atherosclerotic plaque, the method comprising:
 measuring the levels of each analyte within a panel of analyte biomarkers in a blood sample, a serum sample or a plasma sample obtained from the subject,
 comparing the measured levels of the analytes in the biological sample with one or more reference samples, wherein the reference samples are representative of matched human subjects; and
 identifying the subject as having atherosclerotic coronary artery disease or as having a coronary atherosclerotic plaque if measured levels of the analytes in the biological sample are increased or decreased relative to the amounts of the analytes in the reference samples,
 wherein the panel of analyte biomarkers and biomarker levels is selected from the group consisting of:
  (i) a panel of biomarkers comprising valylleucine, glutamate, acisoga, urate, glucuronate, fucose, butyrylcarnitine (C4), and mannose, wherein valylleucine is decreased, glutamate is increased, acisoga is increased, urate is increased, glucoronate is increased, fucose is increased, butyrylcarnitine (C4) is increased, and mannose is increased; and
  (ii) a panel of biomarkers comprising glutamate, acisoga, valylleucine, mannose, glucuronate, urate, valerylcarnitine (C5), and 12-HETE, wherein glutamate is increased, acisoga is increased, valylleucine is decreased, mannose is increased, glucoronate is increased, urate is increased, valerylcarnitine (C5) is increased, and 12-HETE is decreased.

2. The method of claim 1, further comprising instructing a healthcare professional to complete a non-invasive cardiovascular evaluation on a subject identified as having atherosclerotic coronary artery disease or as having a coronary atherosclerotic plaque to confirm the subject has or does not have atherosclerotic coronary artery disease or a coronary atherosclerotic plaque.

3. The method of claim 1, further comprising performing a non-invasive cardiovascular evaluation on a subject identified as having atherosclerotic coronary artery disease or as having a coronary atherosclerotic plaque to confirm the subject does or does not have atherosclerotic coronary artery disease or a coronary atherosclerotic plaque.

4. The method of claim 2, wherein performing a non-invasive cardiovascular evaluation comprises performing a procedure selected from the group consisting of cardiovascular computed tomography (CT) imaging, an exercise stress test, a pharmacologic stress test, myocardial perfusion imaging, stress echocardiography, and cardiovascular magnetic resonance imaging.

5. The method of claim 1, further comprising selectively administering a composition comprising an effective amount of a therapeutic agent selected from the group consisting of a statin, cholesterol absorption inhibitors, niacin-derivatives, omega-3-fatty acid compounds, bile acid sequestrants, antiplatelet agents, aldosterone blockers, angiotensin-converting enzyme (ACE) inhibitors, angiotensin-receptor blockers (ARBs), beta blockers, diuretics, digitalis, hydralazine, nitrates, warfarin and aspirin to a subject identified as having atherosclerotic coronary artery disease or as having a coronary atherosclerotic plaque to treat the subject.

6. The method of claim 1, further comprising selecting a treatment plan for a subject identified as having atherosclerotic coronary artery disease or as having a coronary atherosclerotic plaque to treat the subject.

7. The method of claim 6, wherein the treatment plan comprises selectively administering a composition comprising administering an effective amount of a therapeutic agent selected from the group consisting of a statin, cholesterol absorption inhibitors, niacin-derivatives, omega-3-fatty acid compounds, bile acid sequestrants, PCSK9 antagonists, antiplatelet agents, aldosterone blockers, angiotensin-converting enzyme (ACE) inhibitors, angiotensin-receptor blockers (ARBs), beta blockers, diuretics, digitalis, hydralazine, nitrates, warfarin and aspirin.

8. The method of claim 1, wherein the levels are measured using mass spectrometry (MS) analysis.

9. The method of claim 8, wherein the MS analysis comprises liquid chromatography-tandem mass spectrometry (UPLC-MS/MS) or gas chromatography-mass spectrometry (GC-MS).

10. The method of claim 1, wherein the subject presents with symptoms of atherosclerotic CAD comprising chest pain, angina, angina equivalent, dyspnea, or dyspnea on exertion.

11. The method of claim 1, wherein the subject presents with risk factors associated with coronary artery disease selected from the group consisting of male gender, hypertension, dyslipidemia, diabetes, and a family history of coronary artery disease.

12. The method of claim 1, wherein the subject has no previous history of coronary artery disease.

13. The method of claim 1, wherein the reference sample is obtained from at least one individual not suffering from a cardiovascular disease.

14. The method of claim 1, wherein the reference sample comprises predetermined, statistically significant reference analyte levels.

15. The method of claim 1, wherein the identifying step is performed using a gradient boosting algorithm, a decision tree model, or a linear regression analyses.

16. The method of claim 1, further comprising modifying the subject's clinical record to identify the subject as having atherosclerotic coronary artery disease or as having a coronary atherosclerotic plaque.

17. The method of claim 16, wherein the clinical record is stored in a computer readable medium.

18. The method of claim 1, further comprising selecting a subject identified as having atherosclerotic coronary artery disease or as having a coronary atherosclerotic plaque for treatment, wherein the treatment comprises selectively administering a composition comprising an effective amount of a therapeutic agent selected from the group consisting of a statin, cholesterol absorption inhibitors, niacin-derivatives, omega-3-fatty acid compounds, bile acid sequestrants, PCSK9 antagonists, anti-platelet agents, aldosterone blockers, angiotensin-converting enzyme (ACE) inhibitors, angiotensin-receptor blockers (ARBs), beta blockers, diuretics, digitalis, hydralazine, nitrates, warfarin and aspirin to a subject identified as having atherosclerotic coronary artery disease or as having a coronary atherosclerotic plaque to treat the subject.

19. The method of claim 1, further comprising selecting a subject identified as having atherosclerotic coronary artery disease or as having a coronary atherosclerotic plaque for treatment, wherein the treatment comprises performing a non-invasive cardiovascular evaluation on a subject identified as having atherosclerotic coronary artery disease or as having a coronary atherosclerotic plaque to confirm the subject does or does not have atherosclerotic coronary artery disease or a coronary atherosclerotic plaque.

20. The method of claim 6, wherein the treatment plan comprises prescribing therapeutic lifestyle changes.

21. The method of claim 6, wherein the treatment plan comprises performing a non-invasive cardiovascular evaluation comprises performing a procedure selected from the group consisting of cardiovascular computed tomography (CT) imaging, an exercise stress test, a pharmacologic stress test, myocardial perfusion imaging, stress echocardiography, and cardiovascular magnetic resonance imaging.

22. The method of claim 1, wherein the comparing step includes analysis of the subject's age and/or gender.

23. The method of claim 5, wherein the therapeutic agent is a statin.

* * * * *

SEQUENCE LISTING

```
<160> NUMBER OF SEQ ID NOS: 1

<210> SEQ ID NO 1
<211> LENGTH: 16
<212> TYPE: PRT
<213> ORGANISM: Homo sapiens
<220> FEATURE:
<221> NAME/KEY: VARIANT
<222> LOCATION: 9
<223> OTHER INFORMATION: Xaa = Any Amino Acid

<400> SEQUENCE: 1

Ala Asp Ser Gly Glu Gly Asp Phe Xaa Ala Glu Gly Gly Gly Val Arg
1               5                   10                  15
```